(12) United States Patent  (10) Patent No.: US 6,638,212 B1
Oshima  (45) Date of Patent: Oct. 28, 2003

(54) ENDOSCOPE SYSTEM HAVING STORAGE PART OF ENDOSCOPE-RELATED-DATA PROVIDED IN ENDOSCOPE

(75) Inventor: Ryu Oshima, Hino (JP)

(73) Assignee: Olympus Optical (JP)

(*) Notice: Subject to any disclaimer, the term of this patent is extended or adjusted under 35 U.S.C. 154(b) by 337 days.

(21) Appl. No.: 09/625,699

(22) Filed: Jul. 25, 2000

(30) Foreign Application Priority Data

Jul. 27, 1999 (JP) .......................................... 11-212506
May 18, 2000 (JP) ........................................ 2000-146952

(51) Int. Cl.$^7$ ............................................. A61B 1/045
(52) U.S. Cl. ...................... 600/109; 600/110; 600/118; 348/72; 348/74
(58) Field of Search ............................. 600/109, 110, 600/118, 103, 100, 101; 348/65, 72, 74, 76

(56) References Cited

U.S. PATENT DOCUMENTS

| 4,584,663 A | * | 4/1986 | Tanikawa | .................... 365/201 |
| 4,667,229 A | | 5/1987 | Cooper et al. | |
| 4,827,908 A | | 5/1989 | Matsuo | |
| 4,949,313 A | * | 8/1990 | Iwasawa | ....................... 367/7 |
| 4,996,975 A | * | 3/1991 | Nakamura | .................... 348/74 |
| 5,400,267 A | * | 3/1995 | Denen et al. | ................ 128/908 |
| 5,568,271 A | * | 10/1996 | Fukuchi et al. | ............... 348/74 |
| 5,830,121 A | | 11/1998 | Enomoto et al. | |
| 6,295,082 B1 | * | 9/2001 | Dowdy et al. | ......... 348/231.99 |
| 6,313,868 B1 | * | 11/2001 | D'Alfonso et al. | ........... 348/72 |
| 6,390,972 B1 | * | 5/2002 | Speier et al. | ................ 348/73 |
| 6,434,648 B1 | * | 8/2002 | Assour et al. | ................ 710/62 |
| 6,436,032 B1 | * | 8/2002 | Eto et al. | ..................... 600/117 |

FOREIGN PATENT DOCUMENTS

| EP | 0534198 | | 3/1993 |
| EP | 0669756 | | 8/1995 |
| JP | 60042743 | * | 3/1985 |
| JP | 61-205912 | | 9/1986 |
| JP | 61-244323 | | 10/1986 |
| JP | 62-199190 | | 9/1987 |
| JP | 63-240827 | | 10/1988 |
| JP | 63-260523 | | 10/1988 |
| JP | 3-4831 | | 1/1991 |
| JP | 4-127113 | | 4/1992 |
| JP | 6-315110 | | 11/1994 |
| JP | 8-24220 | | 1/1996 |
| JP | 8-22272 | | 3/1996 |
| JP | 2543855 | | 7/1996 |
| JP | 2653647 | | 5/1997 |
| JP | 9-113820 | | 5/1997 |
| JP | 2713840 | | 10/1997 |

* cited by examiner

Primary Examiner—John P. Leubecker
(74) Attorney, Agent, or Firm—Ostrolenk, Faber, Gerb & Soffen, LLP

(57) ABSTRACT

A nonvolatile, programmable memory is incorporated in an endoscope. Endoscope-related data closely relevant to the endoscope, such as, an endoscope model name and the number of power feeds are stored in the nonvolatile memory. The endoscope is connected to an external image processing apparatus, and endoscope-related data is read from the nonvolatile memory. Based on the read endoscope-related data, the use situation of the endoscope is grasped or the endoscope is managed. The number of power feeds is varied depending on the use situation of the endoscope, and written in the nonvolatile memory. Thus, the endoscope-related data is used to maintain the endoscope and reduce a load to be incurred by the external image processing apparatus that is a connected apparatus. Consequently, the endoscope can be managed and maintained easily using a small software system.

53 Claims, 49 Drawing Sheets

FIG.3

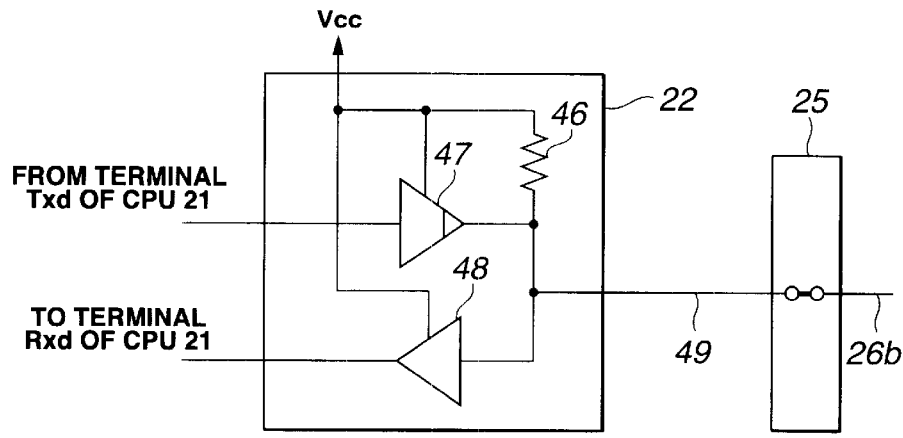

FROM TERMINAL Txd OF CPU 21

TO TERMINAL Rxd OF CPU 21

FIG.4A

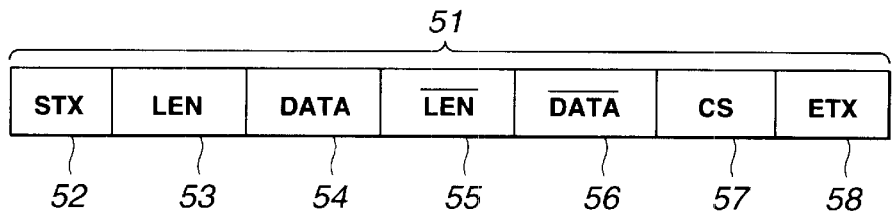

| STX | LEN | DATA | $\overline{\text{LEN}}$ | $\overline{\text{DATA}}$ | CS | ETX |
|-----|-----|------|------|------|-----|-----|
| 52  | 53  | 54   | 55   | 56   | 57  | 58  |

FIG.4B

| ITEMS | DESCRIPTION |
|-------|-------------|
| STX52 | START OF TEXT<br>IT INDICATES THE START OF A BLOCK. |
| LEN53 | IT SPECIFIES A DATA LENGTH PERMITTED FOR DATA. |
| DATA54 | IT SPECIFIES AN INSTRUCTION INDICATING THE CONTENTS OF PROCESSING AND DATA TO BE READ OR WRITTEN. |
| $\overline{\text{LEN}}$55 | IT SPECIFIES THE REVERSE OF DATA SPECIFIED FOR LEN. |
| $\overline{\text{DATA}}$56 | IT SPECIFIES THE REVERSE OF DATA SPECIFIED FOR DATA. |
| CS57 | IT SPECIFIES A CHECKSUM. |
| ETX58 | END OF TEXT<br>IT INDICATES THE END OF A BLOCK. |

(NOTE THAT $\overline{\text{LEN}}$ IS EXPRESSED AS \LEN IN THE SPECIFICATION.)

FIG.7A

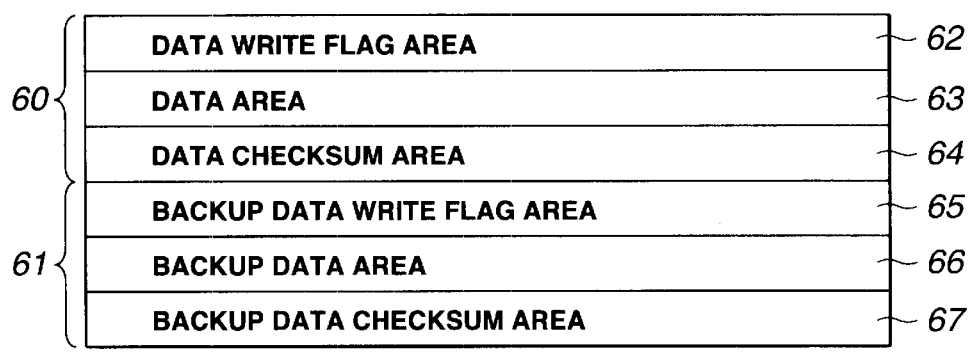

FIG.7B

| AREAS | DESCRIPTION |
|---|---|
| DATA WRITE FLAG AREA 62 | A FLAG USED TO CHECK IF DATA HAS CORRECTLY BEEN WRITTEN IN THE DATA AREA IS STORED THEREIN. |
| DATA AREA 63 | DATA IS STORED THEREIN. |
| DATA CHECKSUM AREA 64 | A CHECKSUM OF DATA STORED IN THE DATA AREA IS STORED THEREIN. |
| BACKUP DATA WRITE FLAG AREA 65 | A FLAG USED TO CHECK IF BACKUP DATA HAS CORRECTLY BEEN WRITTEN IN THE BACKUP DATA AREA IS STORED THEREIN. |
| BACKUP DATA AREA 66 | BACKUP DATA IS STORED THEREIN. |
| BACKUP DATA CHECKSUM AREA 67 | A CHECKSUM OF DATA STORED IN THE BACKUP DATA AREA IS STORED THEREIN. |

FIG.24

| ITEMS OF DATA | DESCRIPTION |
|---|---|
| ENDOSCOPE MODEL NAME | IT SPECIFIES THE MODEL OF AN ENDOSCOPE. |
| STRUCTURE OF THE DISTAL PART OF AN ENDOSCOPE | IT INDICATES WHETHER THE DISTAL PART OF AN ENDOSCOPE IS OF A DIREST-VIEWING TYPE, A SIDE-VIEWING TYPE, OR AN OBLIQUE-VIEWING TYPE. |
| CLEANING TUBE/ADAPTOR NAME | IT SPECIFIES A CLEANING TUBE OR ADAPTOR TO BE ATTACHED TO AN ENDOSCOPE PRIOR TO CLEANING WHEN A CLEANING APPARATUS (3C IN FIG.1) IS CONNECTED TO THE ENDOSCOPE. |
| CCD MODEL NAME | IT SPECIFIES THE MODEL OF A CCD. |
| NAME OF AN OPTICAL FILTER IN A CCD | IT SPECIFIES AN OPTICAL FILTER INCLUDED IN A CCD. |
| INFORMATION OF CHANNELS IN AN ENDOSCOPE | IT REPRESENTS INFORMATION CONCERNING CHANNELS IN AN ENDOSCOPE 2 AND SPECIFIES THE NUMBER OF CHANNELS IN THE ENDOSCOPE, THE DIAMETERS OF THE CHANNELS, AND THE AIRFLOW RATES IN THE CHANNELS. |
| INFORMATION OF SWITCHES ON AN ENDOSCOPE | IT REPRESENTS INFORMATION CONCERNING SWITCHES ON AN ENDOSCOPE 2 AND SPECIFIES THE NUMBER OF SWITCHES ON THE ENDOSCOPE AND THE FUNCTIONS OF THE SWITCHES. |
| VERSION NUMBER | IT REPRESENTS A VERSION OF A PROGRAM. |
| IDENTIFICATION DATA | IT SPECIFIES A SERIAL NUMBER OF AN ENDOSCOPE. |
| COUNT DATA | IT SPECIFIES THE NUMBER OF POWER FEEDS BY WHICH POWER IS FED TO AN ENDOSCOPE. |
| REPROCESSING COMPLETION TIME INSTANT | IT REPRESENTS A TIME INSTANT AT WHICH CLEANING STARTED BY A CLEANING APPARATUS (3C IN FIG.1) IS COMPLETED. THE TIME INSTANT IS USED TO JUDGE WHETHER REPROCESSING IS COMPLETED. WHEN BITS ASSIGNED TO THE TIME INSTANT ARE ALL CLEARED (SET TO, FOR EXAMPLE, FFh), IT MEANS THAT REPROCESSING IS UNCOMPLETED. WHEN THE BITS INDICATE ANY OTHER VALUE, IT MEANS THAT REPROCESSING IS COMPLETED. |
| CONTENTS OF A CLEAN INSTRUCTION | IT REPRESENTS A CLEAN INSTRUCTION ISSUED FROM A CLEANING APPARATUS (3C IN FIG.1) FOR CLEANING. |
| RESULTS OF AN AUTOMATIC LEAKAGE TEST | IT REPRESENTS THE RESULTS OF AN AUTOMATIC LEAKAGE TEST PREFORMED BY A CLEANING APPARATUS (3C IN FIG.1). |
| NAME OF AN EXECUTOR OF REPROCESSING | IT REPRESENTS THE NAME OF AN EXECUTOR WHO HAS PERFORMED CLEANING USING A CLEANING APPARATUS (3C IN FIG.1). |
| INITIAL EXAMINATION DAY | IT REPRESENTS A DAY ON WHICH AN ENDOSCOPE 2 IS USED FOR EXAMINATION FOR THE FIRST TIME OR THE ENDOSCOPE 2 IS DELIVERED. |
| INSTITUTION NAME | IT REPRESENTS THE NAME OF AN INSTITUTION IN WHICH AN ENDOSCOPE 2 IS USED OR THE NAME OF AN OWNER OF THE ENDOSCOPE 2. |
| REPAIR RECORD | IT SPECIFIES RECORDED REPAIRS PERFORMED ON AN ENDOSCOPE 2. |
| INSPECTION RECORD | IT SPECIFIES RECORDED INSPECTIONS PERFORMED ON AN ENDOSCOPE 2. |
| USER'S COMMENT | IT REPRESENTS ANY DATA ENTERED BY A USER, SUCH AS, THE SIZES OF CHANNELS IN AN ENDOSCOPE 2, AND A FREQUENCY AT WHICH AN ULTRASONIC DEVICE (NOT SHOWN) OSCILLATES. |
| REPROCESSING COUNT DATA | IT REPRESENTS COUNT DATA INDICATING THE NUMBER OF TIMES BY WHICH REPROCESSING (CLEANING) IS PREFORMED WITH AN ENDOSCOPE CONNECTED TO A CLEANING APPARATUS 3C. |
| EXPIRATION DATA OF GUARANTEE | IT REPRESENTS AN EXPIRATION DATA OF GUARANTEE ON AN ENDOSCOPE 2. |
| PRESENCE OR ABSENCE OF A CONTRACT ON A SERVICE | IT INDICATES WHETHER A CONTRACT HAS BEEN MADE ON A SERVICE FOR AN ENDOSCOPE. IF A CONTRACT HAS BEEN MADE, A CONTRACT NUMBER IS INDICATED. |
| RESULTS OF A CHECK FOR CLOGGING OF A NOZZLE | IT REPRESENTS THE RESULTS OF A CHECK PREFORMED TO SEE IF A NOZZLE IN AN ENDOSCOPE 2 IS CLOGGED. |
| MAKER'S COMMENT | IT REPRESENTS ANY DATA ENTERED BY A MANUFACTURER. |
| SERVICE ENGINEER'S COMMENT | IT REPRESENTS ANY DATA ENTERED BY A SERVICE ENGINEER. |
| PREVIOUS EXAMINATION TIME INSTANT | IT REPRESENTS A TIME INSTANT AT WHICH EXAMINATION IS PREFORMED PREVIOUSLY WITH AN ENDOSCOPE CONNECTED TO AN IMAGE PROCESSING APPARATUS 3A. |
| FIXTURE NUMBER | IT REPRESENTS A NUMBER ASSIGNED TO AN ENDOSCOPE 2 IN AN INSTITUTION IN WHICH THE ENDOSCOPE 2 IS EMPLOYED. |

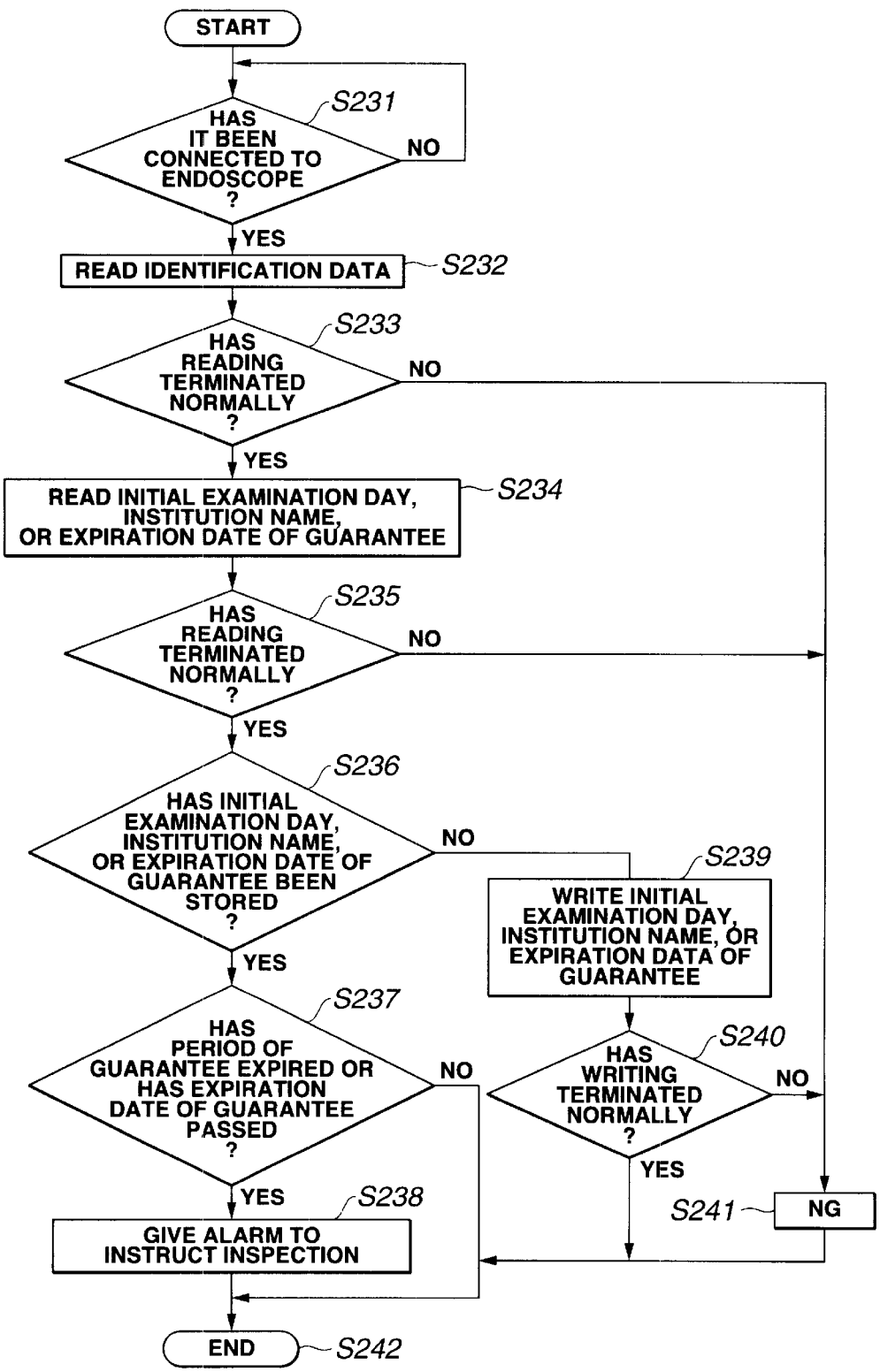

FIG.32

| | |
|---|---|
| Service Contract | 1 2 3 4 <u>5</u> |
| User Comment | Comment 1 |
| Olympus Comment | Comment 2 |
| Service Comment | Comment 3 |
| Fixture No. | 0012234 |
| First Day | 01/04/1999 |
| Warranty | 03/02/2006 |
| Hospital Name | Hospital 1 |
| Repair Information | Repair 1 |
| Quality Problem Information | Info 1 |
| Scope | GIF-Q160 |
| Serial NO. | 2814211 |
| Last Inspection Data | 17/04/1999 |
| Last Reprocess | 16/04/1999 |
| Inspection Count Data | 4 |
| Reprocess Count Data | 3 |
| Ver. | 1.01 |

| PARAMETERS | | DESCRIPTION |
|---|---|---|
| ENDOSCOPE MODEL NAME | SCOPE MODEL | IT REPRESENTS THE MODEL OF AN ENDOSCOPE. |
| SERIAL NUMBER | SERIAL NO. | IT REPRESENTS A SERIAL NUMBER ASSIGNED TO AN ENDOSCOPE. |
| NUMBER OF POWER FEEDS | CUMULATIVE USES | IT REPRESENTS THE NUMBER OF POWER FEEDS BY WHICH POWER IS FED AN ENDOSCOPE CONNECTED TO AN IMAGE PROCESSING APPARATUS. |
| NUMBER OF INSPECTIONS | CHECK PERIOD | IT CORRESPONDS TO THE NUMBER OF POWER FEEDS BY WHICH POWER IS FED IN ORDER TO DISPLAY AN INDICATION PROMPTING A USER TO PREFORM INSPECTION. WHEN THE CUMULATIVE NUMBER OF POWER FEEDS BECOMES EQUAL TO OR LARGER THAN A SET NUMBER OF INSPECTIONS, THE INDICATION PROMPTING A USER TO PERFORM INSPECTION, THAT IS, "CHECK-UP DUE" IS DISPLAYED. |
| OWNER NAME OR INSTITUTION NAME | OWNER | IT REPRESENTS THE NAME OF AN OWNER OR AN INSTITUTION. |
| REPAIR RECORD | REPAIR INFO. | IT SPECIFIES RECORDED REPAIRS. |
| INSPECTION RECORD | CHECKUP INFO. | IT SPECIFIES RECORDED INSPECTIONS. |
| EXPIRATION DATE OF GUARANTEE | WARRANTY DATE | IT REPRESENTS AN EXPIRATION DATE OF GUARANTEE ON AN ENDOSCOPE. |
| PRESENCE OR ABSENCE OF A CONTRAST ON A SERVICE | SERVICE CONTRACT | IT INDICATES WHETHER A CONTRAST HAS BEEN MADE ON A SERVICE FOR AN ENDOSCOPE. |
| USER'S COMMENT | COMMENTS | IT REPRESENTS ANY DATA ENTERED BY A USER. |
| MAKER'S COMMENT | MFG. COMMENTS | IT REPRESENTS ANY DATA ENTERED OR CHECKED BY A MANUFACTURER. |
| SERVICE ENGINEER'S COMMENT | SERVICE COMMENTS | IT REPRESENTS ANY DATA ENTERED OR CHECKED AT A SERVICE CENTER. |
| FIXTURE NUMBER | CUSTOMER ID NO. | IT REPRESENTS A NUMBER ASSIGNED TO A FIXTURE THAT IS AN ENDOSCOPE. |
| VERSION NUMBER | ID VER. | IT REPRESENTS A VERSION OF A PROGRAM INSTALLED IN A CPU IN AN ENDOSCOPE. |
| WHITE BALANCE DATA | — | IT INDICATED THAT WHITE BALANCE DATA IS STORED. |
| CCD MODEL NAME | — | IT REPRESENTS THE MODEL OF A CCD. |
| REPROCESSING COUNT DATA | — | IT REPRESENTS THE NUMBER OF TIMES BY WHICH REPROCESSING IS PREFORMED WITH AN ENDOSCOPE CONNECTED TO A CLEANING APPARATUS. |
| PREVIOUS EXAMINATION TIME INSTANT | — | IT REPRESENTS A TIME INSTANT AT WHICH THE POWER SUPPLY OF AN ENDOSCOPE IS TURNED ON PREVIOUSLY WITH THE ENDOSCOPE CONNECTED TO AN IMAGE PROCESSING APPARATUS. |
| INFORMATION OF CHANNELS | — | IT REPRESENTS INFORMATION CONCERNING CHANNELS IN AN ENDOSCOPE. |
| REPROCESSING COMPLETION TIME INSTANT | — | IT REPRESENTS A TIME INSTANT AT WHICH REPROCESSING IS COMPLETED. IT IS JUDGED FROM THE TIME INSTANT WHETHER REPROCESSING IS COMPLETED. |
| CONTENTS OF A CLEAN INSTRUCTION | — | IT REPRESENTS THE CONTENTS OF A CLEAN INSTRUCTION ISSUED FOR CLEANING TO BE PREFORMED BY A CLEANING APPARATUS. |
| RESULTS OF AN AUTOMATIC LEAKAGE TEST | — | IT REPRESENTS THE RESULTS OF AN AUTOMATIC LEAKAGE TEST PREFORMED ON A CLEANING APPARATUS. |
| RESULTS OF A CHECK FOR CLOGGING OF A NOZZLE | — | IT REPRESENTS THE RESULTS OF A CHECK PERFORMED TO SEE IF A NOZZLE IS CLOGGED. |
| INITIAL EXAMINATION DAY | — | IT REPRESENTS A DAY ON WHICH AN ENDOSCOPE IS USED FOR EXAMINATION FOR THE FIRST TIME, OR IN OTHER WORDS, A DAY ON WHICH THE POWER SUPPLY OF AN ENDOSCOPE CONNECTED TO AN IMAGE PROCESSING APPARATUS IS TURNED ON FOR FIRST TIME. |

FIG.46

| NUMBER | NAME | FUNCTION |
|---|---|---|
| 181 | PRINT KEY | IT IS USED TO CAUSE AN IMAGE RECORDING APPARATUS (FOR EXAMPLE, PRINTER) TO PERFORM PRINTING. |
| 182 | PRINT INDICATOR LED | IT IS LIT OR FLICKERED DURING PRINTING. |
| 183 | ENH. KEY | IT IS USED TO CHANGE THE DEGREE OF CONTOUR ENHANCEMENT OR STRUCTURE ENHANCEMENT TO BE PERFORMED ON AN ENDOSCOPIC VIEW IMAGE. |
| 184~186 | ENHANCE LEVEL INDICATOR LED | IT INDICATES THE DEGREE OF CONTOUR ENHANCEMENT OR STRUCTURE ENHANCEMENT. EVERY TIME THE ENHANCE KEY 183 IS PRESSED, THE INDICATION OF L, M, AND H ARE LIT ALTERNATELY AND REPEATEDLY. |
| 187 | IRIS | IT IS A SWITCH FOR CHANGING LIGHT ADJUSTMENT MODES. |
| 188~189 | PEAK / AVERAGE INDICATOR LED | IT INDICATES A LIGHT ADJUSTMENT MODE. EVERY TIME THE IRIS KEY 187 IS PRESSED, THE INDICATIONS OF PEAK AND AVERAGE ARE LIT ALTERNATELY. |
| 190 | WHITE BAL. KEY | IT IS A KEY USED TO EXTEND WHITE BALANCE CONTROL. WHEN A WHITE BALANCE IS NOT ATTAINED, THE INTERNAL LED IS LIT. |
| 191 | WHITE BAL. INDICATOR LED | WHEN IT IS LIT, IT MEANS THAT WHITE BALANCE CONTROL IS EXTENDED. WHEN IT IS UNLIT, IT MEANS THAT WHITE BALANCE CONTROL IS NOT EXTENDED. |
| 192 | SELECT | IT IS USED TO SELECT AN OBJECT OF ADJUSTMENT FROM AMONG THE INDICATIONS OF R, B, AND C. EVERY TIME THE SELECT KEY 192 IS PRESSED, THE INDICATIONS OF R, B, AND C ARE LIT ALTERNATELY AND REPEATEDLY. |
| 193, 194 | LEVEL SET KEY | IT IS USED TO INCREASE OR DECREASE THE LEVEL OF A TONE OR SATURATION SELECTED USING THE SELECT KEY 192. |
| 195 | COLOR ADJUSTMENT LEVEL INDICATOR LED (RED) | IT INDICATED THE LEVEL OR RED. |
| 196 | COLOR ADJUSTMENT LEVEL INDICATOR LED (BLUE) | IT INDICATED THE LEVEL OR BLUE. |
| 197 | COLOR ADJUSTMENT LEVEL INDICATOR LED (COLOR SATURATION) | IT INDICATED THE LEVEL OR SATURATION. |

FIG.47

```
Scope Information

Scope Model      GIF-Q160
Serial No.       2 9 0 0 0 0 4
Comments         RYU OSHIMA
Cumulative Uses  0 1 0 0
Check Period     0 2 5 0
Service Contract
Warranty Date
Owner
Customer ID NO.
ID Ver.
Mfg. Comments
Service Comments
Repair Info.
Checkup Info.

DISABLE!!
```
                                    110

FIG.48

```
Scope Information

Scope Model      GIF-Q160
Serial No.       2 9 0 0 0 0 4
Comments         RYU OSHIMA                         — 104
Cumulative Uses  0 1 0 0
Check Period     0 2 5 0                            — 105
Service Contract 1 2 3 4 5 6 7 8 9 0 1 2 3 4 5 6 7 8 9 0  — 105
Warranty Date    0 1 / 0 1 / 2 0 0 0                — 105
Owner            OLYMPUS OPTICAL CO.                — 105
Customer ID NO.  1 2 3 4 5 6 7 8 9 0 1 2 3 4 5 6 7 8 9 0  — 105
ID Ver.          1 . 0 2
Mfg. Comments    OLYMPUS                            — 105
Service Comments CHECK OK!                          — 105
Repair Info.     CHECK
Checkup Info.    CHECK 0 1 / 0 1 / 2 0 0 0

Enter Comments. ↑ ↓ to change item. "Enter" to save & exit. "Esc" to quite.  — 106
```

FIG.53

| IDENTIFICATION DATA | DESCRIPTION | WHETHER IT BE ENTERED IN THE FORM (○ : CAN BE ENTERED, ✕: CANNOT BE ENTERED) |
|---|---|---|
| SCOPE MODEL | MODEL OF AN ENDOSCOPE | ✕ |
| SERIAL NO. | SERIAL NUMBER ASSIGNED TO AN ENDOSCOPE | ✕ |
| COMMENTS | USER'S COMMMENT | ○ |
| CUMULATIVE USES | NUMBER OF POWER FEEDS | ✕ |
| CHECK PERIOD | NUMBER OF INSPECTIONS (WHEN THE NUMBER OF INSPECTIONS IS SET TO 0, AN INDICATION 75 OF AN INSPECTION TIME DISPLAYED IN AN ENDOSCOPIC IMAGE VIEWING FORM DISAPPEARS, AND A USER'S COMMENT IS DISPLAYED.) | ○ |
| SERVICE CONTRACT | WHETHER A CONTRACT HAS BEEN MADE ON A SERVICE IS INDICATED. | ○ |
| WARRANTY DATE | EXPIRATION DATE OF GUARANTEE | ○ |
| OWNER | NAME OF AN OWNER OR INSTITUTION | ○ |
| CUSTOMER ID NO. | NUMBER ASSIGNED TO A FIXTURE THAT IS AN ENDOSCOPE | ○ |
| ID VER. | VERSION NUMBER | ✕ |
| MFG. COMMENTS | MAKER'S COMMENT | ○ |
| SERVICE COMMENTS | SERVICE ENGINEER'S COMMENT | ○ |
| REPAIR INFO. | INFORMATION CONCERNING REPAIRS | ✕ |
| CHECKUP INFO. | INFORMATION CONCERNING INSPECTIONS | ✕ |

103

ENDOSCOPE SYSTEM HAVING STORAGE PART OF ENDOSCOPE-RELATED-DATA PROVIDED IN ENDOSCOPE

This application claims benefit of Japanese Application No. Hei 11-212506 filed in Japan on Jul. 27, 1999, and Japanese Application No. 2000-146952 filed in Japan on May 18, 2000, the contents of which are hereby incorporated by this reference.

BACKGROUND OF THE INVENTION

Field of the Invention and Description of the Related Art

The present invention relates to an endoscope system having an endoscope connected to a peripheral equipment such as an image processing apparatus in order to perform endoscopic examination or the like.

In the recent years, proposals have been made for an endoscope system having endoscope-related data assigned to an endoscope.

For example, an endoscope system disclosed in Japanese Unexamined Patent Application Publication No. 63-271217 includes an endoscope identification information assigned to an endoscope, an endoscope recognizing means, and a light level control means. The endoscope recognizing means recognizes the endoscope identification information, and the light level control means controls an amount of light emanating from a light source unit.

Japanese Examined Patent Application Publication No. 2713840 has disclosed an electronic endoscope system having an identification member, an identifying means, and a memory means. The identification member with which an electronic endoscope is identified is included in the electronic endoscope. The identifying means for identifying the identification member of the electronic endoscope and the memory means in which set values for attaining a white balance are stored in association with each electronic endoscope are included in a signal processing apparatus.

According to the foregoing related art, information assigned to an endoscope (endoscope identification information) cannot be rewritten. Endoscope-related data to be rewritten, such as, an initial examination day, an institution name, and a user's comment cannot be handled.

Moreover, a serial interface enabling data communication over a sole signal line is not used to enable peripheral equipment connected to an endoscope to recognize information assigned to the endoscope. Recognition units included in the endoscope and peripheral equipment alike have therefore a large configuration. This leads to an increase in size of the peripheral equipment. The peripheral equipment is therefore hard for a user to handle.

SUMMARY OF THE INVENTION

Accordingly, an object of the present invention is to provide an endoscope system that is easy to manage and maintain, and realized on a small scale.

Another object of the present invention is to provide an endoscope system in which endoscope-related data including a use situation of an endoscope can be checked readily.

According to the present invention, there is provided an endoscope system having an endoscope to be inserted into a subject in order to perform endoscopic examination, and peripheral equipment connected to the endoscope, wherein the endoscope includes:

a programmable storage medium in which data relevant to the endoscope is stored; and a serial interface to enable the reading or writing of endoscope-related data from or in the storage medium, and to serve as a communication unit for allowing the data to be transmitted or received to or from the peripheral equipment.

Consequently, endoscope-related data to be rewritten, such as, an initial examination day, an institution name, and a user's comment can be written or read. Endoscope-related data is stored in each endoscope and can therefore be managed easily.

An endoscope system in accordance with the present invention consists broadly of:

an endoscope having an imaging device, which images an object, incorporated in the distal part of an insertion unit to be inserted into a subject, and used to perform endoscopic examination;

an image processing apparatus, connected to the endoscope, for producing a video signal from an output signal of the imaging device;

a display device for displaying an image of the object according to the video signal to be input;

a programmable storage medium included in the endoscope and used to store endoscope-related data relevant to the endoscope;

a communication unit to enable the writing or reading of endoscope-related data in or from the storage medium, and to allow the data to be communicated to or from the image processing apparatus; and a control unit to enable the display of the endoscope-related data on the display device at any time.

Consequently, the endoscope-related data can be checked easily.

BRIEF DESCRIPTION OF THE DRAWINGS

FIG. 1 to FIG. 37 relate to the first embodiment of the present invention;

FIG. 1 is a block diagram showing the overall configuration of an endoscope system in accordance with the first embodiment of the present invention;

FIG. 2 is a block diagram showing in detail an electronic endoscope and an image processing apparatus having communication capability.

FIG. 3 is a circuit diagram showing an example of the circuitry of a selector 22;

FIG. 4A and FIG. 4B show a data structure for communication data and the contents of the communication data respectively;

FIG. 5 is a flowchart describing the steps to be performed in a connected apparatus (a connected piece of peripheral equipment) for writing (clearing) data in a nonvolatile memory included in an endoscope;

FIG. 6 is a flowchart describing the steps to be performed in the endoscope for allowing the connected apparatus to write (clear) data in a nonvolatile memory in the endoscope;

FIG. 7A and FIG. 7B show areas defined in the nonvolatile memory in the endoscope and the contents of the areas;

FIG. 8 is a flowchart describing the memory writing (clearing) mentioned in FIG. 6;

FIG. 9 is a flowchart describing the memory writing (Clearing) to be performed for writing data in a data division;

FIG. 10 is a flowchart describing the memory writing (clearing) to be performed for writing data in a backup data division;

FIG. 11 is a flowchart describing the steps to be performed in a connected apparatus for reading data from the nonvolatile memory in the endoscope;

FIG. 12 is a flowchart describing the steps to be performed in the endoscope for allowing the connected apparatus to read data from the nonvolatile memory in the endoscope;

FIG. 13 is a flowchart describing the memory reading mentioned in FIG. 12;

FIG. 14 is a flowchart describing the reading of a data division;

FIG. 15 is a flowchart describing the reading of a backup data division;

FIG. 16 is a flowchart describing the steps to be performed in a connected apparatus for enabling writing of data in the nonvolatile memory in the endoscope and then executing the writing;

FIG. 17 is a flowchart describing the steps to be performed in the endoscope for allowing the connected apparatus to enable the writing of data in the nonvolatile memory in the endoscope and to then execute the writing;

FIG. 18 is a flowchart describing actions to be performed in the endoscope in response to a command sent from the connected apparatus after write enabling is terminated;

FIG. 19 is a flowchart describing the steps to be performed in the connected apparatus for executing counting to treat the data stored in the nonvolatile memory in the endoscope;

FIG. 20 is a flowchart describing the steps to be performed in the endoscope for allowing the connected apparatus to execute counting so as to treat the data stored in the nonvolatile memory in the endoscope;

FIG. 21 is a flowchart describing the memory counting mentioned in FIG. 20;

FIG. 22 is a flowchart describing the steps to be performed in the endoscope for autonomously executing the counting;

FIG. 23 is a flowchart describing the steps to be performed in the endoscope for automatically clearing the cleaning-related information;

FIG. 24 shows items of endoscope-related data to be written in the nonvolatile memory and the contents of the data items;

FIG. 25 is a flowchart describing the steps to be performed in a connected apparatus for reading an initial examination day, an institution name, or an expiration date of a guarantee;

FIG. 26 shows an example of displaying on a monitor an indication of an inspection period;

FIG. 27 is a flowchart describing the processing for displaying part or the whole of endoscope-related data on the monitor or recording the endoscope-related data in an image recording apparatus or a filing apparatus;

FIG. 28 shows an example of displaying on the monitor an indication of endoscope-related data;

FIG. 29 is a flowchart describing the processing for treating cleaning-related information when an image processing apparatus or a filing apparatus that has the ability to communicate with the endoscope is connected to the endoscope;

FIG. 30 is a flowchart describing the processing for treating cleaning-related information when a cleaning apparatus having the ability to communicate with the endoscope is connected to the endoscope;

FIG. 31 is a flowchart describing the processing to be performed in a connected apparatus for writing user-related data;

FIG. 32 is an example of displaying the user-related data;

FIG. 33 is a flowchart describing the processing to be performed in a connected apparatus for executing write enabling;

FIG. 34 is a circuit diagram showing an example of the circuitry of a selector 74;

FIG. 35 is a flowchart describing the processing to be performed in a connected apparatus for executing counting;

FIG. 36 is a flowchart describing the processing to be performed in a connected apparatus for reading or writing a previous examination time instant;

FIG. 37 shows an example of the displaying of data on the monitor;

FIG. 40 shows a table listing the items of endoscope-related data written in a nonvolatile memory;

FIG. 46 shows a table listing the functions of keys and LEDs arranged in a switch section;

FIG. 47 shows a Scope Information form displayed on a screen during reading of endoscope-related data;

FIG. 48 shows an example of the Scope Information form;

FIG. 53 shows a table listing the endoscope-related data to be displayed in the Scope Information form on the screen;

DESCRIPTION OF THE PREFERRED EMBODIMENTS

First Embodiment

The first embodiment of the present invention will be described with reference to FIG. 1 to FIG. 37.

Figure 1:
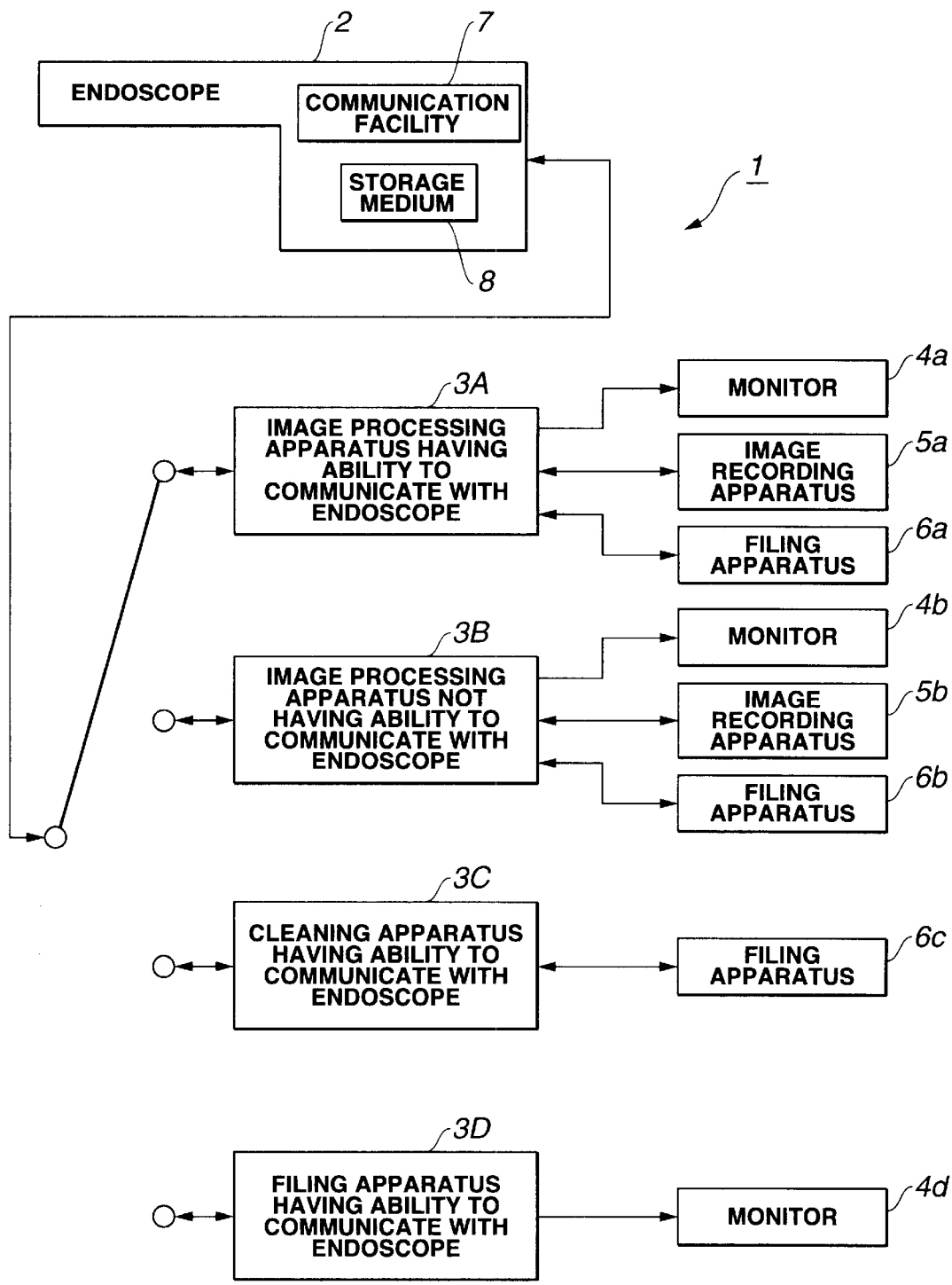

An endoscope system 1 in accordance with the first embodiment of the present invention shown in FIG. 1 consists broadly of an endoscope 2, and connected apparatuses (or peripheral equipment) to be selectively connected to the endoscope. The connected apparatuses include an image processing apparatus 3A, an image processing apparatus 3B, a cleaning apparatus 3C, a filing apparatus 3D, a monitor 4a, an image recording apparatus 5a, a filing apparatus 6a, a monitor 4b, an image recording apparatus 5b, a filing apparatus 6b, a filing apparatus 6c, and a monitor 4d. The image processing apparatus 3A has the ability to communicate with the endoscope 2, while the image processing apparatus 3B does not have the ability to communicate with the endoscope 2. The cleaning apparatus 3C has the ability to communicate with the endoscope 2. The filing apparatus 3D has the ability to communicate with the endoscope 2. The monitor 4a, image recording apparatus 5a, and filing apparatus 6a are connected to the image processing apparatus 3A. The monitor 4b, image recording apparatus 5b, and filing apparatus 6b are connected to the image processing apparatus 3B. The filing apparatus 6c is connected to the cleaning apparatus 3C. The monitor 4d is connected to the filing apparatus 3D.

The endoscope 2 has a communication facility (communication unit) 7 responsible for communications and a storage medium 8 that is a programmable memory in which information is stored. The communication facility 7 includes a serial interface means as described later. The inclusion of these components contributes to a decrease in the number of signal lines over which a signal is transmitted, and a decrease in the number of connector pins used for connection. Consequently, the endoscope 2 is designed to be lightweight and compact to ensure excellent maneuverability.

For example, when an endoscopic imaging system is constructed by connecting the image processing apparatus 3A having communication capability to the endoscope 2, an endoscopic image produced by the endoscope 2 is processed by the image processing apparatus 3A and displayed on the monitor 4a. Thus, an intracorporeal region of a subject can be examined through endoscopic observation. Moreover, the endoscopic image can be recorded using the image recording apparatus 5a (printer or video tape recorder). In addition, the filing apparatus 6a may be used to record, read, or manage endoscopic images or endoscope-related data.

Moreover, endoscope-related data stored in the storage medium in the endoscope 2 is processed in response to a Read command, a Write command, or any other command through communication with the endoscope 2 (which will be detailed later).

In contrast, when an endoscopic imaging system is constructed by connecting the image processing apparatus 3B to the endoscope 2, an endoscopic image produced by the endoscope 2 is processed by the image processing apparatus 3B, displayed on the monitor 4b, and recorded using the image recording apparatus 5b (printer or video tape recorder). The filing apparatus 6b may be used to record, read, or manage endoscopic images or endoscope-related data. However, since the image processing apparatus 3B does not have the ability to communicate with the endoscope 2, communication is not carried out.

When the cleaning apparatus 3C is connected to the endoscope 2, the cleaning apparatus 3C communicates with the endoscope 2 and cleans it. Moreover, the filing apparatus 6c may be used to record, read, or manage endoscope-related data.

Moreover, when the filing apparatus 3D is connected to the endoscope 2, the filing apparatus 3D communicates with the endoscope 2. The filing apparatus 3D thus treats endoscope-related data stored in the storage medium in the endoscope 2 in response to a Read command, a Write command, or any other command. Moreover, the filing apparatus 3D manages endoscope-related data concerning a plurality of endoscopes 2 and displays endoscope-related data on the monitor 4d.

In the present embodiment, filing apparatuses are included in association with connected apparatuses. In addition, one filing apparatus is connectable to a plurality of connected apparatuses (3A, 3B, and 3C) over, for example, a network. The filing apparatus may be used to record or manage information concerning the plurality of endoscopes 2 on a centralized basis. Moreover, the filing apparatuses 6a, 6b, and 6c may be interconnected over, for example, a network so that they can read, write, and mange endoscope-related data allocated to them.

Figure 2:
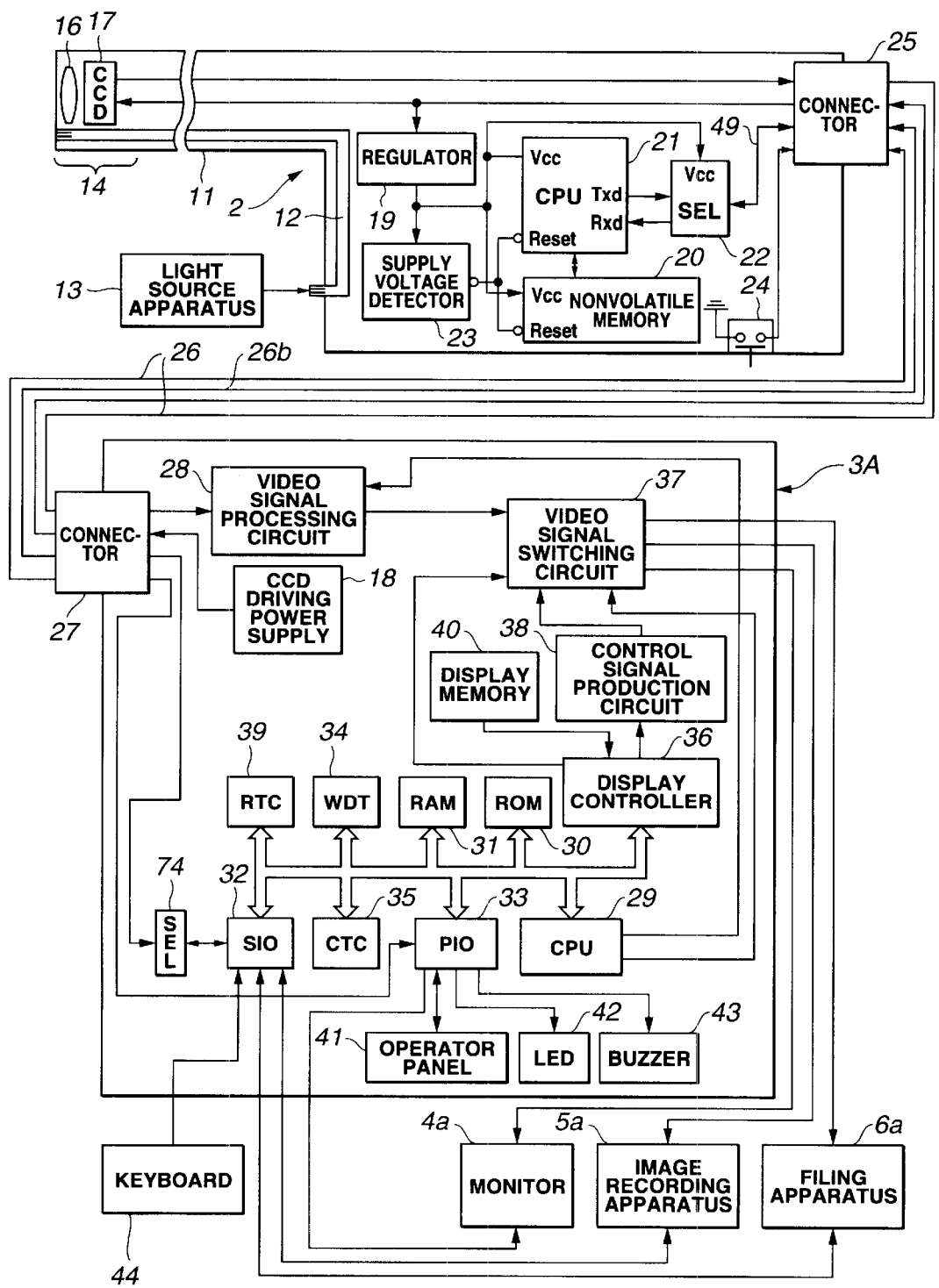

FIG. 2 is a block diagram showing in detail the endoscope 2 and the image processing apparatus 3A having the communicating ability which are employed in the present embodiment.

The endoscope 2 is an electronic endoscope and has an elongated insertion unit 11 to be inserted into a subject. A light guide 12 is passed through the insertion unit 11. The rear end of the light guide 12 is coupled to a light source apparatus 13 so that it can be uncoupled freely. The light guide 12 propagates illumination light emanating from a lamp incorporated in the light source apparatus 13. The illumination light is emitted forwards from the distal end of the light guide locked in an illumination window formed on a distal part 14 of the insertion unit 11. An object such as a lesion in the subject is thus illuminated.

The illuminated object is imaged by a solid-state imaging device located on an image plane, for example, a charge-coupled device (CCD) 17 through an objective 16 locked in an observation window formed in the distal part 14. The CCD 17 photoelectrically converts the optical image.

A regulator 19, a programmable nonvolatile memory 20, a CPU 21, a selector (SEL) 22, a supply voltage detector 23, a scope switch 24, and a connector 25 are arranged behind the rear end of the insertion unit 11 of the endoscope 2. The regulator 19 converts a CCD driving voltage fed from a CCD driving power supply 18 incorporated in the image processing apparatus 3A into a desired voltage. The programmable nonvolatile memory 20 in which the endoscope-related data is stored is realized with an EEPROM, a flash ROM, an FRAM, or an MRAM. The CPU 21 includes a one-chip microcomputer for performing a plurality of arithmetic operations including communication and writing, or reading. Specifically, the CPU 21 transmits or receives the endoscope-related data to or from the image processing apparatus 3A through a serial interface, and writes or reads the endoscope-related data in or from the nonvolatile memory 20. The CPU 21 includes a ROM, a RAM, a watchdog timer (WDT), a serial controller (S10), a parallel controller (P10), and a counter (CTC). The selector 22 acts as a serial interface means for transmitting or receiving the endoscope-related data over a sole signal line 49. The supply voltage detector 23 detects a fluctuation or drop in supply voltage and outputs a reset signal, thus preventing a malfunction of the CPU 21 or the nonvolatile memory 20.

The connector 25 of the endoscope 2 is linked to a connector 27 of the image processing apparatus 3A by a cable 26.

The image processing apparatus 3A consists broadly of a CCD driving power supply 18, a video signal processing circuit 28, a CPU 29, a ROM 30, a RAM 31, a serial controller (S10) 32, a parallel communication controller (PIO) 33, a watchdog timer (WDT) 34, a counter timer (CTC) 35, a display controller 36, a display memory 40, a video signal switching circuit 37, a control signal production circuit 38, a real-time clock (RTC) 39, an operator panel 41, an LED 42, a buzzer 43, and a light adjustment control unit. The CCD driving power supply 18 applies a voltage to the CCD 17 in the endoscope 2. The video signal processing circuit 28 processes a video signal resulting from photoelectric conversion performed by the CCD 17. The CPU 29 carries out a plurality of arithmetic operations. The ROM 30, which may include an EEPROM or a flash ROM, is a programmable memory in which programs according to which the CPU 29 acts, and endoscope-related data transmitted in the form of serial data from the endoscope 2 are stored. The RAM 31 serves as an arithmetic memory or a memory in which the endoscope-related data transmitted in the form of serial data is temporarily stored. The serial controller (S10) 32 converts the endoscope-related data into a serial data structure so that the endoscope-related data can be communicated to the endoscope 2 through a serial interface. The watchdog timer (WDT) 34 prevents an abnormal run of the CPU 29. The display controller 36 controls the display of an endoscopic image processed by the video signal processing circuit 28, patient data, a date, a comment, and other endoscope-related data. The display memory 40 serves as a display controller memory. The video signal switching circuit 37 switches or synthesizes an endoscopic image output from the video signal processing circuit 28, and the display data including patient data, a date, a comment, and other endoscope-related data output from the display controller 36. The control signal production circuit 38 controls switching to be performed by the video signal switching circuit 37. The real-time clock 39 indicates a current date. The operator panel 41 is used to operate the image processing apparatus 3A. The light adjustment control unit adjusts light emanating from the light source apparatus 13. The serial controller 32 is connected to a keyboard 44 used to enter the endoscope-related data.

The operator panel 41, LED 42, and buzzer 43 are connected to the parallel controller 33.

An output of the video signal switching circuit 37 is displayed on the monitor 4a. The image recording apparatus 5a or filing apparatus 6a is used to record, read, or manage endoscopic images. The CPU 29 controls the monitor 4a, image recording apparatus 5a, and filing apparatus 6a via the serial controller 32 or parallel controller 33. Moreover, the CPU 29 reads, writes, or manages endoscope-related data.

A serial interface included in the serial controller 32 for interfacing the keyboard 44, image processing apparatus 5a, and the filing apparatus 6a is conformable to the standard PS/2, USB, IEEE1394, or Ethernet.

The image processing apparatus 3B shown in FIG. 1 includes all the components of the image processing apparatus 3A shown in FIG. 2 except components for communicating with the endoscope 2 through a serial interface. The components of the cleaning apparatus 3C are identical to those of the image processing apparatus 3A but do not include the video signal processing circuit 28 and other components involved in video signal processing. The cleaning apparatus 3C includes an endoscope cleaning unit that is not shown.

The filing apparatus 3D includes all the components of the image processing apparatus 3A except the video signal processing circuit 28 and other components involved in video signal processing.

FIG. 3 is a block diagram showing an example of the circuitry of the selector 22 shown in FIG. 2.

The selector 22 includes a buffer 48 and an open-collector or open-drain device 47 that is connected to a power supply terminal Vcc via a resistor 46 to have the output thereof pulled up. A transmission signal (Txd) sent from the CPU 21 is input to the image processing apparatus 3A through the connector 25 via the open-collector or open-drain device 47 over the sole signal line 49.

The CPU 21 controls the serial controller in the CPU 21 to disable reception of a signal Rxd, and then transmits the signal Txd. The transmission signal sent from the CPU 21 will therefore not be received by the CPU 21 through a receiving terminal Rxd. The reception signal (Rxd) received by the CPU 21 via the buffer 48 is sent from the image processing apparatus 3A through the connector 25 over the signal line 49.

The selector 22 serves as a communicating means for placing an output voltage at a high level, thus permitting transmission and reception over the sole signal line 49 and allowing signals to be communicated bi-directionally between the CPU 21 in the endoscope 2 and the image processing apparatus 3A. The signal line 49 is spliced with a sole signal line 26b that is contained in a cable 26 for linking the connector 25 of the endoscope 2 and the connector 27 of the image processing apparatus 3A. Moreover, the signal line 26b is spliced with a sole signal line, which is routed to a selector 74 shown in FIG. 2, inside the connector 27.

Figure 34:
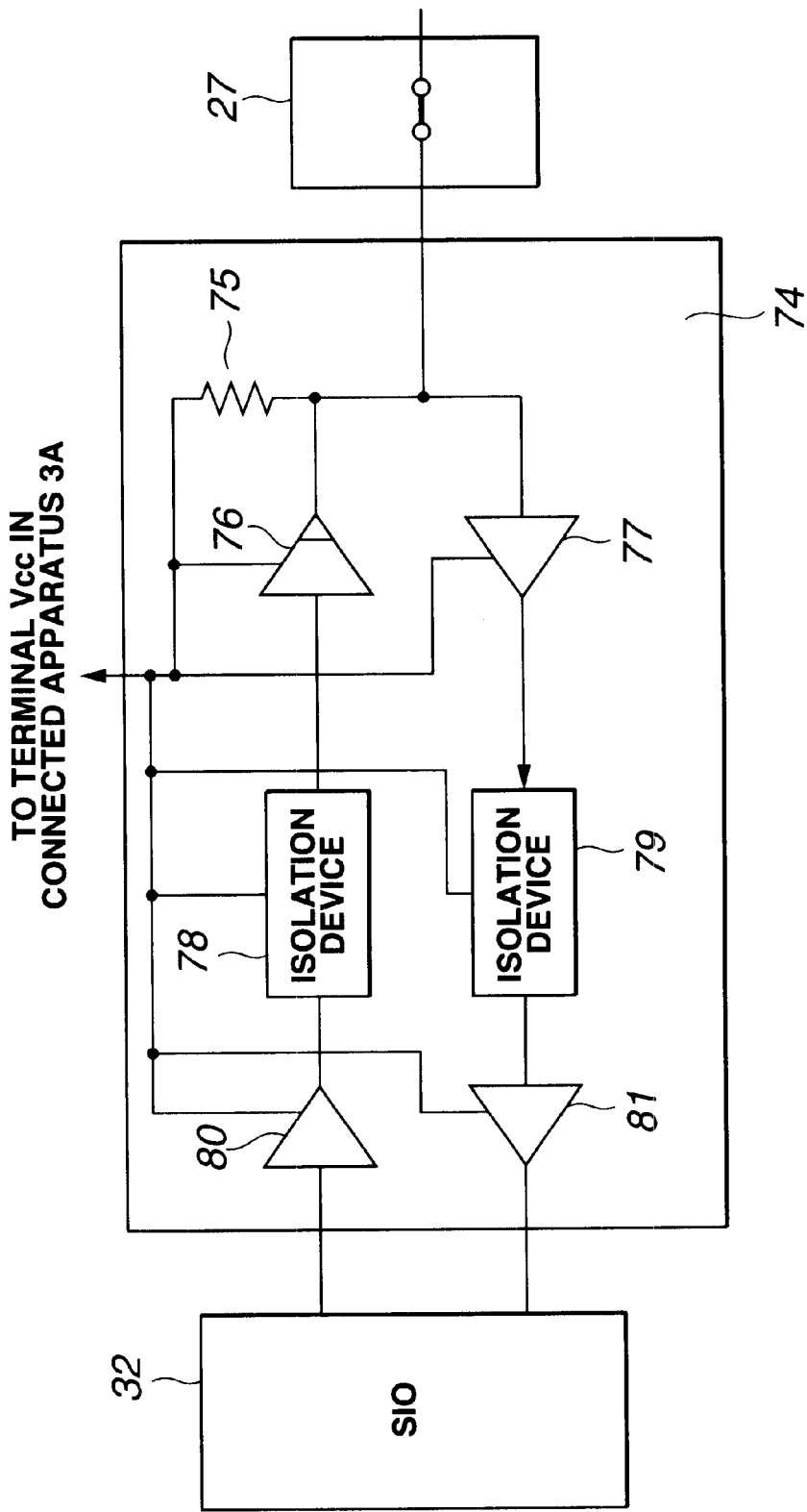

FIG. 34 is a block diagram showing an example of the circuitry of the selector 74 shown in FIG. 2.

The selector 74 includes an open-collector or open-drain device 76, buffers 70, 80, and 81, and isolation devices 78 and 79. The open-collector or open-drain device 76 is connected to a power supply terminal Vcc (not shown) of a connected apparatus 3A via a resistor 75 to have the output thereof pulled up. The isolation devices 78 and 79 are realized with photocouplers or transformers for the purpose of electrical isolation. A signal sent from the endoscope 2 is input to the serial controller 32 by the connector 27, buffer 77, isolation device 79, and buffer 81, and processed as a reception signal by the CPU 29. A signal sent from the serial controller 32 is received by the endoscope 2 by the buffer 80, isolation device 78, open-collector or open-drain device 76, and connector 27.

Before the serial controller 32 transmits a transmission signal, the CPU 29 controls the serial controller 32 to disable reception. A transmission signal sent from the CPU 29 is sent from the serial controller 32, passed through the buffer 80, isolation device 78, and open-collector or open-drain device 76, and then received by the serial controller 32 by the buffer 77, isolation device 79, and buffer 81. At this time, the transmission signal will not be received by the endoscope 2.

The selector 74 fills the role of a communicating means for placing, similarly to the selector 22, an output voltage at a high level so as to permit transmission and reception over the sole signal line, and for transmitting and receiving signals bi-directionally. Moreover, the selector 74 contributes to electrical isolation.

As mentioned above, the endoscope 2 has the selector 22 serving as a serial interface means for permitting bi-directional data communication over a sole communication line. The selector 22 thus fills the role of a communicating means allowing the endoscope 2 to communicate with a peripheral equipment (including the image processing apparatus 3A) having the communicating ability (pieces of peripheral equipment connected to the endoscope 2 are referred to as connected apparatuses). This leads to a decrease in the number of cables 26 linking the endoscope 2 and a connected apparatus. Consequently, the endoscope 2 becomes more flexible and an operator will not be bothered with cables while manipulating the endoscope. Moreover, a connector having a small number of connector pins can be adopted as the connector 25 of the endoscope 2. This results in a user-friendly endoscope.

Moreover, a small connector having a small number of connector pins can be adopted as the connector 27 of a connected apparatus.

Since the communicating means is designed to permit serial data communication, the cost of the communicating means can be low.

The endoscope 2 has the CCD 17 serving as a solid-state imaging device. The regulator 19 is included in a power supply unit for feeding power to the storage medium 7 incorporated in the endoscope 2 as shown in FIG. 1 (nonvolatile memory 20 included therein as shown in FIG. 2) and the communication unit 8 shown in FIG. 1 (selector 22 and CPU 21 included therein as shown in FIG. 2). The power supply unit including the regulator 19 also feeds power to the CCD 17.

The power supply unit for feeding power to the storage medium 7 and the communication unit (facility) 8 in the endoscope 2 is used in common as the power supply for feeding power to the CCD 17 which is the solid-state imaging device. This leads to a reduction in the size of a connector through which the endoscope 2 is connected to a connected apparatus. Thus, the user-friendly endoscope 2 is realized.

The endoscope 2 and the connected apparatus may communicate with each other over, as shown in FIG. 2 and FIG. 3, the sole signal line 49. Alternatively, two signal lines may be used for the transmission signal and reception signal respectively.

FIG. 4A shows a data structure for the communication data between the endoscope 2 and the connected apparatus 3A, 3C, or 3D. FIG. 4B describes the items of the data structure.

The endoscope 2 and connected apparatus 3A, 3C, or 3D communicate with each other over the sole signal line 49. The communication is therefore asynchronous.

In this case, as shown in FIG. 4A, data is transmitted in units of a block 51. One block 51 consists of a plurality of items STX 52, LEN 53, DATA 54, \LEN 55, \DATA 56, CS 57, and ETX 58. Each item is eight bits long. For transmission or reception, a start bit, a stop bit, and a parity bit are appended to the eight bits.

The items of the data structure are described in FIG. 4B.

\LEN 55 and \DATA 56 specify the reversals of LEN 53 specifying a data length and DATA 54. By comparing LEN with \LEN or DATA with \DATA, it can be checked whether the data of the block 51 has been transmitted or-received correctly.

CS 57 specifies a checksum of data items specified for STX 52 to \DATA 56. The checksum is used to check if the data has been transmitted or received correctly.

(\LEN 53, \LEN 55, DATA 4, \DATA 56, CS 57, and parity bits appended thereto shall be referred to as check data.)

DATA 54 may specify data coded according to the ASCII or JIS code. Alternatively, an original code may be used so that data coded according to the original code will not be interpreted easily. In this case, the endoscope-related data stored in the nonvolatile memory 20, the ROM in the CPU 21, the ROM 30, or the RAM 31 according to the ASCII or JIS code is converted according to the original code using a code conversion table stored in the ROM in the CPU 21 or the ROM 30. The resultant data is then transmitted. Received data that has been coded according to the original code is re-converted according to the ASCII or JIS code, and then the received data is processed.

Moreover, code conversion and code re-conversion to be performed for communication may involve date specified for all the items shown in FIG. 4A except those specified for STX and ETX.

Figure 5:
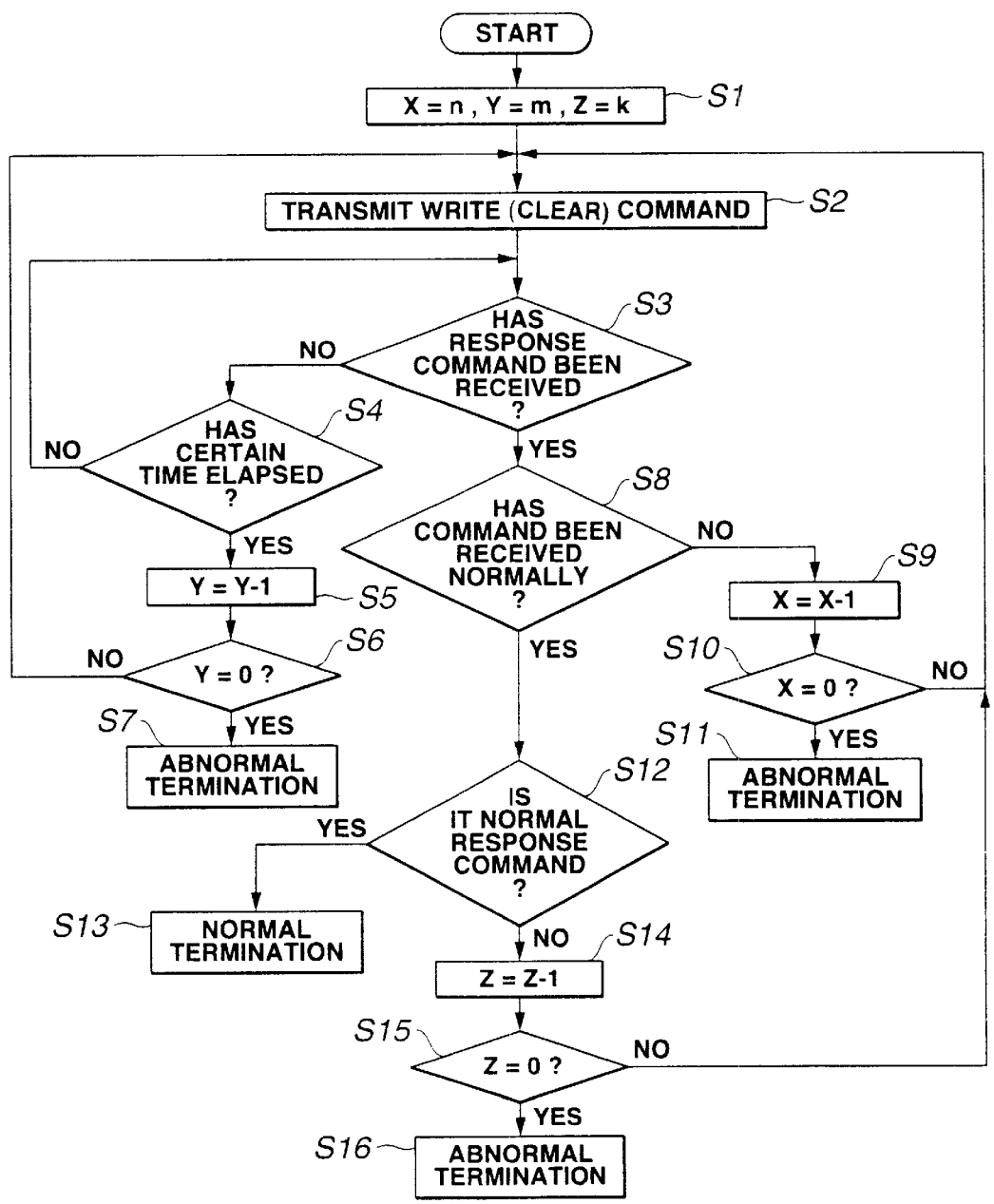
Figure 6:
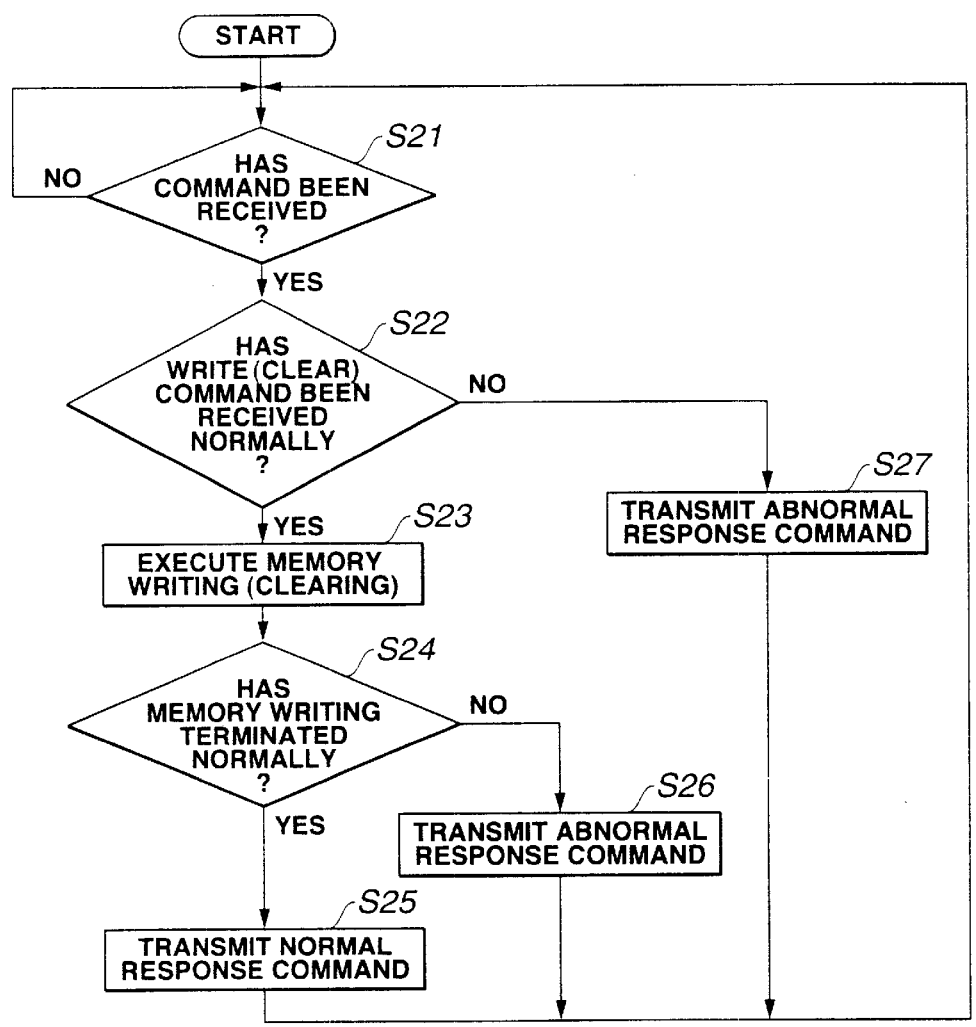

FIG. 5 is a flowchart describing the steps to be performed in a connected apparatus for writing or clearing the endoscope-related data in or from the nonvolatile memory 20 in the endoscope. FIG. 6 is a flowchart describing the steps to be performed in the endoscope for allowing the connected apparatus to write or clear the endoscope-related data in or from the nonvolatile memory 20 in the endoscope.

First, at step S1 in FIG. 5, a connected apparatus sets the numbers of transmissions X, Y, and Z, by which a Write command is transmitted, to n, m, and k respectively. X denotes the number of retransmissions by which the transmission is retried when the connected apparatus fails to normally receive a response command from the endoscope 2. Y denotes the number of retransmissions by which the transmission is retried when no response command has been received within a certain time (for example, 30 sec) after the Write command is transmitted from the connected apparatus. Z denotes the number of the retransmissions by which the transmission is retried when a response command is not received normally.

Thereafter, the connected apparatus transmits the Write command or a Clear command to the endoscope 2 (S2), and waits until a response command is sent from the endoscope 2 (S3). The Write command is transmitted in the form of the block 51 shown in FIG. 4 and has a Write instruction and endoscope-related data to be actually written specified for DATA 54. The clear command has a Clear instruction specified for DATA 54.

The Write (Clear) command is transmitted from the CPU 29 in the connected apparatus to the endoscope 2 via the serial controller 32 and selector 74 through the connector 27 over the signal cable 26. The Write (Clear) command is then received by the CPU 21 in the endoscope 2 via the selector 22 through the connector 25.

The endoscope 2 waits, as described in FIG. 6, until a command is sent from the connected apparatus (S21). After the Write command or Clear command is received, check data contained in the command is analyzed in order to check whether the data has been received normally (S22). If it is confirmed that the data has been received normally, the memory writing of step S23 for writing the endoscope-related data specified for DATA 54 in the nonvolatile memory 20 or the memory clearing for clearing data in the nonvolatile memory 20 is executed (to be detailed in FIG. 8).

After the memory writing or the memory clearing is executed, it is checked at step S24 whether the memory writing or the memory clearing has terminated normally. If it has terminated normally (S36 in FIG. 8), a normal response command is transmitted to the connected apparatus (S25). Control is then returned to step S21, and the next command is awaited.

If the memory writing or the memory clearing of step S24 has not terminated normally (S33 in FIG. 8), an abnormal response command is transmitted to the connected apparatus (S26). If the Write command has not been received normally at step S22, the abnormally response command is transmitted to the connected apparatus (S27). Control is then returned to step S21, and the next command is awaited.

The same abnormal response command may be transmitted at step S26 and step S27 respectively. Alternatively, different commands specifying a kind of abnormality may be transmitted at step S26 and step S27 respectively, so that a cause of an abnormality occurring in the endoscope 2 can be detected.

Each response command is transmitted from the CPU 21 to the connected apparatus via the selector 22 through the connector 25 over the cable 26, and then input to the CPU 29 via the selector 74 and the serial controller 32 through the connector 27.

The connected apparatus transmits the Write command or the Clear command at step S2 in FIG. 5, and waits for a response command at step S3. It is judged whether a response command has been received within a certain time (S4). If so, the number of retransmissions Y is decremented by one (Y−1) (S5). It is then judged whether the number of retransmissions Y is 0 (S6). If the number of retransmissions Y is not 0, control is returned to step S2. The Write command or the Clear command is retransmitted. When the number of retransmissions Y equals 0, it is judged that transmission has been retried m times. The processing is then suspended and terminated abnormally (S7).

In contrast, after the connected apparatus transmits the Write command or the Clear command at step S2, if the connected apparatus receives a response command from the endoscope 2 at step S3 of waiting for a response command, control is passed to step S8. It is then checked if the response command has been received normally.

Specifically, check data contained in the received command is checked to see if the command has been received normally. If the response command has not been received normally, the number of retransmissions X is decremented by one (X−1) (S9). It is then judged whether the number of retransmissions X is 0 (S10). If the number of retransmissions X is not 0, control is returned to step S2. The Write command or the Clear command is retransmitted. When the number of retransmissions equals 0, it is judged that transmission has been retried n times. The processing is then suspended and terminated abnormally (S11).

If it is judged at step S8 that the command has been received normally, it is judged at step S12 whether the command is a normal response command. If the command is a normal response command, the processing of writing or clearing is terminated normally (S13).

If it is judged that the command is not a normal response command (an abnormal response command), the number of retransmissions Z is decremented by one (Z−1) (S14). It is then judged whether the number of retransmissions Z is 0 (S15). If the number of retransmissions Z is not 0, control is returned to step S2. The Write command or the Clear command is then retransmitted. When z equals 0, it is judged that transmission has been retried k times. The processing is then suspended and terminated abnormally (S16).

The numbers of retransmissions X, Y, and Z may be set (S1) at every execution of writing or clearing as described in the flowchart of FIG. 5. Alternatively, the numbers of retransmissions may be pre-set and stored in the ROM 30 or RAM 31 in the connected apparatus in order to obviate the necessity of the setting.

Next, writing or memory clearing of step S23 in FIG. 6 will be described.

A storage area in the nonvolatile memory 20 included in the endoscope 2 in which each of a plurality of the endoscope-related data items is stored consists, as shown in FIG. 7A, of a data division 60 and a backup data division 61 for backing up the data division 60. The data division 60 or the backup data division 61 consists of a write flag area 62 or 65, a data area 63 or 66, and a checksum area 64 or 67. What are stored in the areas are described in FIG. 7B.

The backup data division 61 may be allocated to all endoscope-related data items to be stored in the nonvolatile memory 20. Alternatively, the backup data division 61 may be allocated to especially important data (for example, an endoscope model name, the structure of the distal part of an endoscope, a cleaning tube/adaptor name, a CCD model name, a type of optical filter in a CCD, information of channels in an endoscope, information of switches in an endoscope, identification data, count data, the circuitry of a reprocessing circuit, a previous examination time instant, and a serial number).

Figure 8:
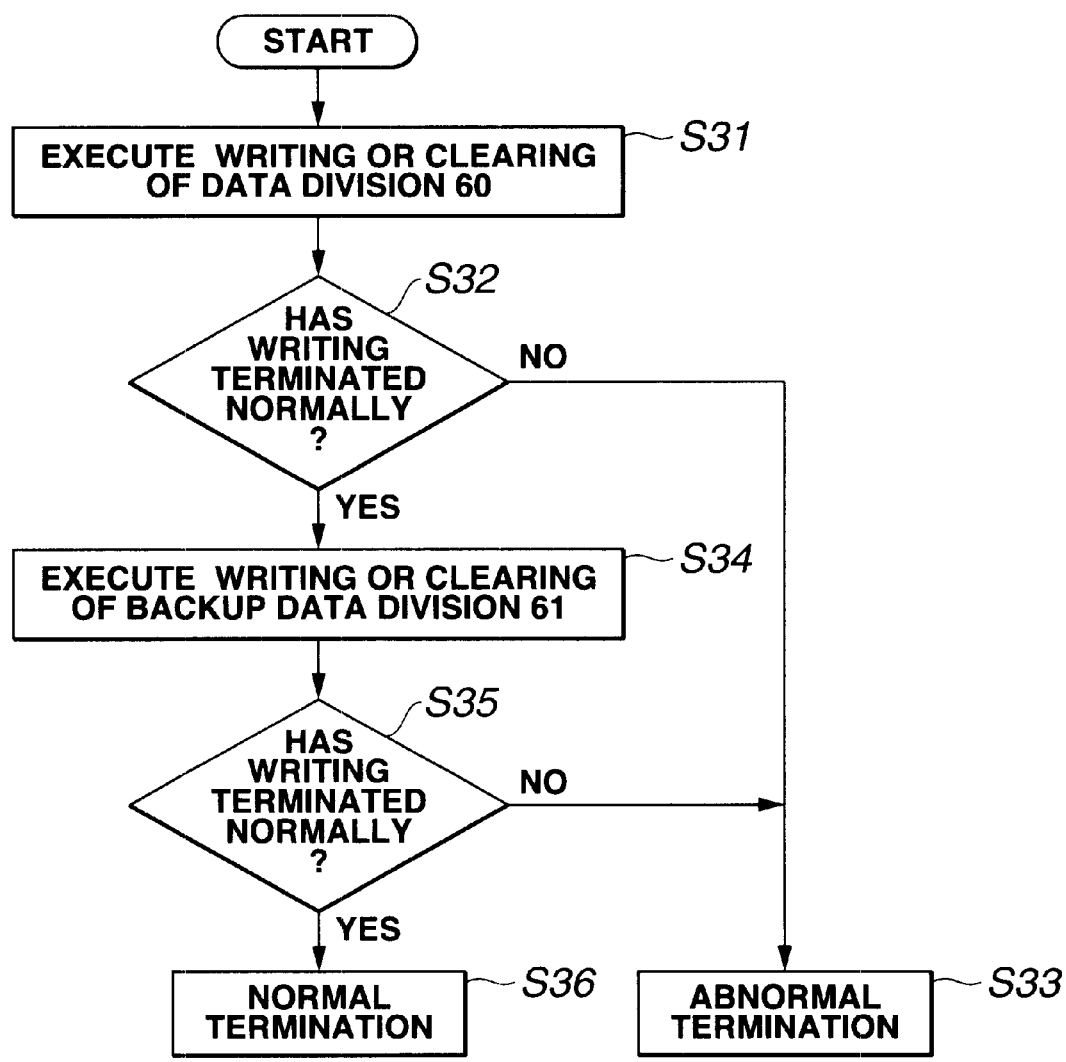

FIG. 8 is a flowchart describing the steps performed in the endoscope 2 for performing memory writing or memory clearing at step S23 in FIG. 6.

To begin, writing or clearing the data division 60 shown in FIG. 7 is executed at step S31 in FIG. 8. It is then determined (step S32) whether the writing or clearing has terminated normally.

Figure 9:
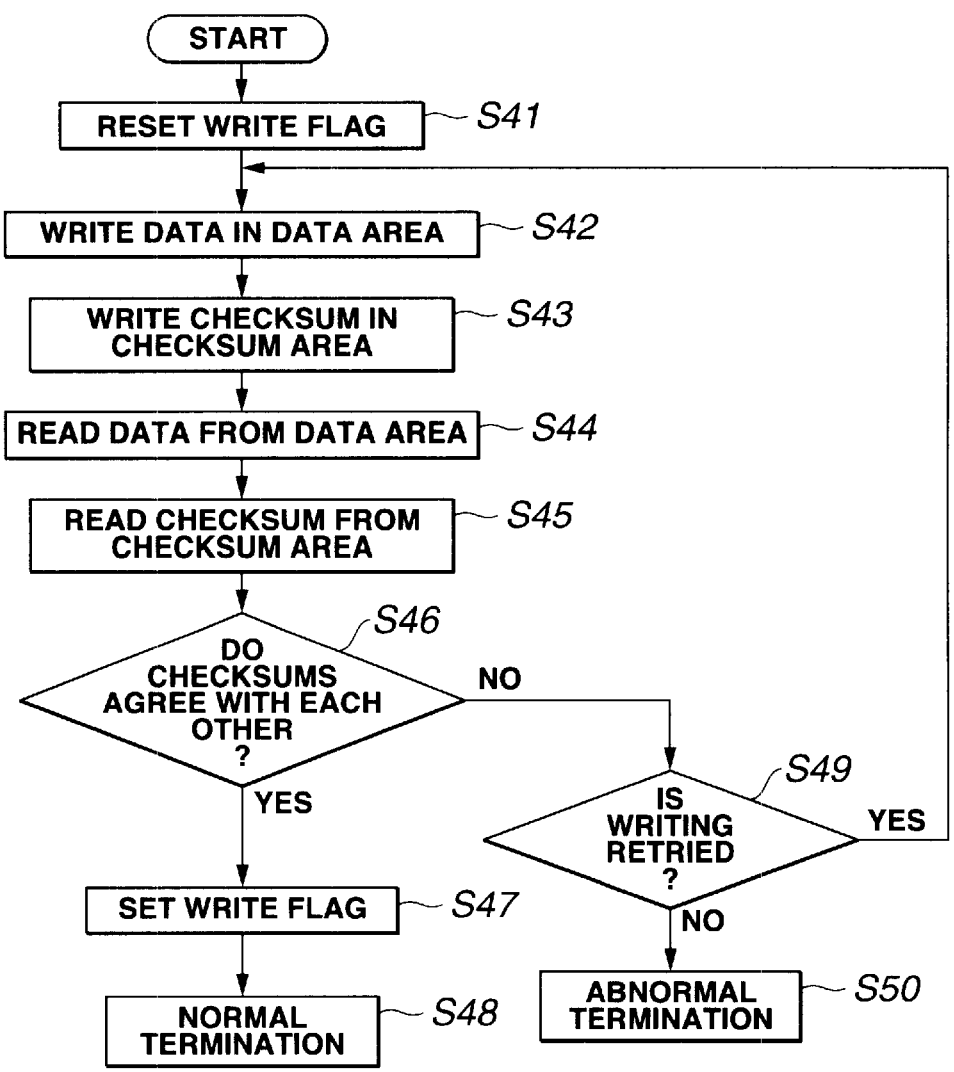

Writing the data division is performed according to a procedure described in FIG. 9.

Specifically, at step S41 in FIG. 9, the data write flag area 62 is cleared (to, for example, 00h).

At step S42, endoscope-related data contained in a Write command is written in the data area 63 (when writing is executed). Otherwise, clear data that is a pre-set value in the ROM included in the CPU 21 in the endoscope 2 is written therein (when clearing is executed).

Thereafter, a checksum of the data written at step S42 is written in the data checksum area 64.

The data written in the data area 63 during writing of step S42 is read (S44).

The checksum written in the data checksum area 64 at step S43 is read (S45).

At step S46, it is checked whether a checksum calculated from the data read at step S44 agrees with the checksum read at step S45.

If the checksums agree with each other, it is concluded that the data has been written correctly. The flag stored in the data write flag area 62 is set (to, for example, 01h) at step S47. The processing is then terminated normally (S48).

If it is determined at step S46 that the checksums disagree with each other, it is judged that the data has not been written correctly. It is concluded at step S49 whether writing is retried. If writing is not retried even once, control is returned to step S42. Writing data is retried once.

After writing data is retried, if it is concluded at step S46 that the checksums still disagree with each other, the processing is terminated abnormally (S50).

If it is determined at step S32 in FIG. 8 that writing or clearing the data division 60 has not terminated normally, the writing or clearing is terminated abnormally (step S50) and memory writing or memory clearing is terminated abnormally (step S33). If writing the data division 60 has terminated normally (S48), writing or clearing the backup data division 61 is executed at step S34. Thereafter, it is checked at step S35 whether the writing or clearing has terminated normally.

Figure 10:
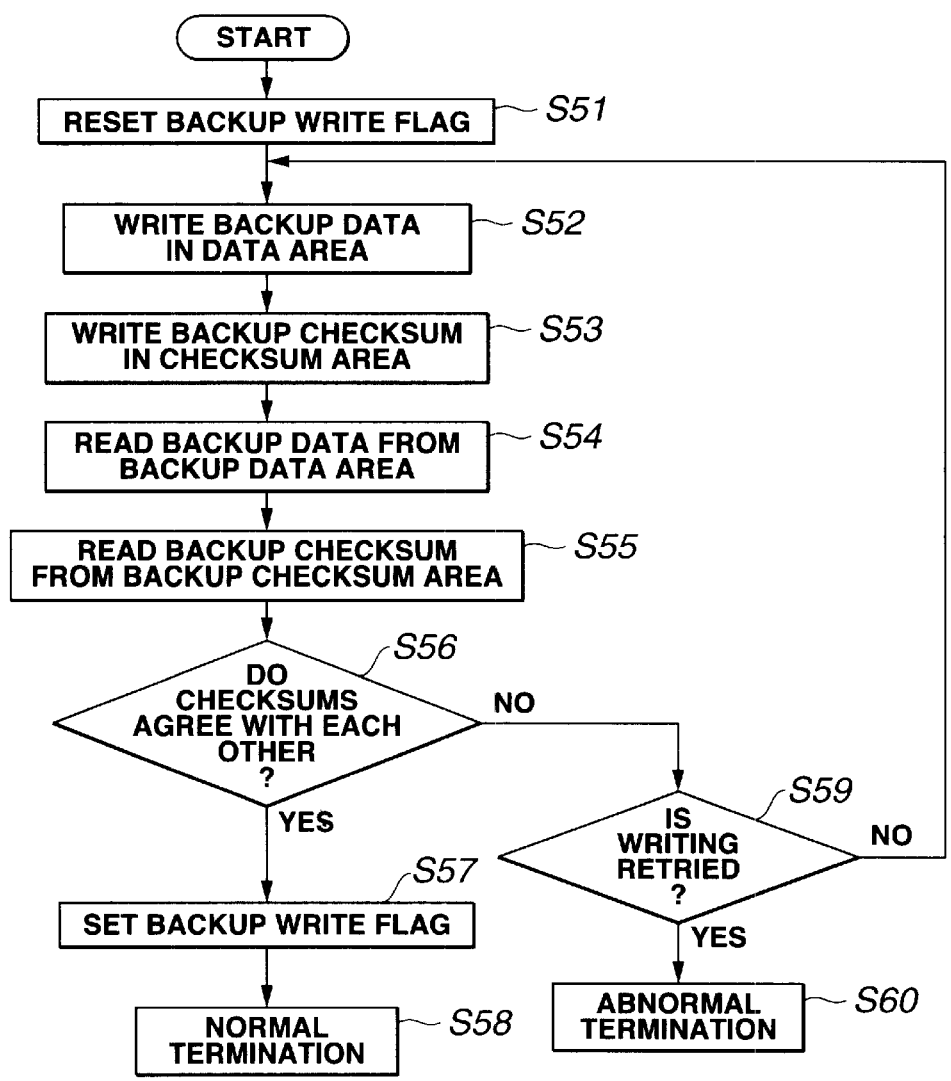

Writing the backup data division 61 is performed according to a procedure described in FIG. 10.

Specifically, at step S51 in FIG. 10, the flag stored in the backup data write flag area 65 is reset (to, for example, 00h).

At step S52, endoscope-related data contained in a received Write command is written in the backup data area 66 (when writing is executed). Otherwise, clear data that is a pre-set value in the endoscope 2 is written therein (when clearing is executed).

Thereafter, a checksum of the data written at step S52 is written in the backup data checksum area 67.

The data written in the backup data area 66 during writing of step S52 is read (S54).

The checksum written in the backup data checksum area 67 at step S53 is read (S55).

At step S56, it is checked whether a checksum calculated from the data read at step S54 agrees with the checksum read at step S55.

If the checksums agree with each other, it is concluded that the data has been written correctly. The flag stored in the backup data write flag area 65 is set (to, for example, 01h) at step S57. The processing is then terminated normally (S58).

If it is determined at step S56 that the checksums disagree with each other, it is judged that the data has not been written correctly. It is then determined at step S59 whether writing is retried. If writing is not retried even once, control is returned to step S52. Writing is then retried once.

After writing is retried, if it is found at step S56 that the checksums still disagree with each other, the processing is terminated abnormally (S60).

As mentioned above, writing or clearing the backup data division 61 is executed at step S34 in FIG. 8. It is determined at step S35 whether the writing or clearing has terminated normally. If writing or clearing the backup data division 61 is terminated normally (S58), memory writing or memory clearing is terminated normally (S36). If writing or clearing the backup data division 61 is not terminated normally (S60), memory writing or memory clearing is terminated abnormally (S33).

When writing data in the data area 63 or backup data area 66 is in progress, the flag area 62 or 65 is cleared. In this state, if a power failure occurs or if the power supply of the endoscope 2 is turned off in order to disconnect the endoscope 2 from the connected apparatus, the flag stored in the flag area 62 or 65 remains reset.

The checksum written in the checksum area 64 or 67 is used to check as described in FIG. 9 or FIG. 10 if the data stored in the data area 63 or 66 is correct.

The checksum stored in the checksum area 64 or 67 may be appended to a normal response command to be transmitted at step S25 in FIG. 6. The connected apparatus may compare the checksum appended to the response command received at step S12 in FIG. 5 with a checksum calculated from endoscope-related data contained in the Write command transmitted at step S2. It may thus be checked if the endoscope-related data has been correctly written in the memory 20 in the endoscope 2.

Figure 11:
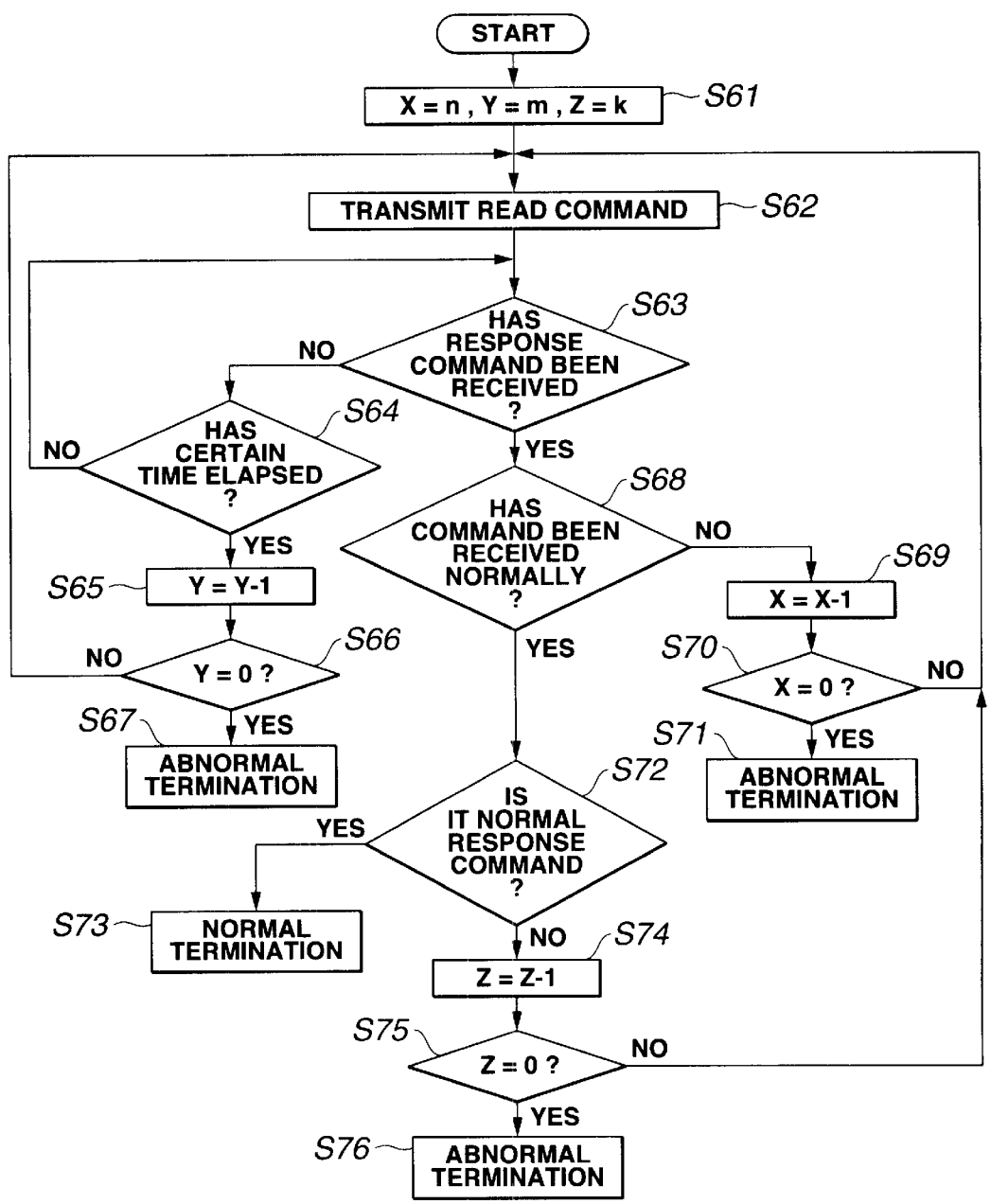
Figure 12:
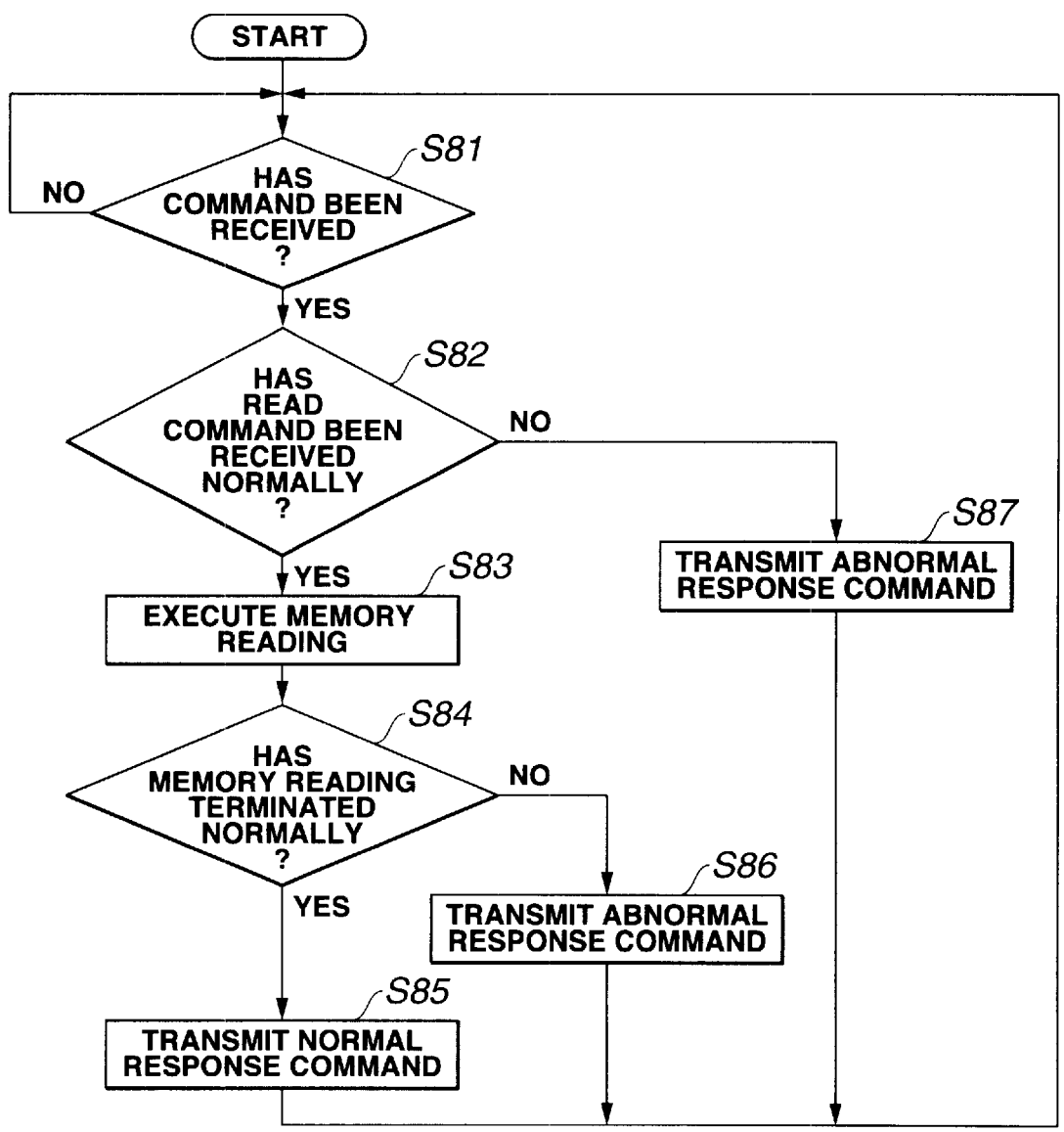

FIG. 11 is a flowchart describing actions to be performed in a connected apparatus for reading endoscope-related data from the nonvolatile memory 20 in the endoscope 2. FIG. 12 is a flowchart describing actions to be performed in the endoscope for allowing the connected apparatus to read endoscope-related data from the nonvolatile memory 20 in the endoscope 2.

First, at step S61 in FIG. 11, the connected apparatus sets the numbers of retransmissions X, Y, and Z, by which a Read command is transmitted, to n, m, and k respectively. X denotes the number of retransmissions by which transmission is retried when the connected apparatus fails to normally receive a response command. Y denotes the number of retransmissions by which transmission is retried when no response command is received within a certain time (for example, 3 seconds) after the Read command is transmitted from the connected apparatus. Z denotes the number of retransmissions by which transmission is retried when a normal response command is not received.

A Read command is transmitted to the endoscope 2 in the form of the block 51 shown in FIG. 4 with a Read instruction specified for DATA 54 (S62). Thereafter, a response command is awaited (S63).

To be more specific, the Read command is transmitted from the CPU 29 in the connected apparatus to the endoscope 2 via the serial controller 32 through the connector 27 over the cable 26. The CPU 21 in the endoscope 2 receives the Read command via the selector 22 through the connector 25.

Figure 13:
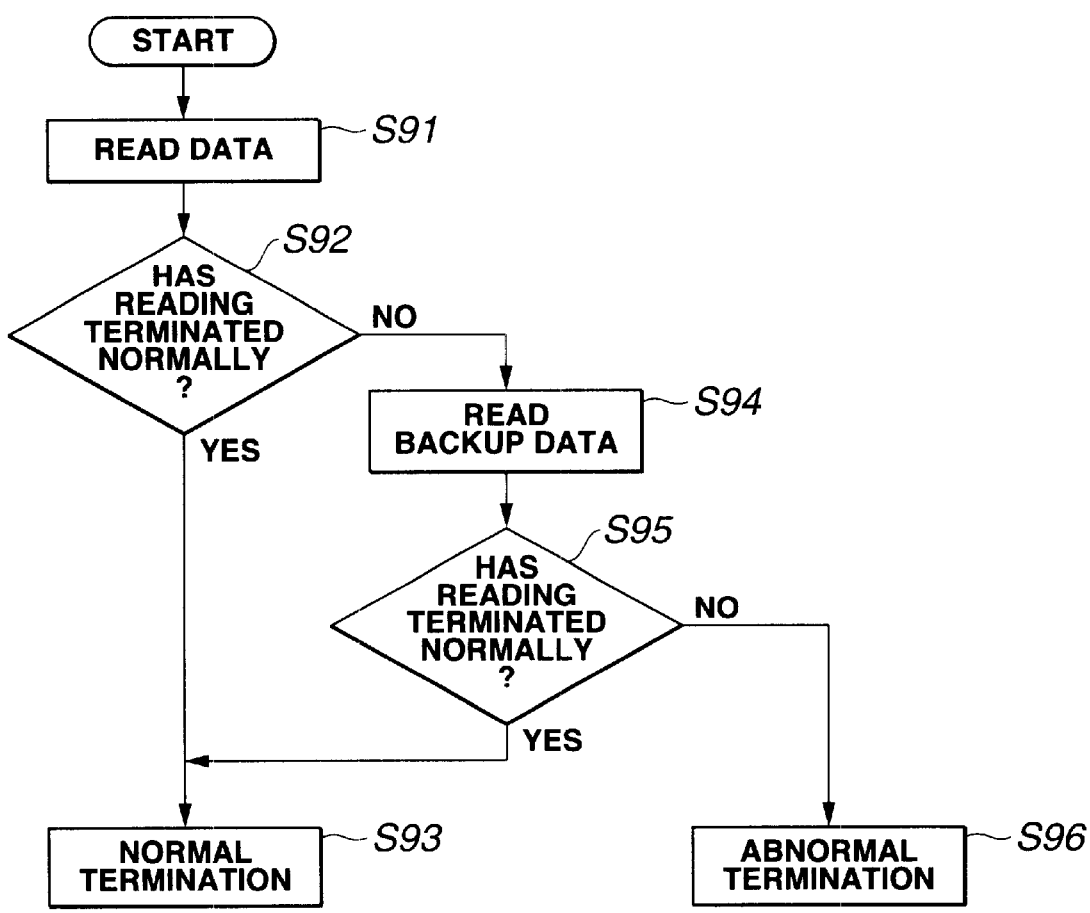

The endoscope waits for the command sent from the connected apparatus as described in FIG. 12 (S81). After the Read command is received, check data contained in the command is checked at step S82 to see if the Read command has been received normally. If the Read command has been received normally, memory reading of step S83 is executed in response to the Read instruction specified for DATA 54. FIG. 13 details the processing of memory reading.

After memory reading of step S83 is completed, it is checked at step S84 if memory reading has terminated normally. If memory reading has terminated normally (S93 in FIG. 13), a normal response command containing read endoscope-related data is transmitted to the connected apparatus (S85). Control is then returned to step S81, and the next command is awaited.

If memory reading has not terminated normally (S96 in FIG. 13), an abnormal response command is transmitted to the connected apparatus at step S86. Control is then returned to step S81. The next command is awaited.

If it is determined at step S82 that the Read command has not been received normally, an abnormal response command is transmitted to the connected apparatus at step S87. Control is then returned to step S81, and the next command is awaited.

At steps S86 and S87, the same abnormal response command may be transmitted. Alternatively, different commands specifying a kind of abnormality may be transmitted so that the cause of the abnormality can be detected.

Each response command is transmitted from the CPU 21 to the connected apparatus via the selector 22 through the connector 25 over the cable 26. The response command is then input to the CPU 29 in the connected apparatus via the serial controller 32 through the connector 27.

Referring back to FIG. 11, the connected apparatus determines at step S63 whether a response command has been received. If no response command has been received, the response command is awaited until a certain time elapses at step S64. If no response command has been received after the certain time lapse, the number of retransmissions Y is decremented by one (S65). It is determined whether the number of retransmissions Y is 0. Control is returned repeatedly to step S62 until the number of retransmissions Y becomes equal to 0. The Read command is thus retransmitted. When the number of retransmissions Y becomes equal to 0, it is concluded that transmission has been retried m times. The processing is then terminated abnormally (S67).

If it is found at step S63 that a response command has been received, it is determined at step S68 whether the response command has been received normally.

If it is determined that the command has not been received normally, the number of retransmissions X is decremented by one (S69). It is determined whether the number of retransmissions X equals 0 (S70). Control is returned repeatedly to step S62 until the number of retransmissions X becomes equal to 0. The Read command is thus retransmitted. When the number of retransmissions X becomes equal to 0, it is concluded that transmission has been retried n times. The processing is then terminated abnormally (S71).

If it is determined at step S68 that the command has been received normally, control is passed to step S72. Check data contained in the command is checked to see if the command is a normal response command. If it is determined that the command is the normal response command, the processing of reading is terminated normally (S73).

If it is determined that the command is not a normal response command, the number of retransmissions Z is decremented by one (S74). It is then determined whether the number of retransmissions Z equals 0 (S75). Control is returned repeatedly to step S62 until the number of retransmissions Z becomes equal to 0. The Read command is thus retransmitted. When the number of retransmissions Z becomes equal to 0, it is concluded that transmission has been retried k times. The processing is then terminated abnormally (S76).

The numbers of retransmissions X, Y, and Z may be set (S61) at every execution of reading as described in the flowchart of FIG. 11. Alternatively, they may be pre-set in the ROM 30 or RAM 31 in order to obviate the necessity of setting.

FIG. 13 is a flowchart describing actions to be performed in the endoscope 2 for executing memory reading (S83) mentioned in FIG. 12.

First, at step S91 in FIG. 13, reading the data division 60 shown in FIG. 7A is executed. It is then determined at step S92 whether the reading has terminated normally.

Figure 14:
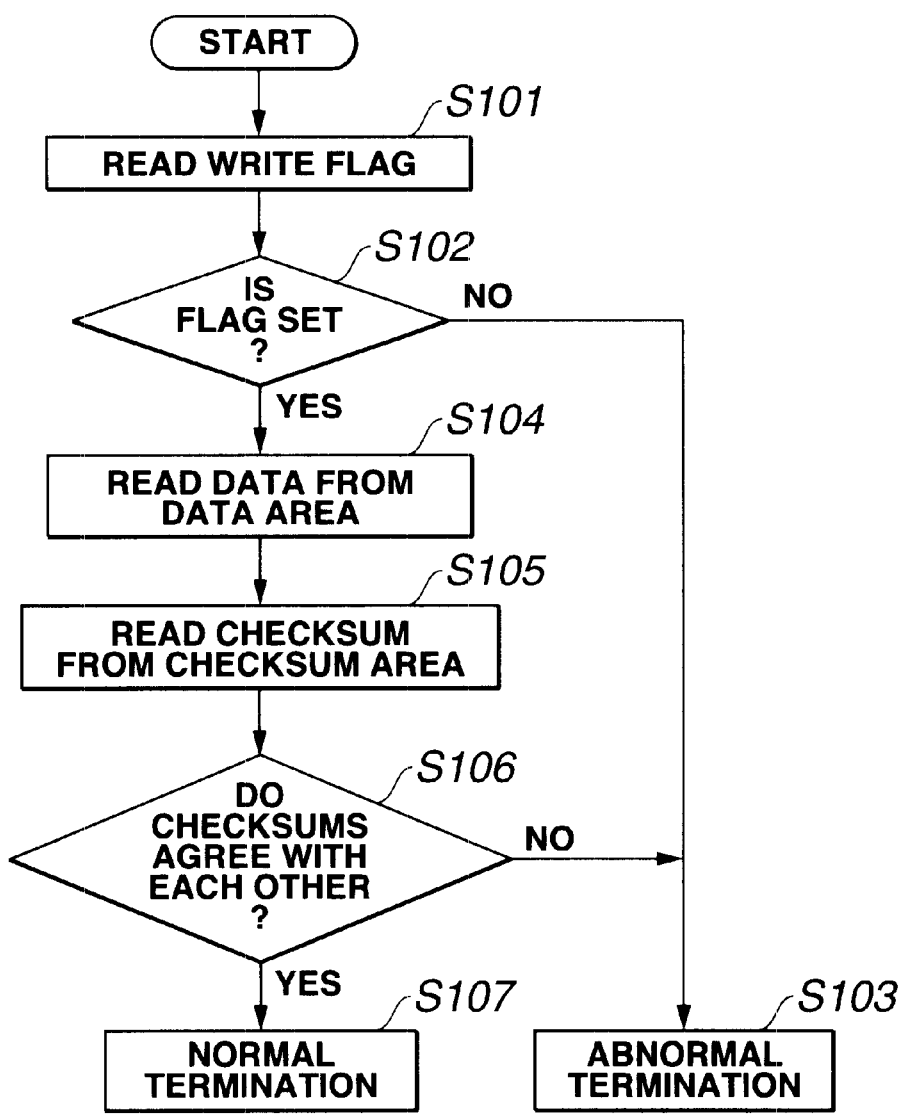

Reading the data division 60 is performed according to the procedure described in FIG. 14.

At the initial step S101, the flag stored in the data write flag area 62 is read.

At step S102, it is determined whether the flag is set. If the flag is not set, it is concluded that data has not been correctly written in the data area 63. The processing is terminated abnormally (S103).

If the flag is set, it is concluded that data has been correctly written in the data area 63. Control is passed to step S104. Endoscope-related data is read from the data area 63.

A checksum is read from the data checksum area 64 at step S105.

At step S105, it is determined whether a checksum calculated from the data read at step S104 agrees with the checksum read at step S105 (S106).

If it is determined at step S106 that the checksums agree with each other, it is concluded that endoscope-related data read at step S104 is correct. The read endoscope-related data is regarded as memory-read data. The processing is terminated normally (S107). If the checksums disagree with each other, it is concluded that the data read at step S104 is incorrect. The processing is terminated abnormally (S103).

Referring back to FIG. 13, if it is concluded that reading the data division 60 has terminated normally (S107), the processing is terminated normally (S93).

If the processing has not terminated normally (S103), reading the backup data division 61 is executed at step S94. It is then determined whether the reading has terminated normally (S95).

Figure 15:
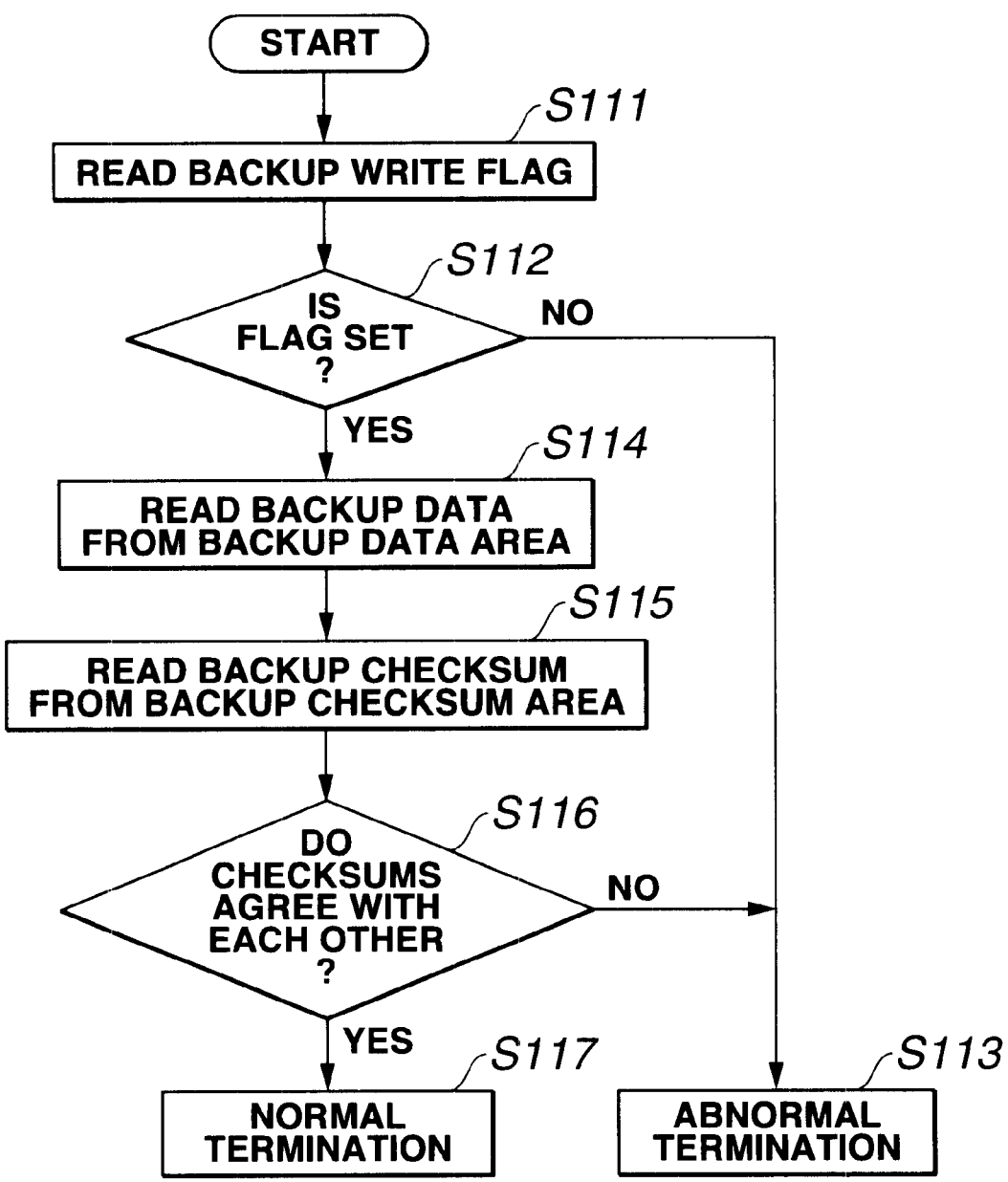

Reading the backup data division 61 is performed according to the procedure described in FIG. 15.

First, at step S111, a flag stored in the backup data write flag area 65 is read.

It is determined at step S112 whether the read flag is set. If the flag is not set, it is concluded that data has not been correctly written in the backup data area 66. The processing is terminated abnormally (S113).

If the flag is set, it is concluded that backup data has been written correctly. Backup data of endoscope-related data is read from the backup data area 66 at step S114.

At step S115, a checksum of the data read at step S114 is read from the backup data checksum area 67.

At step S116, it is checked if a checksum calculated from the data read at step S114 agrees with the checksum read at step S115.

If it is found at step S116 that the checksums agree with each other, it is concluded that data has been written correctly. Endoscope-related data read at step S114 is regarded as memory-read data. It is concluded that reading has terminated correctly. The-processing of reading the backup data division is terminated normally (S117).

If it is found at step S116 that the checksums disagree with each other, it is concluded that data has not been written correctly. Control is passed to step S113. The processing is terminated abnormally.

Referring back to FIG. 13, if it is concluded that reading the backup data division 61 has been terminated normally (S117), memory reading is terminated normally (S93).

If reading the backup data division 61 has not been terminated correctly (S113), memory reading is terminated abnormally.

By checking the flag stored in the flag area 62 or 65, it can be checked whether data has been written in the data area 63 or 66. Specifically, when writing is suspended because a power failure occurs or the power supply of the endoscope 2 is turned off, data stored in the flag area 62 or 65 remains cleared. Incidentally, the power supply of the endoscope is turned off when the endoscope 2 is disconnected from a connected apparatus.

Based on a checksum written in the checksum area 64 or 67, it can be checked if data in the data area 63 or 66 is correct.

Figure 16:
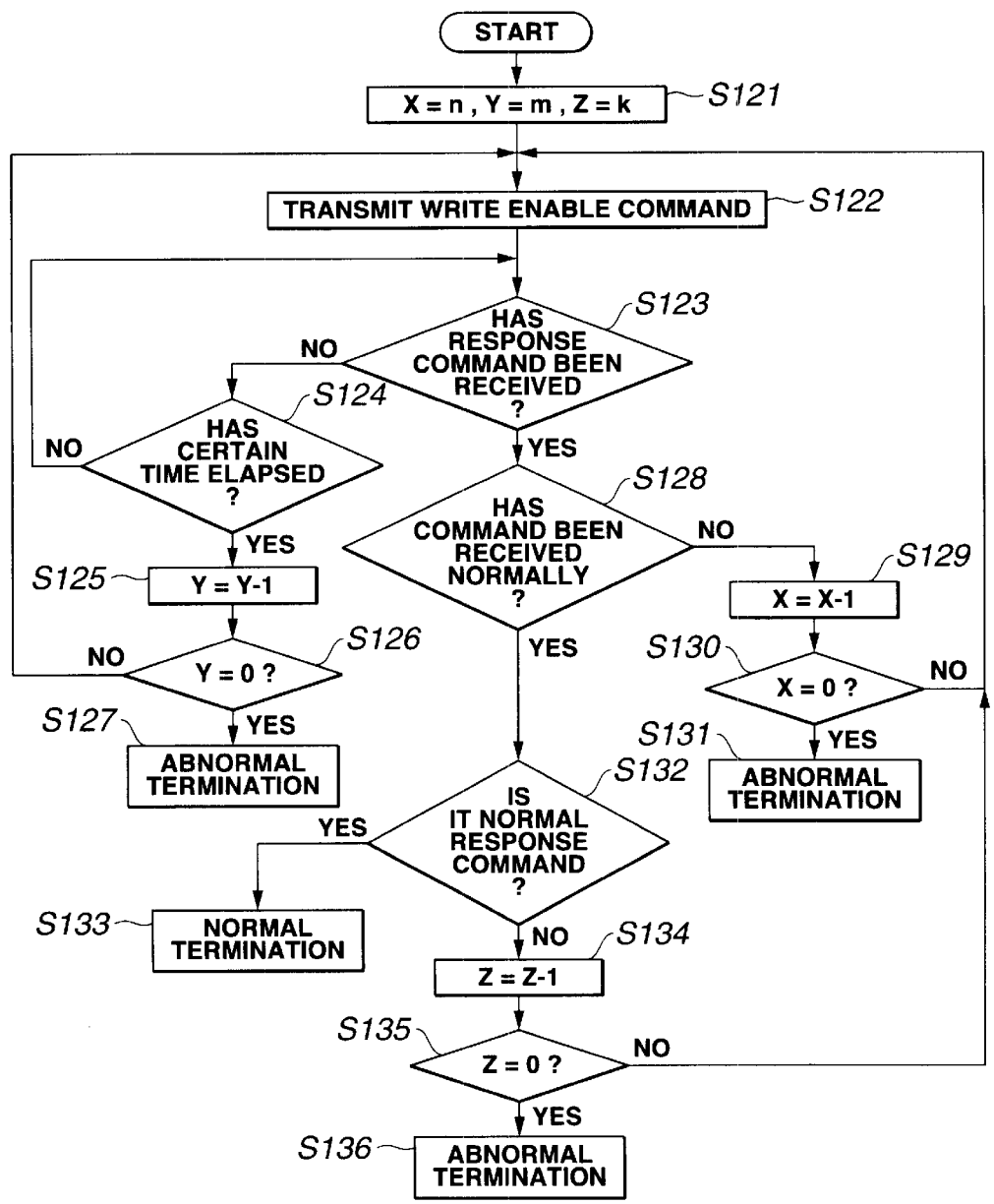
Figure 17:
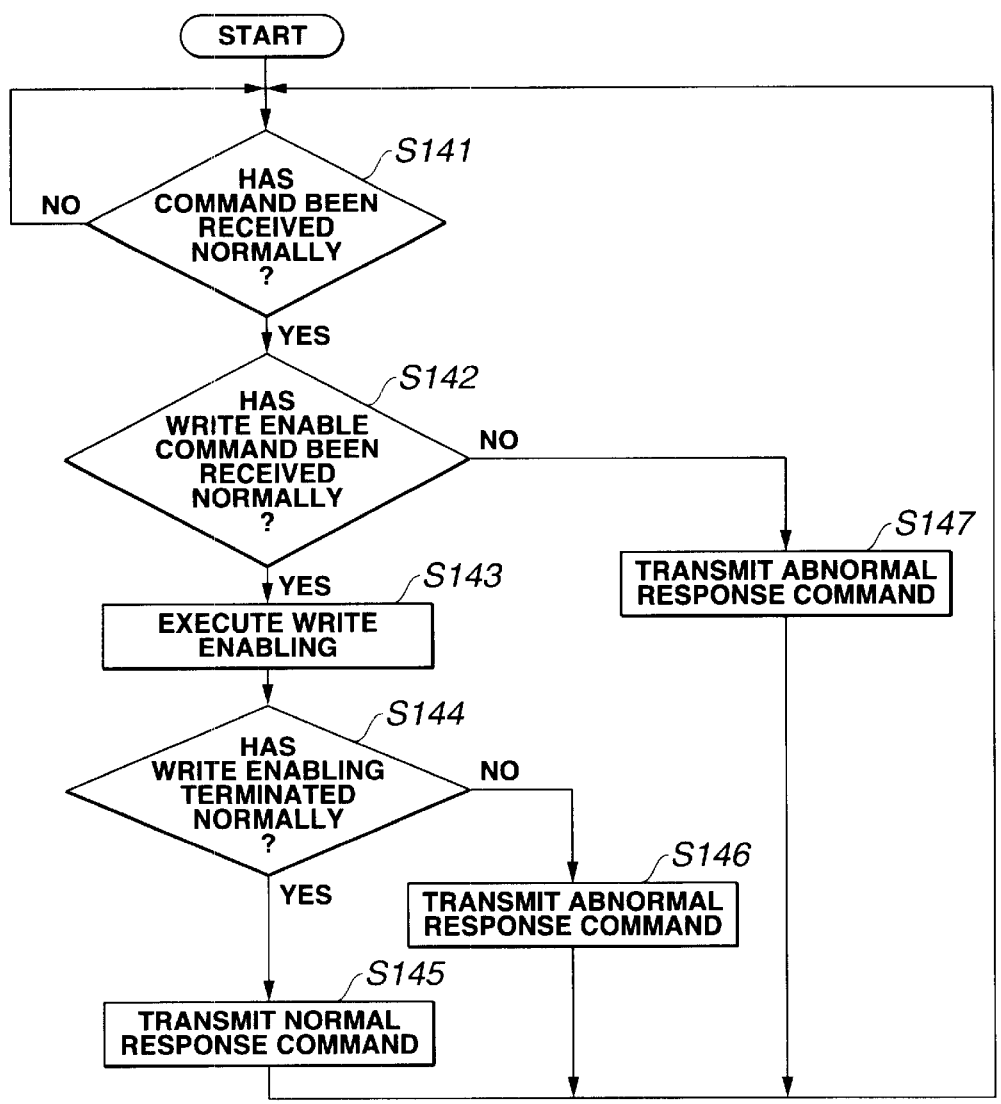

FIG. 16 is a flowchart describing the steps to be performed in a connected apparatus for enabling writing before endoscope-related data is written in the nonvolatile memory 20 in the endoscope, and for executing writing. FIG. 17 is a flowchart describing the steps to be performed in the endoscope for allowing the connected apparatus to enable writing before endoscope-related data is written in the nonvolatile memory 20 in the endoscope, and to execute writing.

Write enabling is intended to enable writing prior to the execution of writing because part or the whole of especially important data of endoscope-related data to be written in the nonvolatile memory 20 may be rewritten readily.

As described in FIG. 16, at step S121, the connected apparatus sets the numbers of retransmissions X, Y, and Z, by which a Write Enable command is transmitted, to n, m, and k respectively.

The number of retransmissions X is the number of times transmission is retried when the connected apparatus fails to correctly receive a response command. The number of retransmissions Y is the number of times transmission is retried when no response command is received within a certain time (for example 30 seconds) after the Write Enable command is sent from the connected apparatus. The number of retransmissions Z is the number of times transmission is retried when a normal response command is not received.

At step S122, a Write Enable command is transmitted to the endoscope 2 in the form of the block 51 shown in FIG. 4 with a Write Enable instruction specified for DATA 54. At step S123, a response command sent from the endoscope 2 is awaited.

To be more specific, the Write Enable command is transmitted from the CPU 29 in the connected apparatus to the endoscope 2 via the serial controller 32 through the connector 27 over the cable 26. The CPU 21 in the endoscope 2 then receives the Write Enable command via the selector 22 through the connector 25.

At step S141 in FIG. 17, the endoscope 2 waits until the command is sent from the connected apparatus. After the Write Enable command is received, it is checked based on the check data contained in the command at step S142 if the Write Enable command has been received normally. If the command has been received normally, write enabling is executed in response to the Write Enable instruction specified for DATA 54 at step S143.

In write enabling, the CPU 21 is programmed so that only when the first command received by the endoscope 2 since termination of write enabling is a Write command, the CPU 21 will execute writing.

At step S144, it is checked if write enabling has terminated normally. If so, a normal response command is transmitted to the connected apparatus at step S145. Control is then returned to step S141, and the next command is awaited.

If it is found at step S144 that write enabling has not terminated normally, an abnormal response command is transmitted to the connected apparatus (S146). Control is then returned to step S141, and the next command is awaited.

If it is found at step S142 that the Write Enable command has not been received normally, an abnormal response command is transmitted to the connected apparatus (S147). Control is then returned to step S141, and the next command is awaited.

The same abnormal response command may be transmitted at steps S146 and S147. Alternatively, different commands specifying a kind of abnormality may be transmitted so that the connected apparatus can detect the cause of an abnormality.

Each response command is transmitted from the CPU 21 to the connected apparatus via the selector 22 through the connector 25 over the cable 26. The CPU 29 in the connected apparatus then receives the response command via the serial controller 32 through the connector 27.

After transmitting a Write command at step S122 in FIG. 16, the connected apparatus determines at step S123 whether a response command has been received from the endoscope 2. If no response command has been received, a response command is awaited at step S124 until a certain time elapses. If no response command has been received within the certain time, the number of retransmissions Y is decremented by one (S125). It is determined at step S126 whether the number of retransmissions Y equals 0. Control is returned repeatedly to step S122 until the number of retransmissions Y becomes equal to 0. The Write Enable command is thus retransmitted. When the number of retransmissions Y becomes equal to 0, it is concluded that transmission has been retried m times. Write enabling is then terminated abnormally (S127).

If a response command has been received, it is checked based on check data contained in the command at step S128 if the command has been received normally.

If a response command has not been received normally, the number of retransmissions X is decremented by one at step S129. It is determined at step S130 whether the number of retransmissions X equals 0. Control is returned repeatedly to step S122 until the number of retransmissions becomes equal to 0. The Write Enable command is thus retransmitted. When the number of retransmissions becomes equal to 0, it is concluded that transmission has been retried n times. Write enabling is then terminated abnormally (S131).

If it is concluded at step S128 that the command has been received normally, control is passed to step S132. It is determined whether the command is a normal response command. If the command is a normal response command, write enabling is terminated normally (S133).

If it is concluded that the command is a normal response command, the number of retransmissions Z is decremented by one (S134). It is determined at step S135 whether the number of retransmissions Z equals 0. Control is returned repeatedly to step S122 until the number of retransmissions Z becomes equal to 0. The Write Enable command is thus retransmitted. When the number of retransmissions Z becomes equal to 0, it is concluded that transmission has been retried k times. Write enabling is suspended and terminated abnormally (S136).

The numbers of retransmissions X, Y, and Z are set (S121) at every execution of write enabling as described in the flowchart of FIG. 16. Alternatively, the numbers of retransmissions X, Y, and Z may be stored in the ROM 30 or RAM 31 in advance in order to obviate the necessity of setting.

Figure 18:
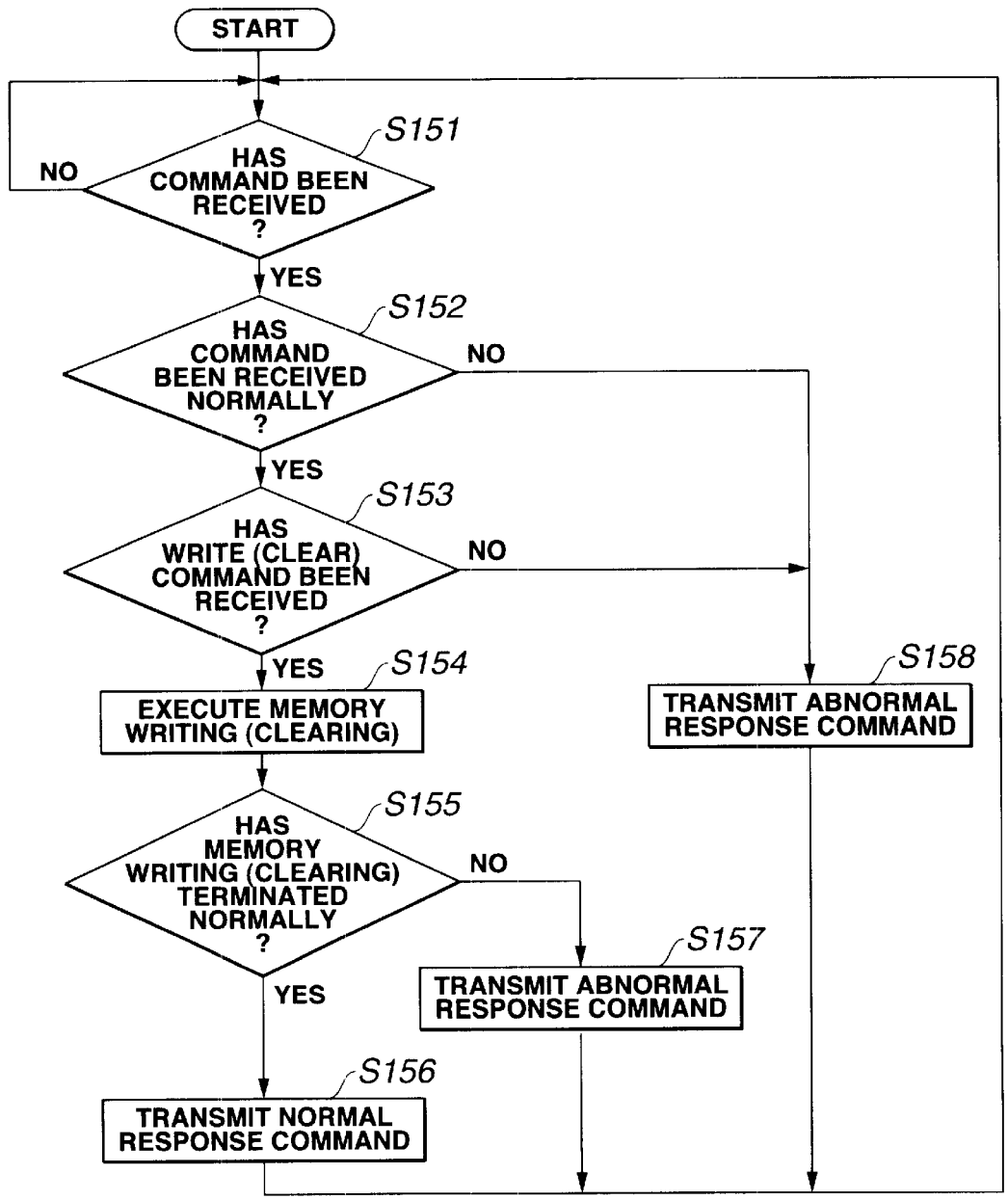

FIG. 18 is a flowchart describing the steps to be performed in the endoscope 2 in response to a command sent from the connected apparatus after write enabling is terminated.

The endoscope 2 waits for a command sent from the connected apparatus at step S151 in FIG. 18. When the command is received, it is checked based on check data contained in the command at step S152 if the command has been received normally.

If the command has been received normally, it is checked at step S153 whether the command is a Write (Clear)

command. If so, writing or clearing is executed (S154) in response to a Write (Clear) instruction specified for DATA 54 (the details are identical to those described in FIG. 8).

At step S155, it is checked if memory writing (clearing) has terminated norm ally. If memory writing (clearing) has terminated normally, a normal response command is transmitted to the connected apparatus at step S156. Control is then returned to step S151, and the next command is awaited.

If it is found at step S155 that memory writing (clearing) has not terminated normally, an abnormal response command is transmitted (S157). Control is then returned to step S151, and the next command is awaited.

The same abnormal response command may be transmitted at steps S157 and S158. Alternatively, different commands specifying a kind of abnormality may be transmitted so that the connected apparatus can detect the cause of an abnormality.

If it is found at step S153 that the command is not the Write (Clear) command, an abnormal response command is transmitted (S158). Control is then returned to step S151, and the next command is awaited.

If it is found at step S152 that the command has not been received normally, an abnormal response command is transmitted to the connected apparatus (S158). Control is then returned to step S151, and the next command is awaited.

As described in FIG. 18, only when the processing succeeding write enabling is writing (clearing), writing is executed.

Figure 19:
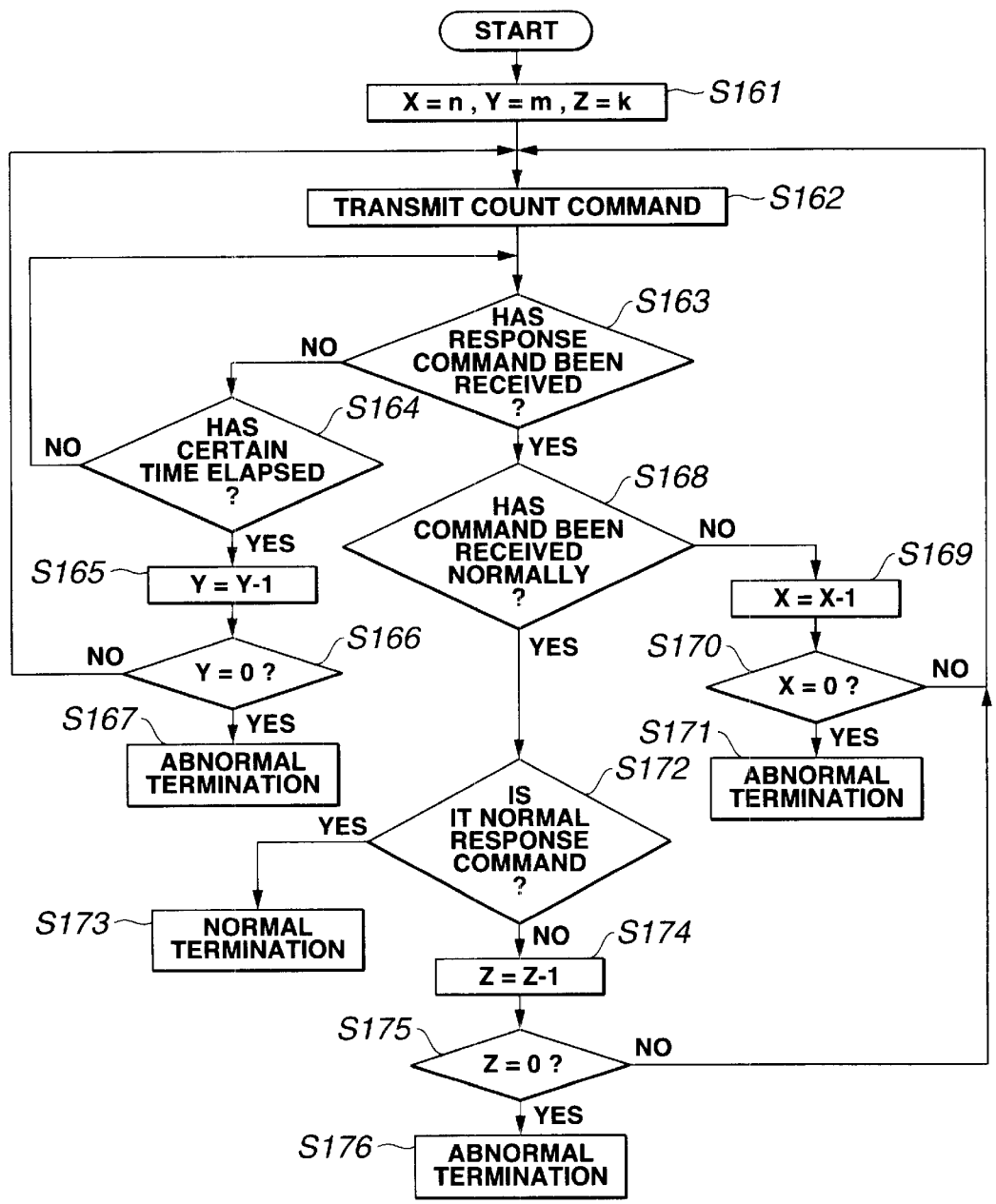
Figure 20:
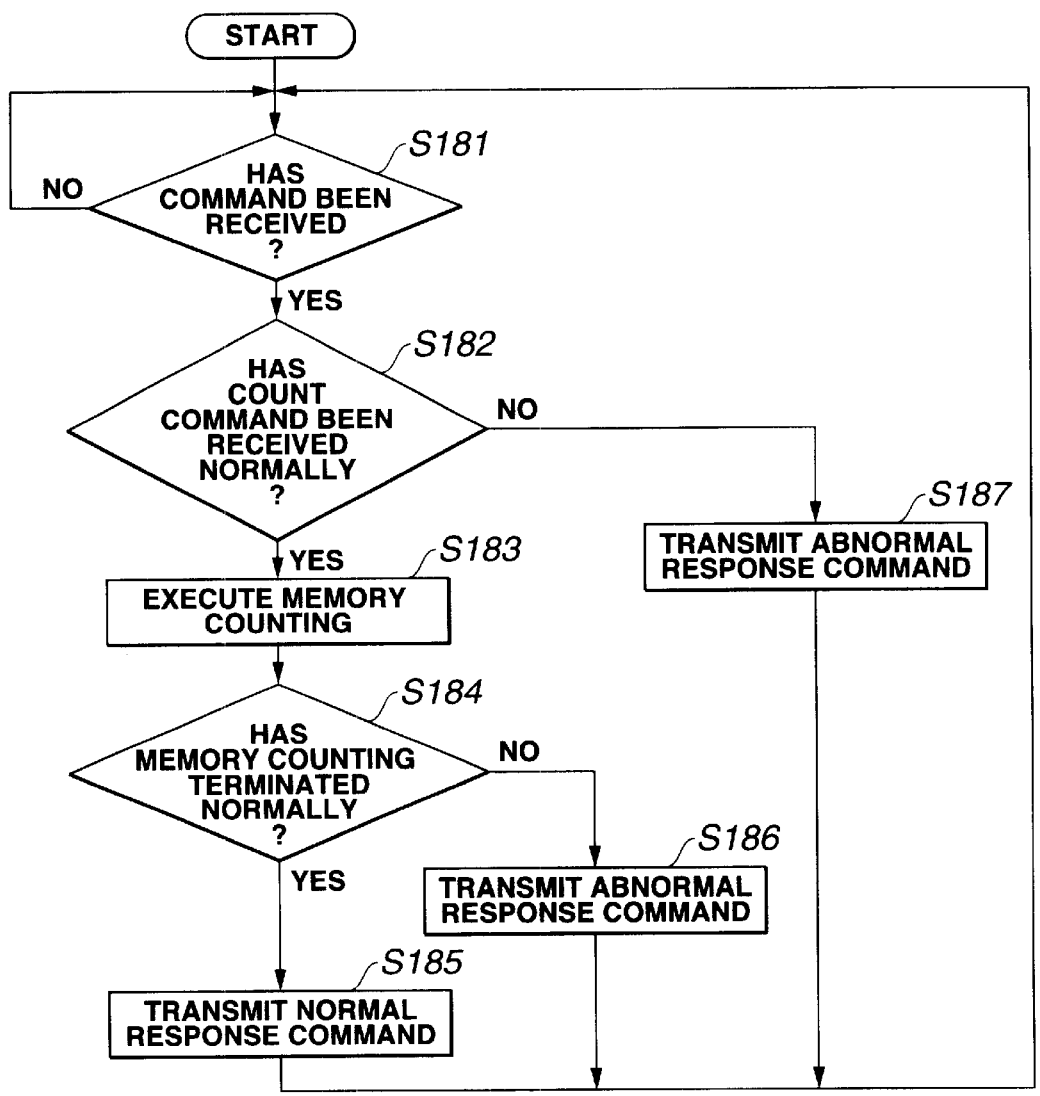

FIG. 19 is a flowchart describing actions to be performed in a connected apparatus (image processing apparatus 3A in FIG. 1) for executing counting to treat count data contained in endoscope-related data stored in the nonvolatile memory 20 in the endoscope 2. FIG. 20 is a flowchart describing actions to be performed in the endoscope for allowing the connected apparatus to execute counting to treat count data contained in endoscope-related data stored in the nonvolatile memory 20 in the endoscope 2.

When the endoscope 2.is connected to the image processing apparatus 3A (see FIG. 1) having the communicating ability, power is fed from the CCD driving power supply 18 in the connected apparatus to the endoscope 2. Thereafter, the image processing apparatus 3A executes counting once so as to count the number of power feeds by which power is fed to the endoscope connected to the image processing apparatus 3A.

To begin with, the image processing apparatus 3A sets the numbers of retransmissions X, Y, and Z, by which a Read command is transmitted, to n, m, and k respectively at step S161 in FIG. 19. X denotes the number of times transmission is retried when the connected apparatus fails to normally receive a response command sent from the endoscope 2. Y denotes the number of times transmission is retried when no response command is received within a certain time (for example, 30 seconds) after a Read command is transmitted from the connected apparatus. Z denotes the number of times transmission is retried when a normal response command is not received.

Thereafter, a Count command is transmitted to the endoscope 2 in the form of the block 51 shown in FIG. 4 with a Count instruction specified for DATA 54 (S162).

To be more specific, a Count command is transmitted from the CPU 29 in the connected apparatus to the endoscope 2 via the serial controller 32 through the connector 27 over the cable 26. The CPU 21 in the endoscope 2 then receives the command via the selector 22 through the connector 25.

The endoscope 2 waits for the Count command sent from the connected apparatus as described in FIG. 20 (S181). After the Count command is received, it is checked based on check data contained in the command if the command has been received normally (S182). If the Count command has been received normally, memory counting is executed in response to a Count instruction specified for DATA 54 (S183).

Memory counting is the processing of reading count data from the nonvolatile memory 20, incrementing the count data by one, and writing the resultant data in the nonvolatile memory 20. The details will be described in conjunction with FIG. 21, After memory counting is completed, it is checked at step S184 whether memory counting has terminated normally. If memory counting has terminated normally (S198 in FIG. 21), a normal response command containing the read data is transmitted to the connected apparatus (S185). Control is then returned to step S181, and the next command is awaited.

If memory counting has not terminated normally (S202 in FIG. 21), an abnormal response command is transmitted to the connected apparatus (S186). Control is returned to step S181, and the next command is awaited.

The same abnormal response command may be transmitted at steps S186 and S187. Alternatively, different commands specifying a kind of abnormality may be transmitted so that the connected apparatus can detect the cause of an abnormality.

Each response command is transmitted from the CPU 21 to the connected apparatus via the selector 22 through the connector over the cable 26. The CPU 29 in the connected apparatus receives the response command via the serial controller 32 through the connector 27.

After transmitting a Count command at step S162 in FIG. 19, the connected apparatus waits until a response command is sent from the endoscope 2 at step S163. If no response command is received, a response command is awaited until a certain time elapses at step S164. If no response command has been received within the certain time, the number of retransmissions Y is decremented by one (S165). It is determined at step S166 if the number of retransmissions Y equals 0. Control is returned repeatedly to step S162 until the number of retransmissions Y becomes equal to 0. The Write Enable command is thus retransmitted. When the number of retransmissions Y becomes equal to 0, it is determined that transmission has been retried m times. Counting is then terminated abnormally (S167).

If a response command has been received, it is checked based on check data contained in the command at step S168 if the command has been received normally.

If the response command has not been received normally, the number of retransmissions X is decremented by one at step S169. It is determined at step S170 whether the number of retransmissions X equals 0. Control is returned repeatedly to step S162 until the number of retransmissions X becomes equal to 0. The Count command is thus retransmitted. When the number of retransmissions X becomes equal to 0, it is concluded that transmission has been retried n times. Counting is terminated abnormally (S171).

In contrast, if it is found at step S168 that the response command has been received normally, control is passed to step S172. It is concluded whether the response command is a normal response command. If the response command is a normal response command, counting is terminated normally (S173).

If it is determined that the response command is a normal response command, the number of retransmissions Z is decremented by one (S174). It is determined at step S175 whether the number of retransmissions Z equals 0. Control is returned repeatedly to step S162 until the number of retransmissions Z becomes equal to 0. The Count command is thus retransmitted. When the number of retransmissions Z becomes equal to 0, it is concluded that transmission has been retried k times. Counting is suspended and terminated abnormally (S176).

The numbers of retransmissions X, Y, and Z may be set (S161) at every execution of counting as described in the flowchart of FIG. 19. Alternatively, the numbers of retransmissions X, Y, and Z may be stored in the ROM 30 or RAM 31 in advance in order to obviate the necessity of setting.

Figure 21:
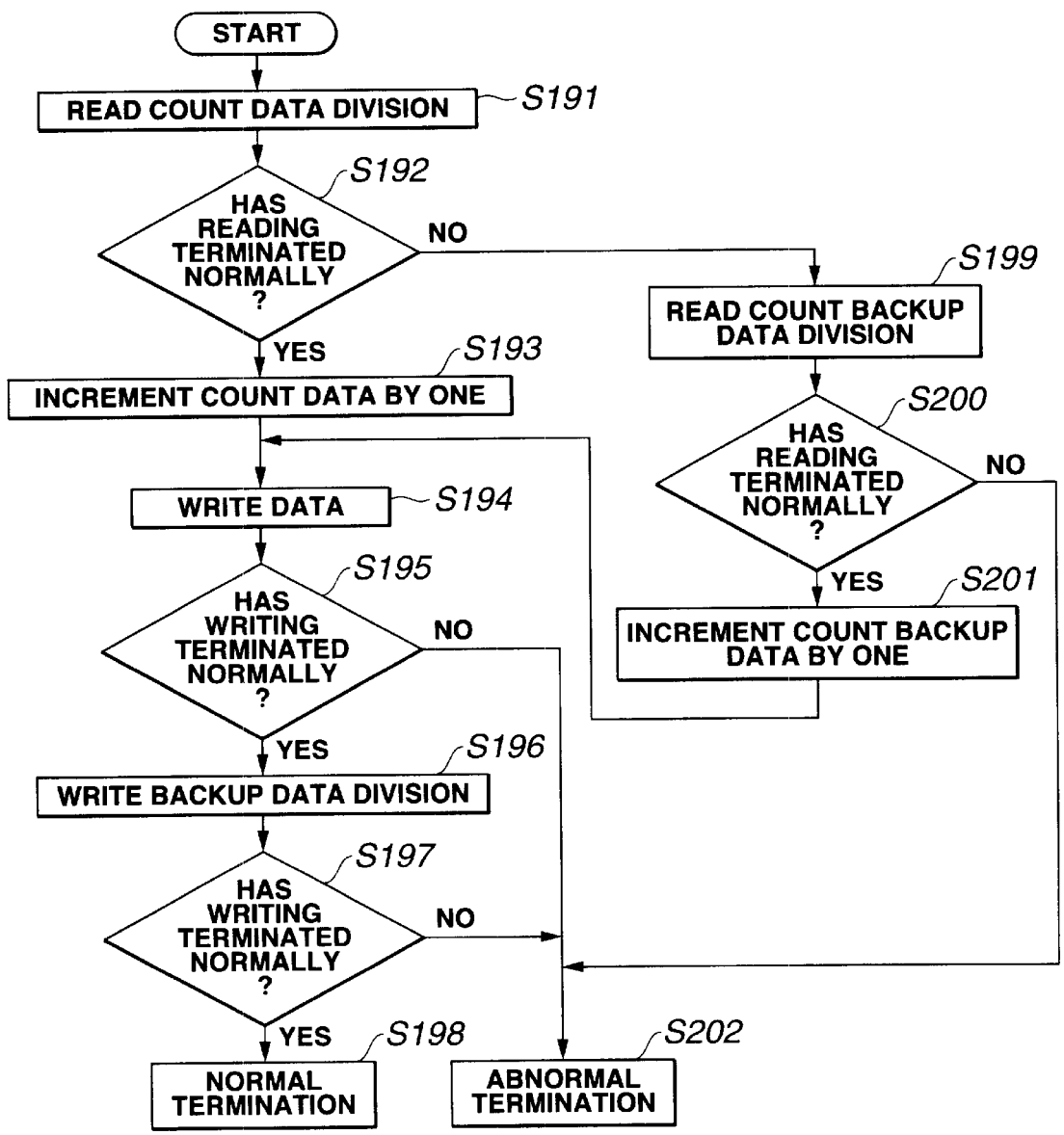

FIG. 21 is a flowchart describing actions to be performed in the endoscope 2 for executing memory counting (S183) mentioned in FIG. 20. Memory counting is performed according to the procedure described below.

Memory reading of step S83 in FIG. 12 or reading described in FIG. 14 is executed in order to read a count data division at step S191.

At step S192, it is checked if reading of step S191 has terminated normally. If the reading has terminated normally, count data read from the data area is incremented by one at step S193. Memory writing described in FIG. 9 is executed in order to write the count data, which has been incremented by one, in the count data division (S194).

At step S195, it is checked if writing of step S194 has terminated normally. If the writing has terminated normally, the count data incremented by one at step S193 is written in the count data backup data division (S196). It is checked at step S197 if writing of step S196 has terminated normally. If the writing has terminated normally, memory counting is terminated normally (S198). If the writing has not terminated normally, memory counting is terminated abnormally (S202).

If it is found at step S192 that the reading of step S191 has not terminated normally, count data is read from the backup data division (S199).

At step S200, it is checked if the reading of step S199 has terminated normally. If the reading has terminated normally, backup data of the count data is incremented by one. The backup data incremented by one is written in the count data division and count data backup data division respectively (S195 to S197).

If it is found at step S200 that the reading has not terminated normally, memory counting is terminated abnormally (S202).

Figure 22:
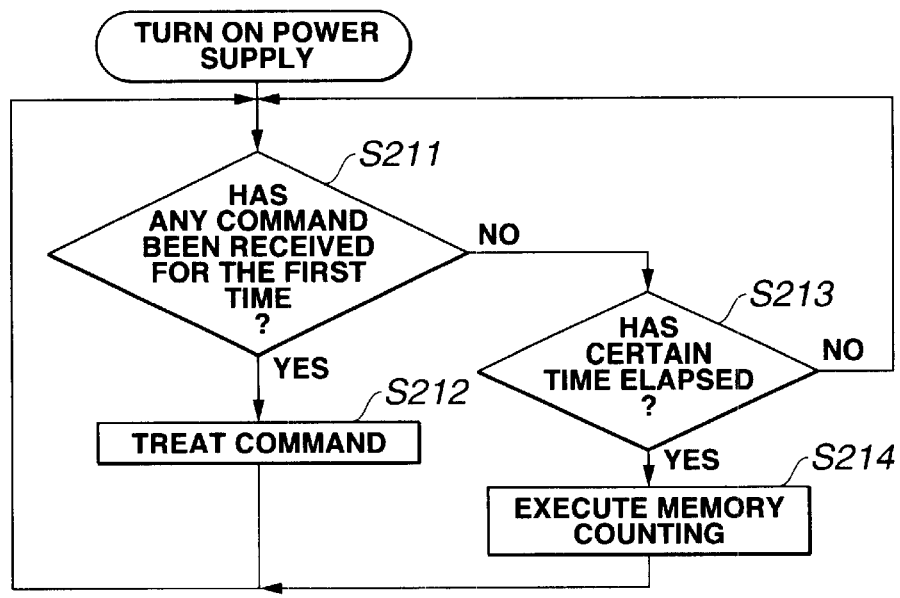

FIG. 22 describes the steps to be performed in the endoscope 2 for autonomously executing counting when connected to a connected apparatus, that is, the image processing apparatus 3B.

When the endoscope 2 is connected to a connected apparatus, power is fed from the CCD driving power supply 18 in the connected apparatus to the endoscope 2. When the endoscope 2 is connected to peripheral equipment 3A, 3C, or 3D having the ability to communicate with the endoscope 2, the peripheral equipment 3A, 3C, or 3D transmits any command to the endoscope 2 within a certain time after power is fed to the endoscope 2. The command is any of the commands that are supposed to be transmitted from the peripheral equipment, which may be the aforesaid Read command, Write command, Write Enable command, and Count command.

The certain time is recorded in advance in the ROM incorporated in the CPU 21 in the endoscope 2. If the endoscope 2 receives any command from the connected apparatus within the certain time, it is concluded that the endoscope has been connected to the apparatus 3A, 3C, or 3D. The endoscope 2 does not autonomously execute counting.

When the endoscope is connected to the image processing apparatus 3B, since the image processing apparatus 3B does not have the ability to communicate with the endoscope 2, no command is transmitted to the endoscope 2. If any command is not received within the certain time after the power supply of the endoscope 2 is turned on, it is concluded that the endoscope 2 has been connected to the image processing apparatus 3B. Counting is then executed in order to count the number of power feeds by which power is fed to the endoscope connected to the image processing apparatus 3B. Specifically, the endoscope 2 performs actions described below.

After the power supply of the connected apparatus is turned on, power is fed from the CCD driving power supply 18 to the endoscope. The regulator 19 varies the voltage level of power, and feeds the resultant power to the supply voltage detector 23, CPU 21, nonvolatile memory 20, and selector 22.

The CPU 21 starts operating according to a program stored in the ROM incorporated therein. The CPU 21 starts a timer incorporated therein, and waits for a command sent from the connected apparatus as described in FIG. 22 (S211).

When any command is received first within a certain time after the power supply is turned on, the received command is treated at step S212. The endoscope 22 does not autonomously execute counting but returns control to step S211 and waits for a command.

If any command is not received, it is judged at step S213 whether a certain time has elapsed with no command received since the power supply is turned on. If the certain time has not elapsed, a command is awaited. If the certain time has already elapsed, it is concluded that the endoscope 2 has been connected to the image processing apparatus 3B that does not have the communicating ability. The endoscope 2 autonomously executes memory counting described in FIG. 15 (S214).

Counting described in FIG. 19, FIG. 20, FIG. 21, and FIG. 22 counts up the number of power feeds by which power is fed to the endoscope 2 connected to the image processing apparatus 3A or 3B used for examination or diagnosis. This makes it possible to count the number of times of use by which the endoscope is used for examination or diagnosis.

In contrast, when the endoscope 2 is connected to the cleaning apparatus 3C shown in FIG. 1, after the cleaning apparatus C cleans (reprocesses) the endoscope 2, counting may be executed in order to increment reprocessing count data (the number of times of reprocessing) contained in endoscope-related data. In this case, the number of times of reprocessing performed by the cleaning apparatus 3C can be learned. As for actions to be performed by the cleaning apparatus 3C, a Reprocessing Count command containing a Reprocessing Count instruction is transmitted to the endoscope 2 instead of the Count command at step S162 in FIG. 19. At step S182 to step S186 in FIG. 20, counting is executed in order to count the number of times of reprocessing.

Figure 23:
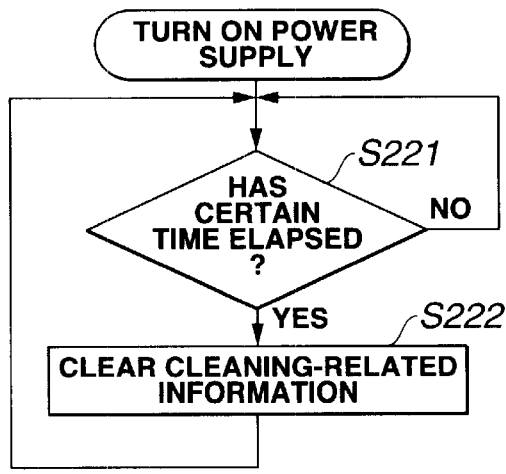

FIG. 23 describes the steps to be performed in the endoscope 2 for autonomously clearing cleaning-related information contained in endoscope-related data stored in the nonvolatile memory 20. The cleaning-related information includes a reprocessing completion time instant, the contents of a Clean instruction, the results of an automatic leakage test, the name of an executor of reprocessing, and the results of a check for clogging of a nozzle.

After the power supply of the connected apparatus is turned on, the regulator 19 varies the voltage level of power fed from the CCD driving power supply 18, and feeds the resultant power to the supply voltage detector 23, CPU 21, nonvolatile memory 20, and selector 22.

The CPU 21 starts operating according to a program stored in the ROM incorporated therein, starts a timer incorporated therein, and determines whether a certain time has elapsed since the power supply is turned on (S221).

If the certain time has not elapsed since the power supply is turned on, it is awaited that the certain time elapses. If the certain time has elapsed, it is judged that the endoscope 2 has been used for examination or diagnosis. Memory clearing described in FIG. 8 is executed in order to clear cleaning-related information (S222). It can thus prevent a malfunction due to the use of (obsolete) cleaning-related information that is not up-to-date.

Next, a description will be made of a practical procedure of treating individual datum out of a plurality of endoscope-related data items. FIG. 24 lists the items and contents of the endoscope-related data written in the nonvolatile memory 20 or the ROM in the CPU 21.

As for processing to be performed on each endoscope-related data, writing or clearing is performed as described in FIG. 5 and FIG. 6. Reading is performed as described in FIG. 11 and FIG. 12. Write enabling is performed as described in FIG. 16 and FIG. 17. Counting or reprocessing counting is performed as described in FIG. 19 or FIG. 20.

FIG. 25 describes the steps to be performed in a connected apparatus for reading an initial examination day, an institution name, or an expiration date of guarantee, which is contained in endoscope-related data, from the nonvolatile memory 20 in the endoscope 2.

The connected apparatus uses connection sensing means (not shown) included in the endoscope 2 and the connected apparatus to determine whether it has been connected to the endoscope 2 (S231). If connection is sensed, identification data is read first (S232).

It is checked at step S233 whether reading identification data has terminated normally. If the reading has terminated normally, an initial examination day, an institution name, or an expiration date of guarantee is read (S234).

It is checked at step S235 whether the reading has terminated normally. If the reading has terminated normally, it is determined at step S236 whether the initial examination day, institution name, or expiration date of guarantee is recorded in the endoscope 2.

The determination is made by checking if clear data (for example, all "00"h) or an initial value set at a factory before delivery is specified as the initial examination day or institution name. If the clear data or initial value is specified, it is concluded that the initial examination day, institution name, or expiration date of guarantee has not been recorded in the endoscope 2. If the clear data or initial value is not specified, it is concluded that the initial examination day, institution name, or expiration date of guarantee has been recorded in the endoscope 2.

If it is concluded that the initial examination day, institution name, or expiration date of guarantee has been recorded, it is checked based on the current date of use indicated by the real-time clock 39 in the connected apparatus and the initial examination day if a period of guarantee (for example, one year) has expired or the expiration date of guarantee (S237) has passed. If the period of guarantee has expired, an alarm is given to indicate that it is an inspection time. If the current date of use indicated by the real-time clock 39 in the connected apparatus has passed the expiration date of guarantee, an alarm is given to indicate that it is the inspection time (S238).

Figure 26:
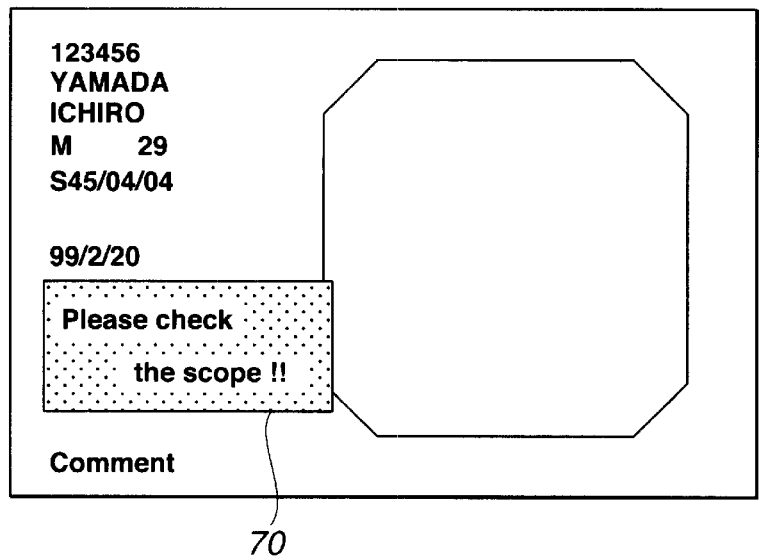

The means for giving an alarm includes display on the monitor 4a, 4b, or 4d, lighting or flickering of the LED 42 on the front panel, and sounding of the buzzer 43. As for display on the monitor 4a, 4b, or 4d, an indication 70 indicating that it is the inspection time may be, as shown in FIG. 26, displayed for a certain time.

After the alarm is given, the processing is terminated (S242).

If it is concluded at step S236 that the initial examination day, institution name, or expiration date of guarantee has not been recorded, the initial examination day, institution name, or expiration date of guarantee is written automatically (S239). The initial examination day may be a current date of use on which the connected apparatus is in use and which is indicated by the CPU 29, the counter timer 35, and real-time clock 39. The initial examination day, institution name, or expiration date of guarantee may be entered by a user at the keyboard 44 and stored in advance in the RAM 31 or ROM 30.

It is then checked whether the writing has terminated normally (S240). If the writing has terminated normally, the processing is terminated (S242). If the writing has not terminated normally, an alarm is given to indicate the fact. The processing is then terminated forcibly (S241).

If the reading of step S233 or step S235 has not terminated normally, an alarm is given to indicate the fact at step S241. The processing is then terminated forcibly. The means for giving an alarm includes display on the monitor 4a, 4b, or 4d, lighting or flickering of the LED 42 on the front panel, and sounding of the buzzer 43.

The processing described in FIG. 25 may be carried out in part of a plurality of connected apparatuses.

In this case, the part of connected apparatuses may have a facility for carrying out the processing installed therein. Alternatively, a separate means may be included for detecting which of the connected apparatuses has been connected to the endoscope.

The processing may be autonomously executed when the power supply of a connected apparatus is turned on or when another endoscope 2 is connected to the connected apparatus. Alternatively, the processing may be executed by pressing a switch on the keyboard 44 or operator panel 41.

Writing the initial examination day, institution name, or expiration date of guarantee may be automatically performed as a step of the processing. Alternatively, the writing may be performed during writing of user-related data described in FIG. 31. The processing will provide the following:

(a) A connected apparatus records and manages an initial examination day, an institution name, or an expiration date of guarantee in association with identification data using the CPU 29, RAM 31, and ROM 30. Consequently, the initial examination day, institution name, or expiration date of guarantee can be recorded and managed in relation to each endoscope 2.

(b) When the initial examination day, institution name, or expiration date of guarantee has not been recorded in the nonvolatile memory 20 in the endoscope 2, they can be recorded automatically.

(c) Since it can be checked based on the initial examination day or expiration date of guarantee if a period of guarantee has expired, a user will be informed of an inspection time for the endoscope 2.

During the processing, identification data may not be read but the initial examination day, institution name, or expiration date of guarantee may be treated.

Figure 27:
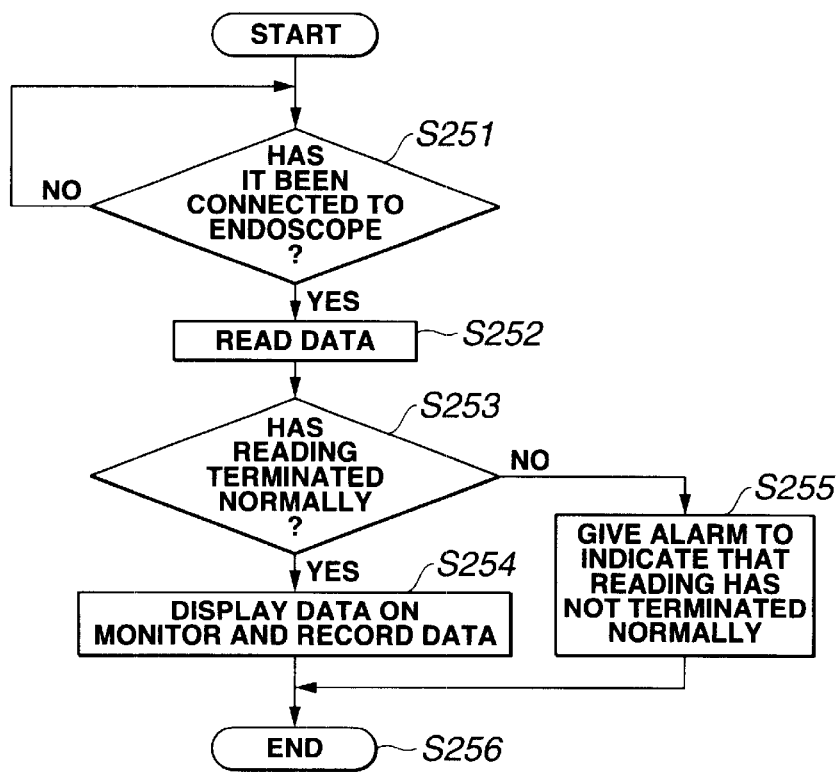

FIG. 27 describes the processing for displaying part or the whole of the endoscope-related data stored in the nonvolatile memory 20 in the endoscope 2 on the monitor 4a, 4b, or 4d or recording it in the image recording apparatus 5a or 5b or the filing apparatus 6a, 6b, or 6c.

A connected apparatus uses connection sensing means (not shown) incorporated in the endoscope and the connected apparatus to determine whether it has been connected to the endoscope 2 (S251). When connection is sensed, endoscope-related data is read from the nonvolatile memory 20 in the endoscope 2 (S252).

As for reading endoscope-related data, data items may be read one by one or may be all read together.

Endoscope-related data may contain identification data.

It is then checked if the reading has terminated normally (S253). If the reading has terminated normally, the endoscope-related data is displayed on the monitor 4a, 4b, or 4d or recorded in the image recording apparatus 5a or 5b or the filing apparatus 6a, 6b, or 6c (S254). The processing is then terminated (S256).

Figure 28:
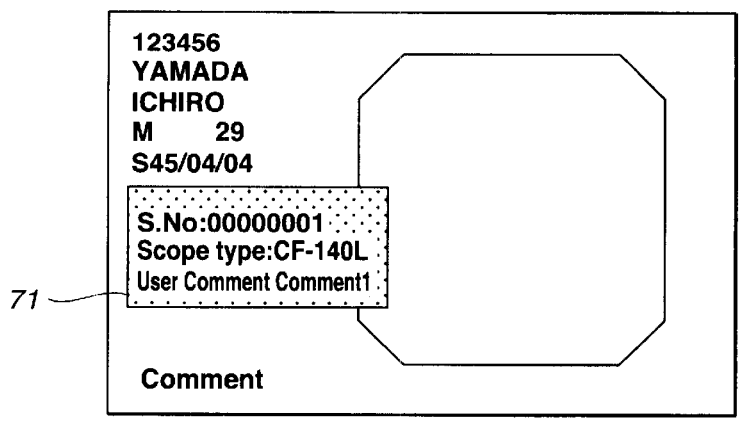

For displaying endoscope-related data on the monitor 4a, 4b, or 4c, as shown in FIG. 28, an indication 71 of endoscope-related data may be displayed for a certain time and then deleted automatically. Alternatively, when a Delete switch on the keyboard 44 or operator panel 41 is pressed, the indication 71 may be deleted.

For recording endoscope-related data in the imaging recording apparatus 5a or 5b or the filing apparatus 6a, 6b, or 6c, endoscope-related data may be transmitted from the CPU 29 in a connected apparatus to the image recording apparatus 5a or 5b or the filing apparatus 6a, 6b, or 6c via the serial controller 32. Alternatively, endoscope-related data may be superimposed on an endoscope image output from the video signal switching circuit 37, and the endoscope image may be recorded.

If it is found at step S253 that the reading has not terminated normally, an alarm is given at step S255 to indicate that the reading has not terminated normally. The processing is then terminated forcibly (S256). The means for giving an alarm includes a display on the monitor 4a, 4b, or 4d, lighting or flickering of the LED 42 on the front panel, and sounding of the buzzer 43.

The processing may be executed automatically when the power supply of a connected apparatus is turned on or when another endoscope 2 is connected to the connected apparatus. Alternatively, the processing may be executed by pressing a switch formed on the keyboard 44 or operator panel 41.

The step of reading data (S252) within the processing may be performed as described in FIG. 11 and FIG. 12 every time the endoscope is put to use. Alternatively, when the same endoscope 2 is kept used, endoscope-related data may be stored in the ROM 30 or RAM 31 in a connected apparatus. When the endoscope 2 is used for a second or more times, the endoscope-related data may be read from the ROM 30 or RAM 31.

The foregoing processing will provide the following:

(a) A connected apparatus records and manages part or the whole of endoscope-related data in association with identification data using the CPU 29, RAM 31, and ROM 30. Consequently, part or the whole of endoscope-related data can be recorded and managed in relation to each endoscope 2.

(b) By displaying endoscope-related data, a user will be provided with information.

(c) Part or all of endoscope-related data is recorded and managed in association with identification data in an image recording apparatus or a filing apparatus. Consequently, an initial examination day and an institution name can be recorded and managed in relation to each endoscope 2.

Figure 29:
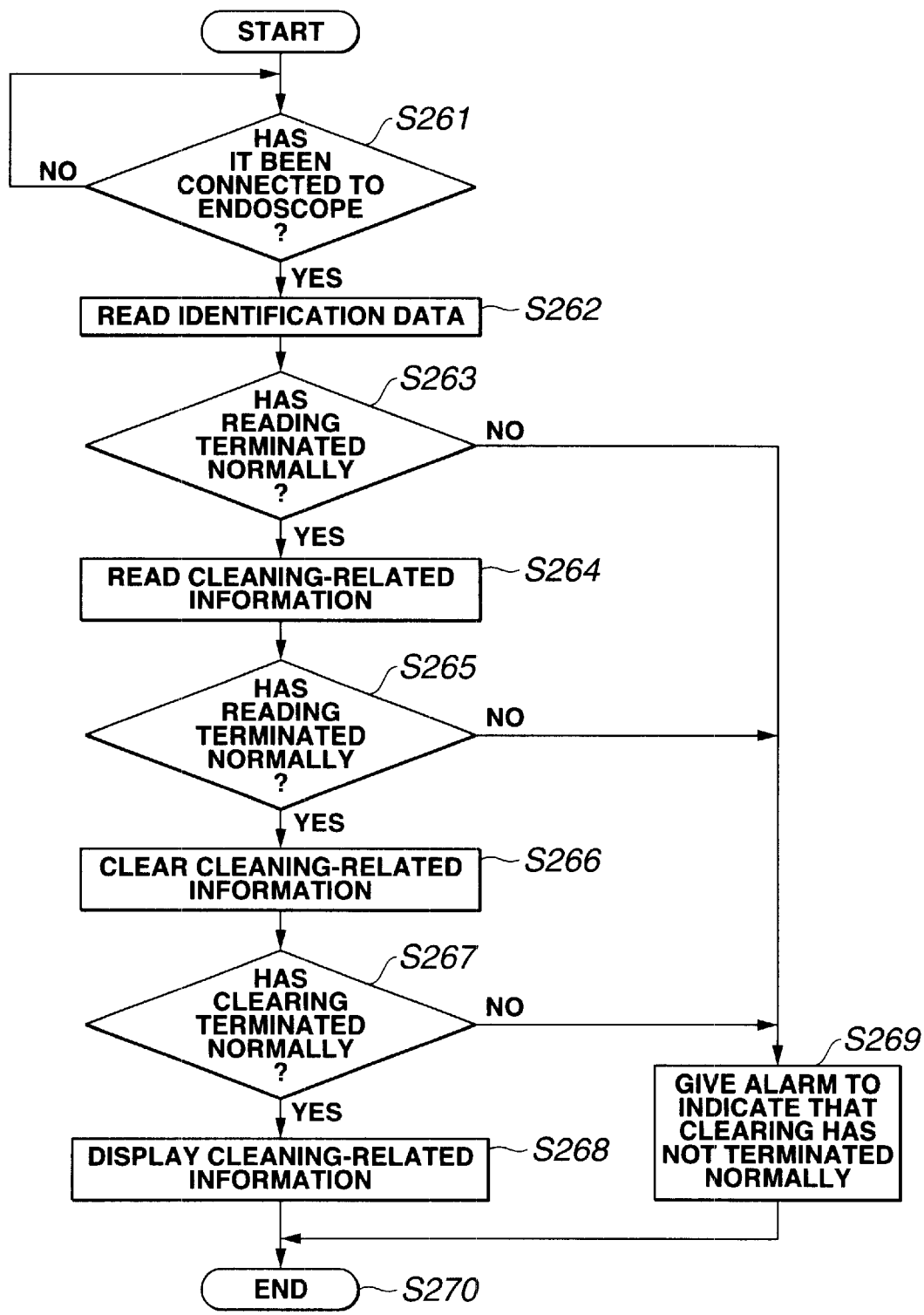
Figure 30:
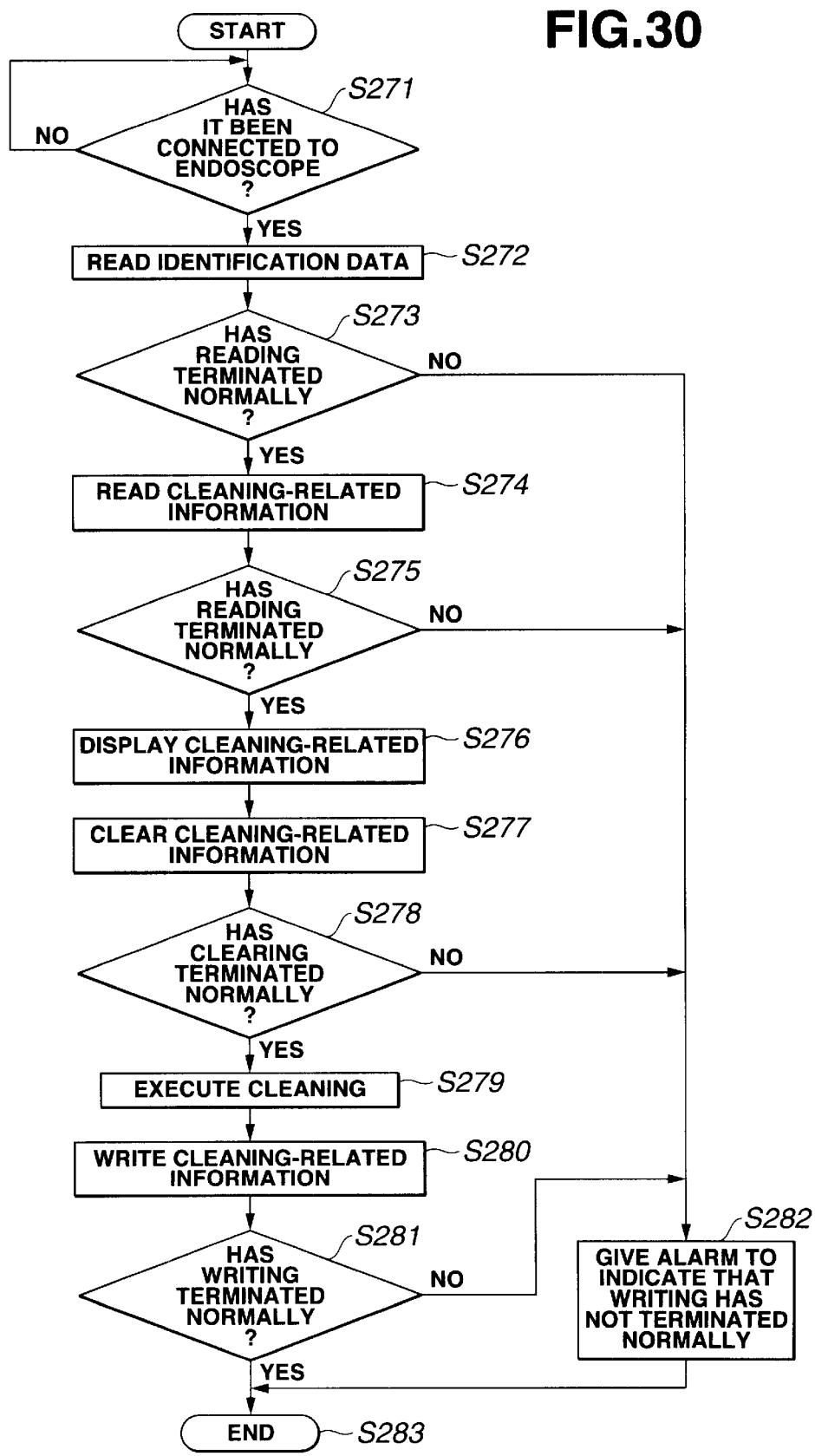

FIG. 29 and FIG. 30 describe processing to be performed in a connected apparatus for treating cleaning-related information contained in endoscope-related data stored in the nonvolatile memory 20 in the endoscope 2. The cleaning-related information includes a reprocessing completion time instant, the contents of a Clean instruction, the results of an automatic leakage test, the name of an executor of reprocessing, and the results of a check for clogging of a nozzle.

FIG. 29 describes the processing to be performed when a connected apparatus is the image processing apparatus 3A or filing apparatus 3D having the ability to communicate with the endoscope 2.

Connection sensing means (not shown) incorporated in the endoscope and the connected apparatus are used to determine whether the connected apparatus has been connected to the endoscope 2 (S261). If connection is sensed, identification data is read (S262).

It is then checked if the reading has terminated normally (S263). If the reading has terminated normally, cleaning-related information is read (S264).

As for reading cleaning-related information, data items may be read one by one or may be all read together.

It is then checked if the reading has terminated normally (S265). If the reading has terminated normally, the cleaning-related information is cleared (S266). Thereafter, it is checked if the clearing has terminated normally (S267). If the clearing has terminated normally, the cleaning-related information is displayed on the monitor 4a, 4b, or 4d or indicated using the LED 42 (S268). The processing is then terminated (S270).

If it is found at step S263 or S265 that the reading has not terminated normally, or if it is found at step S267 that the clearing has not terminated normally, an alarm is given at step S269 to indicate that the reading or clearing has not terminated normally. The processing is then terminated forcibly (S270). The means for giving an alarm includes display on the monitor 4a, 4b, or 4d, lighting or flickering of the LED 42 on the front panel, and sounding of the buzzer 43.

After cleaning-related information is read normally, the cleaning-related information may not be cleared but may be displayed.

The processing may be automatically executed when the power supply of a connected apparatus is turned on or when another endoscope 2 is connected to the connected apparatus. Alternatively, the processing may be executed by pressing a switch on the keyboard 44 or operator panel 41.

FIG. 30 describes the processing to be performed when a connected apparatus is the cleaning apparatus 3C having the ability to communicate with the endoscope 2.

Connection sensing means (not shown) incorporated in the endoscope and the connected apparatus are used to determine whether the connected apparatus has been connected to the endoscope 2 (S271). If connection is sensed, identification data is read first (S272).

It is then checked if the reading has terminated normally (S273). If the reading has terminated normally, cleaning-related information is read (S274). As for reading cleaning-related information, data items may be read one by one or may be all read together.

Thereafter, it is checked if the reading has terminated normally (S275). If the reading has terminated normally, the cleaning-related information is displayed on the monitor 4a, 4b, or 4d or indicated using the LED 42 (S276). The cleaning-related information is then cleared (S277).

After the cleaning-related information is cleared, it is checked if the clearing has terminated normally (S278). If the clearing has terminated normally, the endoscope 2 is cleaned (S278). Cleaning-related information concerning the cleaning is written (S280). Thereafter, it is checked if the writing has terminated normally (S281). If the writing has terminated normally, the processing is terminated (S283).

If the reading of step S273 or S275, the clearing of step S278, or the writing of step S281 has not terminated normally, an alarm is given at step S281 to indicate that the reading, clearing, or writing has not terminated normally. The processing is then terminated forcibly. The means for giving an alarm includes display on the monitor 4a, 4b, or 4d, lighting or flickering of the LED 42 on the front panel, and sounding of the buzzer 43.

The steps of reading identification data (S272), displaying cleaning-related information (S276), reading cleaning-related information (S274), and clearing cleaning-related information (S277) may be omitted from the processing described in FIG. 30. Herein, the cleaning-related information to be read includes a reprocessing completion time instant, the contents of a Clean instruction, the results of an automatic leakage test, and the name of an executor of reprocessing.

Moreover, the step of reading identification data may be omitted from the processing described in FIG. 29 or FIG. 30.

Separately from the processing, cleaning-related information may be cleared in the endoscope 2 as described in FIG. 23. In this case, reading cleaning-related information as described in FIG. 29 or FIG. 30 must be executed within a certain time set in the endoscope 2 after power is fed to the endoscope 2.

The foregoing processing will provide the following:

(a) Since the cleaning-related information is displayed, the cleaning-related information concerning the endoscope 2 can be checked.

(b) The cleaning-related information is recorded and managed in association with identification data using the CPU 29, RAM 31, and ROM 30. Consequently, the cleaning-related information can be recorded and managed in relation to each endoscope 2.

(c) When the endoscope is connected to the cleaning apparatus 3C, the cleaning-related information is written after cleaning is completed. Up-to-date cleaning-related information is thus stored.

(d) After the cleaning-related information is read, the cleaning-related information is cleared. Consequently, the cleaning-related information that is not up-to-date is cleared. Therefore, a malfunction due to a reference to a cleaning-related information that is not up-to-date can be prevented.

Figure 31:
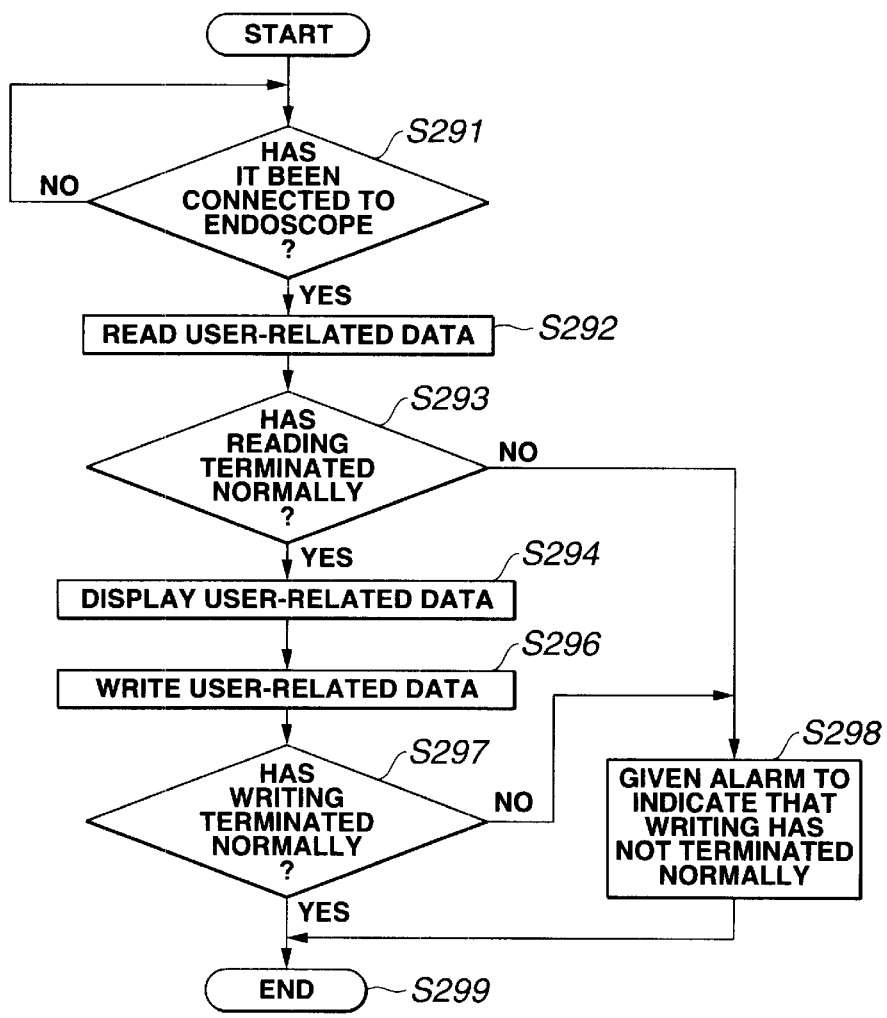

FIG. 31 describes the processing to be performed in a connected apparatus for writing user-related data contained in endoscope-related data stored in the nonvolatile memory 20 in the endoscope 2. The user-related data includes, for example, presence or absence of a contract on a service, a user's comment, a maker's comment, a service engineer's comment, a fixture number, an initial examination day, an institution name, an expiration date of guarantee, a repair record, and an inspection record.

A connected apparatus uses a connection sensing means (not shown) incorporated in the endoscope 2 and the connected apparatus to determine whether it has been connected to the endoscope 2 (S291). If connection is sensed, user-related data is read (S292).

Thereafter, it is checked if the reading has terminated normally (S293). If the reading has terminated normally, user-related data is displayed (S294).

When a displaying switch such as a Setup key or a dedicated displaying key on the keyboard 44 or operator 41 is pressed, user-related data is displayed on the monitor. FIG. 32 shows an example of displaying user-related data. For example, data to be written and other endoscope-related data can be displayed. The data to be written includes presence or absence of a contract on a service, a user's comment, a maker's comment, a service engineer's comment, a fixture number, an initial examination day, an expiration date of guarantee, an institution name, a repair record, and an inspection record. The other endoscope-related data includes an endoscope model name, identification data, a previous examination time instant, a reprocessing completion time instant, count data, reprocessing count data, and a version number. The other endoscope-related data is read or displayed as described in FIG. 27.

After the user-related data is displayed, the user-related data is written (S296). Cursor moving keys on the keyboard 44 or operator panel 41 are pressed, whereby a cursor 72 shown in FIG. 32 is moved to point out user-related data to be written. Character input keys on the keyboard 44 or operator panel 41 are used to enter characters. The entered characters are displayed at the position of the cursor 72, whereby displayed data is changed. Thereafter, a key 44 or a Return key on the operator panel 41 or a dedicated writing key is pressed in order to write the entered data as described in FIG. 5 and FIG. 6. If the writing terminates normally, the processing is terminated (S299).

The user-related data shown in FIG. 32 is deleted by pressing the displaying switch such as the Setup key or dedicated displaying key on the keyboard 44 or operator panel 41 or by pressing a dedicated deleting key.

If it is found at step S293 or S297 that the reading or writing has not terminated normally, an alarm is given at step S298 to indicate that the reading or writing has not terminated normally. The processing is then terminated forcibly.

The means for giving an alarm includes a display on the monitor 4a, 4b, or 4d, lighting or flickering of the LED 42 on the front panel, and sounding of the buzzer 43.

The processing may be executed in part of a plurality of connected apparatuses to be connected to the endoscope.

In this case, part of the connected apparatuses may have a facility for executing the processing installed therein. Otherwise, a detecting means for identifying an apparatus to be connected may be included in the endoscope 2 or a connected apparatus.

The processing may be automatically executed when the power supply of a connected apparatus is turned on or when another endoscope 2 is connected to the connected apparatus. Alternatively, the processing maybe executed by pressing a switch (the foregoing Setup key) on the keyboard 44 or operator panel 41.

When reading the data (S292), the data may be read as described in FIG. 11 or FIG. 12 every time the endoscope 2 is put to use. Alternatively, when the same endoscope 2 is kept used, endoscope-related data may be stored in the ROM 30 or RAM 31 in a connected apparatus. When the endoscope 2 is used for a second or more times, the endoscope-related data may be read from the ROM 30 or RAM 31. The processing will provide the following:

(a) A user records or reads user-related data in relation to each endoscope 2. The user-related information can therefore be stored or read in relation to each endoscope 2.

Figure 33:
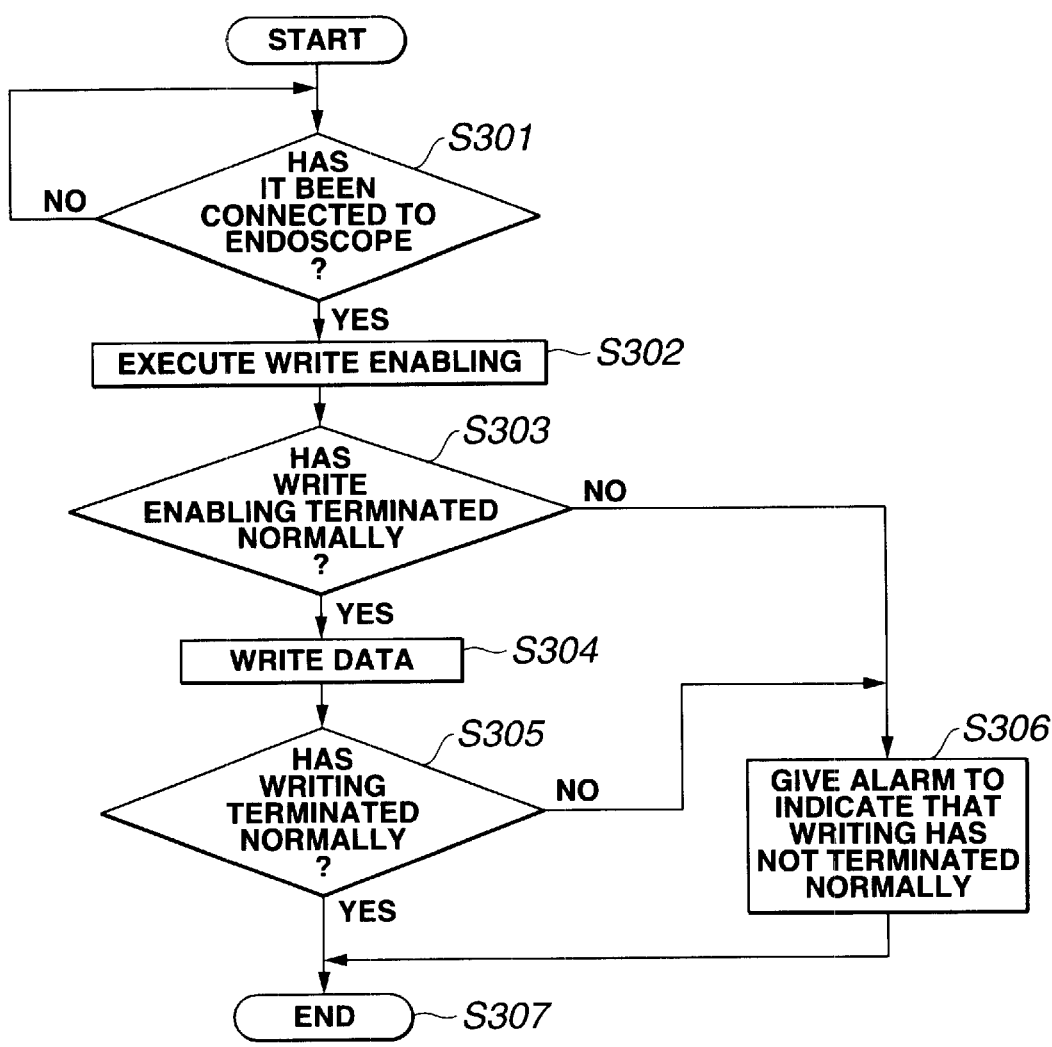

FIG. 33 describes processing to be performed in a connected apparatus for enabling writing before especially important data out of data storable in the nonvolatile memory 20 in the endoscope is written.

Especially important data out of endoscope-related data storable in the nonvolatile memory 20 includes, for example, an endoscope model name, the structure of the distal part of an endoscope, a cleaning tube/adaptor name, a CCD model name, a type of optical filter in a CCD, information relating to the channels in an endoscope, information relating to the switches on an endoscope, a version number, and identification data. When writing is executed due to a malfunction of a connected apparatus, if the important data is rewritten, processing performed using the data fails.

For preventing the failure, writing the important data is enabled only when the processing succeeding write enabling is writing.

To be specific, processing is performed as described below.

A connected apparatus uses connection sensing means (not shown) incorporated in the endoscope 2 and the connected apparatus to determine whether it has been connected to the endoscope 2 (S301). If connection is sensed, write enabling is executed (S302).

Thereafter, it is judged whether write enabling has terminated normally (S303). If the write enabling has terminated normally, data is written (S304). It is then checked if the data writing has terminated normally (S305). If the data writing has terminated normally, the processing is terminated (S307).

If the write enabling of step S303 or the writing of step S305 is not terminated normally, an alarm is given at step S306 to indicate that the write enabling or the writing has not terminated normally. The processing is then terminated forcibly. The means for giving an alarm includes a display on the monitor 4a, 4b, or 4d, lighting or flickering of the LED 42 on the front panel, and sounding of the buzzer 43.

The processing may be executed in part of the connected apparatuses (for example, only in the filing apparatus 3D having the ability to communicate with the endoscope 2). The processing may be designed so that rewriting will be enabled, for example, only at a factory before delivery or during inspection or repair.

In this case, the part of connected apparatuses may have a facility for executing the processing installed therein. Alternatively, a detecting means may be included for identifying a connected apparatus.

Figure 35:
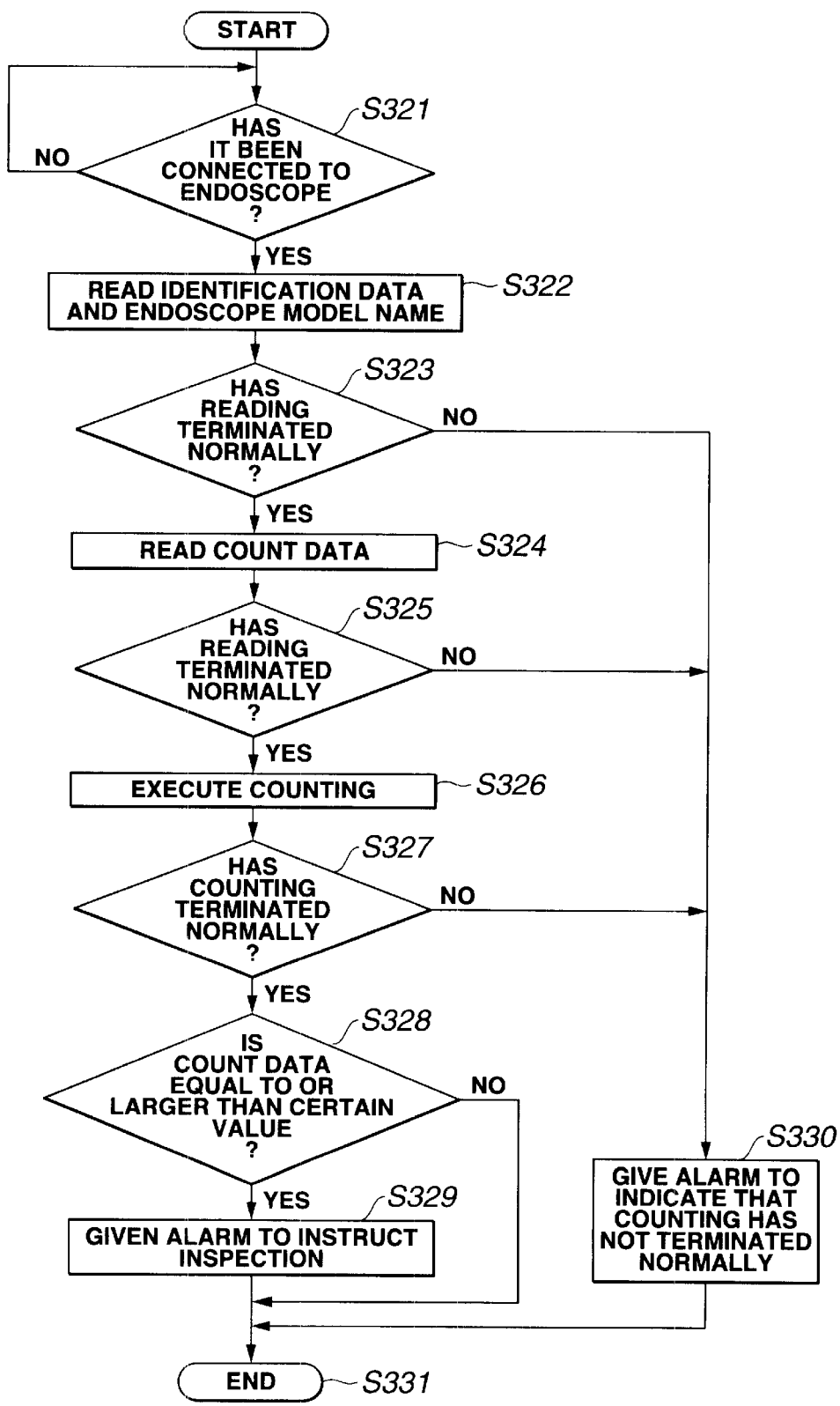

FIG. 35 describes processing to be performed in the image processing apparatus 3A, which has the ability to communicate with the endoscope 2 and is connected to the endoscope 2, for treating count data contained in data to be stored in the nonvolatile memory 20 in the endoscope 2. Incidentally, the apparatuses 3C and 3D do not have a facility for executing counting.

The connected apparatus 3A uses connection sensing means (not shown) incorporated in the endoscope and the connected apparatus to judge whether it has been connected to the endoscope 2 (S321). If connection is sensed, identification data or an endoscope model name is read first (S322).

Thereafter, it is checked if the reading has terminated normally (S323). If the reading has terminated normally, the count data is read (S324).

It is then checked if the count data reading has terminated normally (S325). If the count data reading has terminated normally, counting is executed. The count data is then incremented by one (S326).

It is then checked if the counting has terminated normally (S327). If the counting has terminated normally, it is checked at step S328 if the count data is equal to or larger than a certain value. If the count data is equal to or larger than the certain value, an alarm is given to indicate that it is an inspection time (S329). The processing is then terminated (S331). If the count data falls below the certain value, no alarm is provided and the processing is terminated. The means for providing an alarm includes a display on the monitor 4a, 4b, or 4d, lighting or flickering of the LED 42 on the front panel, and sounding of the buzzer 43.

As for the display on the monitor 4a or 4b, the indication 70 indicating that it is the inspection time may be, as shown in FIG. 26, displayed for a certain time. Moreover, the certain value may be stored in advance in the ROM 30 or RAM 31 in a connected apparatus or may be varied depending on the identification data or an endoscope model name.

If the reading of step S323 or S325 or the counting of step S327 has not terminated normally, an alarm is given at step S330 to indicate that the reading or counting has not terminated normally. The processing is then terminated forcibly.

The means for providing an alarm includes a display on the monitor 4a or 4b, lighting or flickering of the LED 42 on the front panel, and sounding of the buzzer 43. In the processing, counting may be executed without reading of identification data or an endoscope model name.

Moreover, counting may be executed by pressing a Return key or an Enter key on the keyboard 44 or operator panel 41. In addition, the number of times of counting may be written.

In the endoscope 2, if no command is received within a certain time, counting may be automatically executed as described in FIG. 22 separately from the processing. In this case, after the connected apparatus 3A, 3C, or 3D having the ability to communicate with the endoscope 2 feeds power to the endoscope 2, the connected apparatus must transmit any command within a certain time set in the endoscope 2.

Moreover, when the endoscope 2 is connected to a connected apparatus not having the communicating ability, the endoscope 2 will not receive any command from the connected apparatus within the certain time. The endoscope 2, therefore, internally executes counting as described in FIG. 22.

The processing will provide the following:

(a) Count data (the number of power feeds) can be recorded and managed in association with identification data using the CPU 29, RAM 31, and ROM 30 in a connected apparatus. Consequently, count data can be recorded and managed in relation to each endoscope 2.

(b) Only when a connected apparatus is connected to the image processing apparatus 3A or 3B, the number of power feeds is counted. Consequently, the number of times of use by which the endoscope is used for examination or diagnosis can be learned and utilized as highly precise inspection information.

(c) If count data exceeds a certain value, an alarm is given to indicate that it is an inspection time. Consequently, a user can be informed of the proper inspection time for the endoscope 2.

(d) Count data is recorded and managed in association with the identification data in an image recording apparatus or a filing apparatus. Inspection information (count data can be recorded and managed in relation to each endoscope 2.

The number of times of reprocessing contained in the data to be stored in the nonvolatile memory 20 in the endoscope 2 may be treated only when the endoscope 2 is connected to the cleaning apparatus 3C having the communicating ability. The details of the steps to be performed for executing the processing are identical to those described in FIG. 35. However, in this case, the count data mentioned in FIG. 35 must be replaced with the reprocessing count data.

The processing will provide the following:

(a) The reprocessing count data (the number of cleanings) is recorded and managed in association with the identification data using the CPU 29, RAM 31, and ROM 30 in the cleaning apparatus 3C. Consequently, the reprocessing count data can be managed in relation to each endoscope 2.

(b) The number of times of reprocessing (the number of cleanings) is counted so that it can be used as inspection information concerning the endoscope 2.

(c) If the reprocessing count data exceeds a certain value, an alarm is given to indicate that it is an inspection time. Consequently, a user can be informed of the proper inspection time for the endoscope 2.

(d) The reprocessing count data is recorded and managed in association with the identification data in an image recording apparatus or a filing apparatus. The inspection information (reprocessing count data) can be recorded and managed in relation to each endoscope 2.

Figure 36:
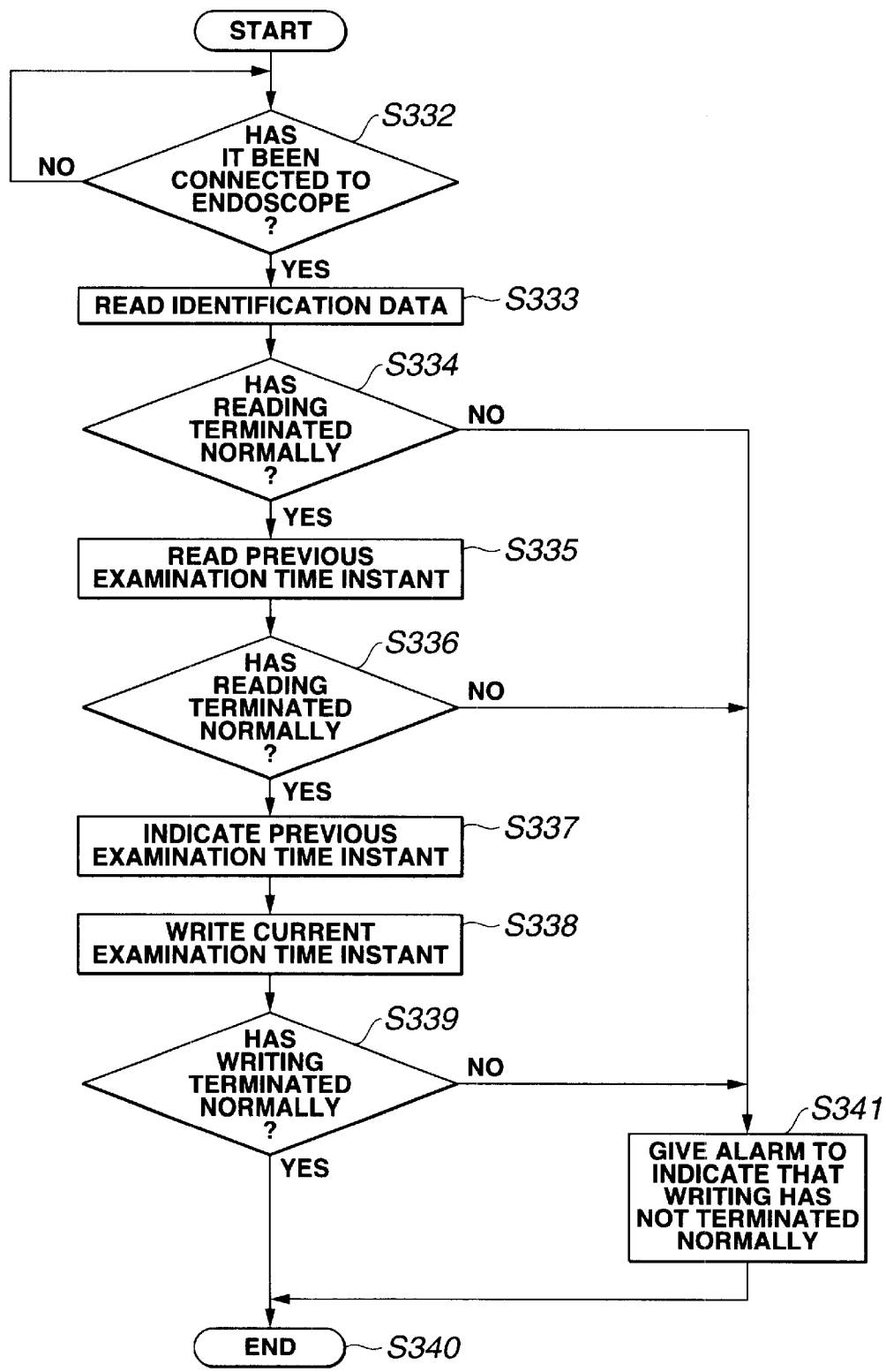

FIG. 36 describes the processing to be performed for treating a previous examination time instant when a connected apparatus is the image processing apparatus 3A.

The connected apparatus (image processing apparatus 3A) uses a connection sensing means (not shown) incorporated in the endoscope 2 and the connected apparatus to determine whether it has been connected to the endoscope 2 (S332). If a connection is sensed, the identification data is read first (S333).

Thereafter, it is checked if the reading has terminated normally (S334). If the reading has terminated normally, a previous examination time instant is read (S335).

It is checked if reading a previous examination time instant has terminated normally (S336). If the reading has terminated normally, the previous examination time instant is indicated (S337).

Figure 37:
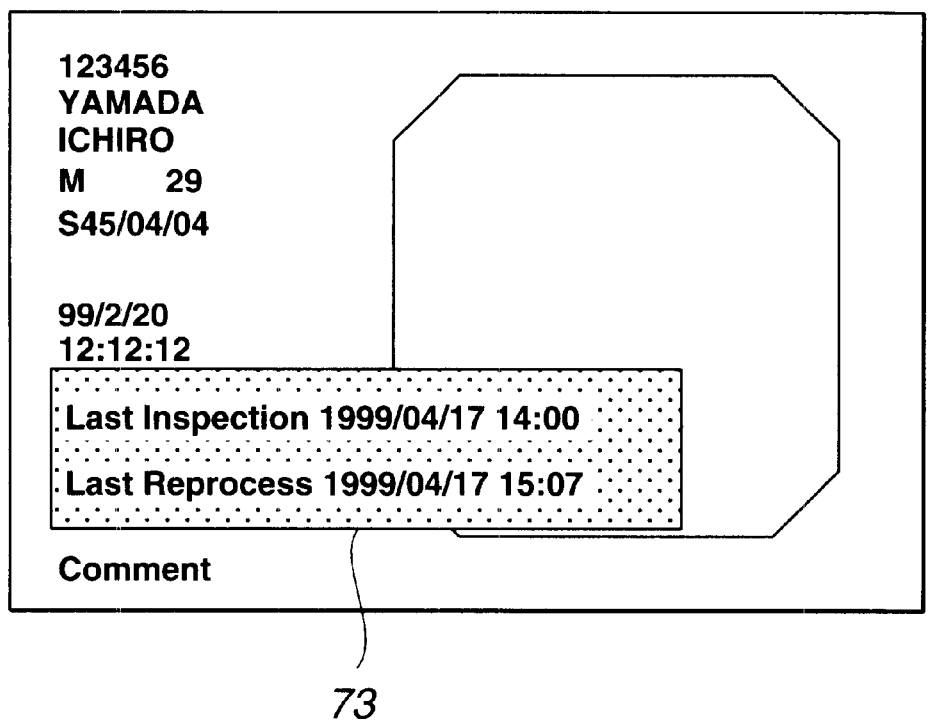

If the indication is displayed on the monitor, the indication of the previous examination time instant, like the one 73 in FIG. 37, may be displayed for a certain time. Moreover, the indication may be deleted by pressing the Delete switch on the keyboard 44 or operator panel.41.

After the indication is displayed, a current examination time instant set in a connected apparatus using the CPU 29 and real-time clock 39 is written in the nonvolatile memory 20 in the endoscope 2 (S338). If the writing terminates normally (S339), the processing is terminated (S340).

If it is found at step S334, S336, or S339 that the writing or reading has not terminated normally, an alarm is given at step S341 to indicate that the writing or reading has not terminated normally. The processing is then terminated forcibly.

The means for giving an alarm includes a display on the monitor 4a, lighting or flickering of the LED 42 on the front panel, and sounding of the buzzer 43.

The processing is executed when the endoscope is connected to the image processing apparatus 3A. The image processing apparatus 3A alone may have a facility for executing the processing installed therein. Alternatively, a detecting means for identifying a connected apparatus may be included in the endoscope 2 or connected apparatus.

In the processing described in FIG. 36, the step S337 of indicating the previous examination time instant and the steps S338 and S339 of writing the examination time instant may be temporally reversed, and the step S339 of displaying an indication may be omitted.

The processing will provide the following:

(a) A user can be informed of the previous examination time instant at which the endoscope 2 and image processing apparatus 3A are previously connected to each other for examination.

(b) The previous examination time instant may be indicated together with a reprocessing completion time instant, which is one of endoscope-related data items listed in FIG. 24, in the same manner as the indication 73 shown in FIG. 37. In this case, the two time instants can be compared with each other, whereby it can be checked if the endoscope 2 has been cleaned (reprocessed) after or before examination. Consequently, it can be judged whether the endoscope 2 is now clean or unclean.

(c) The previous examination time instant may be recorded and managed together with the reprocessing completion time instant in association with the identification data in the image processing apparatus 5a or filing apparatus 6a. Consequently, a cleaning situation and an examination situation can be recorded and managed in relation to each endoscope 2.

The whole or part of the endoscope-related data to be written in the nonvolatile memory 20 or the ROM in the CPU 21 may be written in advance as described below at a factory before the delivery or during the repair using a connected apparatus that is programmable (for example, the filing apparatus 3D).

(1) Data finalized at a factory before the delivery or during the repair is selectively written in relation to each endoscope 2 in an allocated area. The finalized data includes, for example, an endoscope model name, the structure of the distal part of an endoscope, a cleaning tube/adaptor name, a CCD model name, a type of optical filter in a CCD, information of channels in an endoscope, information of switches on an endoscope, identification data, a maker's comment, and a service engineer's comment.

(2) A value of 0 or a pre-set value to be finalized depending on the use situation of the endoscope 2 is written in a data area in which the count data (including the reprocessing count data) are stored.

(3). A value to be finalized depending on the version number of a program written in the ROM in the CPU 21 is written as a version number.

(4) A certain initial value is written as data to be finalized after the delivery from a factory, after the repair, or the time of user's use in an allocated area so that it can be confirmed that no data has been written since the delivery from a factory or the completion of repair. The data to be finalized includes, for example, a reprocessing completion time instant, the contents of a Clean instruction, the results of an automatic leakage test, the name of an executor of reprocessing, an initial examination day, an institution name, a user's comment, an expiration date of guarantee, presence or absence of a contract on a service, the results of a check for clogging of a nozzle, a previous examination time instant, a fixture number, a repair record, and an inspection record. Consequently, it can be judged at, for example, step S236 in FIG. 25 whether data has been stored in the data area.

The present embodiment provides the advantages described below.

Since the endoscope 2 has the programmable storage medium 8, endoscope-related data that may be rewritten, such as, an initial examination day, an institution name, and user-entered data can be written or read. Consequently, the endoscope-related data is stored in each endoscope and can therefore be managed easily.

Moreover, it becomes unnecessary to record and manage the endoscope-related data concerning a plurality of endoscopes in the peripheral equipment to be connected. Consequently, a memory and recording medium in peripheral equipment can be designed compactly. This leads to a reduction in the size of the peripheral equipment. Thus, a user-friendly peripheral equipment is realized.

Moreover, a serial interface is adopted so that communication with the peripheral equipment will be achieved over a sole signal line. A power supply for feeding power to the storage medium 8 and communication unit (communication facility) 7 in the endoscope is used in common as a power supply for feeding power to the solid-state imaging device. This leads to a reduction in the size of a connector through which the endoscope 2 is connected to the peripheral equipment. Thus, a user-friendly endoscope is realized.

Confirmation information used to confirm whether the endoscope-related data is correct is stored in the storage medium 8 in the endoscope 2. Thus, a confirming means for confirming whether the endoscope-related data is correct is included in the endoscope. This contributes to improvement in reliability of the endoscope-related data.

For example, during writing of the endoscope-related data, a power failure may occur or the endoscope 2 may be disconnected from the peripheral equipment. In this case, the endoscope-related data may not be written correctly. The confirmation information can be used to confirm whether the data has been written correctly.

Moreover, backup data of the endoscope-related data is stored in the storage medium 8 in the endoscope 2. Even if the endoscope-related data is destroyed, the backup data can be read and utilized.

Before part or all of the endoscope-related data is written, write enabling is executed. Therefore, if a connected apparatus should malfunction, incorrect writing could be prevented.

Moreover, if the initial examination day or institution name is not stored in the storage medium 8 in the endoscope 2, the peripheral equipment automatically writes the initial examination day or the institution name. Thus, writing is performed without a user's intervention.

An alarming means is included in the peripheral equipment so that if a certain period of time has elapsed since the initial examination day, an alarm will be given to indicate that it is time for inspection. Therefore, a user can be informed of the inspection time. Eventually, failure due to neglect of an inspection can be prevented.

Furthermore, an operating means included in the peripheral equipment is used to display the endoscope-related data on a monitor. Therefore, the endoscope-related data can be displayed whenever a user wants to see it.

A user-entered data area in or from which a user arbitrarily writes or reads data may be defined in the storage medium 8 in the endoscope 2. In this case, the data that a user wants to preserve can be stored in relation to each endoscope.

Furthermore, the endoscope-related data contains the count data indicating the number of power feeds by which power is fed to the endoscope 2. The number of power feeds is counted only when the endoscope is connected to the peripheral equipment used for examination or diagnosis. Consequently, the number of times by which the endoscope 2 has been used for examination or diagnosis can be determined correctly.

Moreover, the endoscope-related data contains the cleaning-related information. A user can determine the cleaning-related data, that is, whether the endoscope 2 has already been cleaned, how the endoscope has been cleaned, when the endoscope has been cleaned, and who has cleaned the endoscope. This leads to efficient cleaning.

Second Embodiment

Next, the second embodiment of the present invention will be described with reference to FIG. 38 to FIG. 58.

Figure 38:
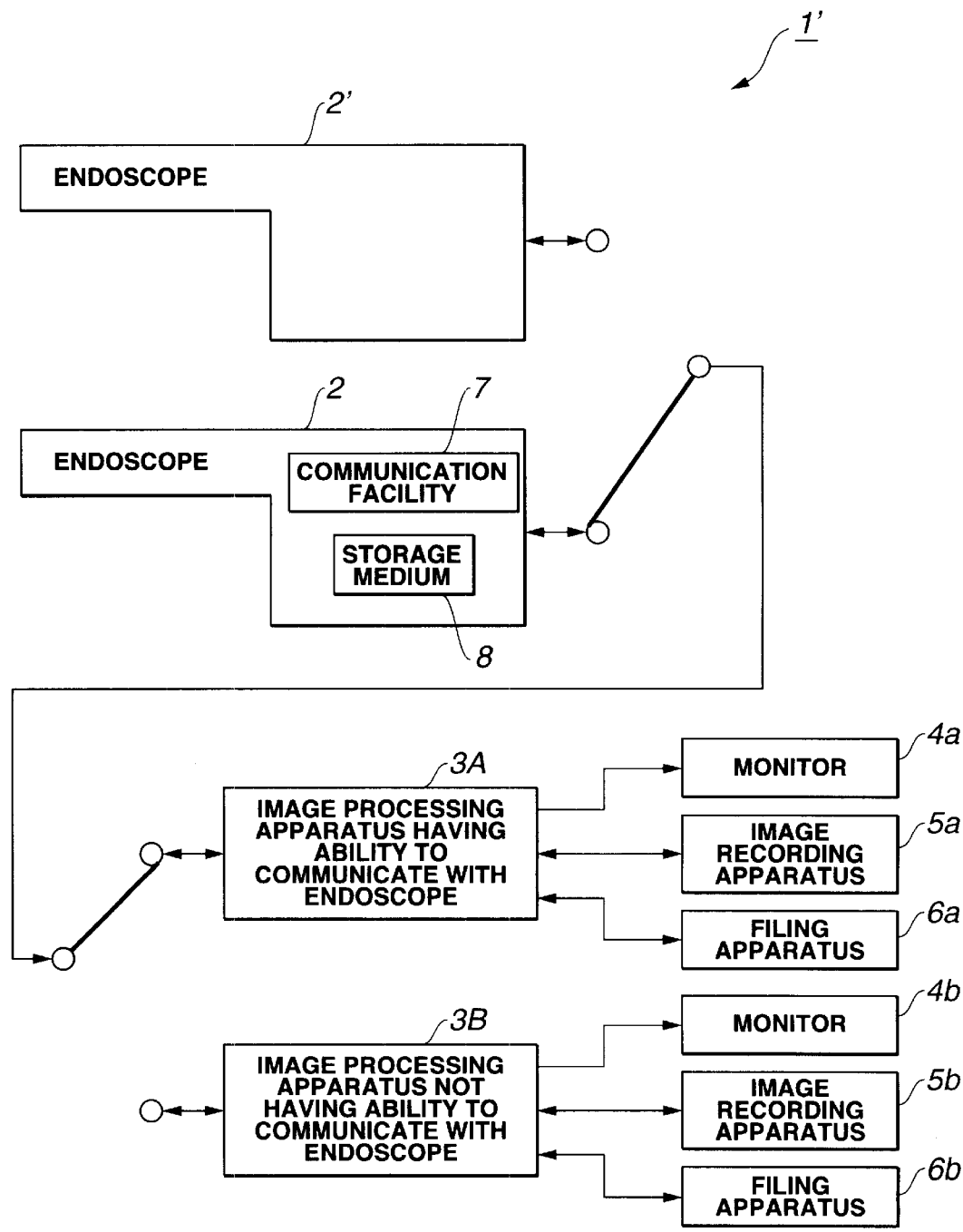
FIG. 38 is a block diagram schematically showing the overall configuration of an endoscope system in accordance with the second embodiment of the present invention.

FIG. 38 shows the configuration of an endoscope system 1' in accordance with the second embodiment of the present invention. The endoscope system 1' in accordance with the second embodiment consists broadly of an endoscope 2', an endoscope 2, an image processing apparatus 3A, an image processing apparatus 3B, monitors 4a and 4b, image recording apparatuses 5a and 5b, and filing apparatuses 6a and 6b. One of the endoscopes 2' and 2 is connected to the image processing apparatus 3A which has the ability to communicate with the endoscope 2. The image processing apparatus 3B has the ability to communicate with the endoscope 2. The monitors 4a and 4b are connected to the image processing apparatuses 3A and 3B.

The endoscope 2 has a communication facility 7 and a storage medium 8 like the endoscope employed in the first embodiment. The endoscope 2' has neither the communication facility 7 nor the storage medium 8.

Figure 39:
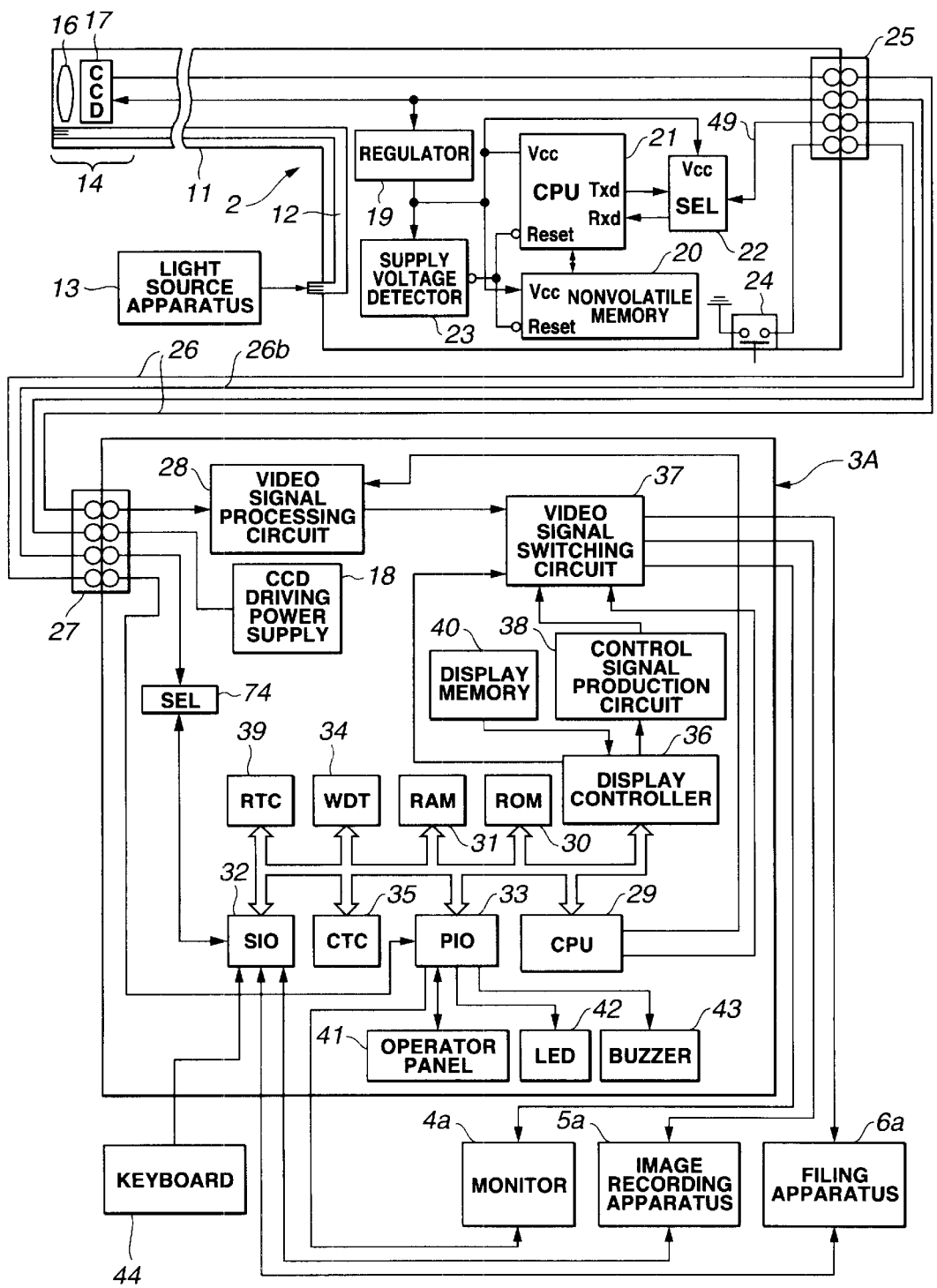
FIG. 39 is a block diagram showing in detail an electronic endoscope and an image processing apparatus having communication capability.

FIG. 39 shows the configurations of the endoscope 2 and the image processing apparatus 3A. The configuration of the endoscope 2 is identical to the one shown in FIG. 2. The configuration of the image processing apparatus 3A is identical to the one shown in FIG. 2. FIG. 39 shows the structures of connectors 25 and 27 more particularly.

Specifically, the endoscope 2 and the image processing apparatus 3A are connected to each other over a cable 26 linking the connectors 25 and 27.

Only one signal line 26b is used to input or output (transmit or receive) the endoscope-related data to or from a nonvolatile memory 20 in the endoscope 2, though a ground line is included separately. The signal line 26b is spliced with a signal line 49 in the endoscope 2, and routed to the nonvolatile memory 20 via a selector 22 and a CPU 21. The endoscope-related data is stored or read in or from the nonvolatile memory 20 through a single input/output terminal coupled to the signal line 49.

Differences of the second embodiment from the first embodiment will be described below.

A practical procedure for treating the individual items of the endoscope-related data will be described below. FIG. 40 lists items of the endoscope-related data to be written in the nonvolatile memory 20. For example, an endoscope model name, a serial number, the number of power feeds, the number of inspections, an owner name or institution name, the results of a check for clogging of a nozzle, and an initial examination day are included in the items of the endoscope-related data.

Part of endoscope-related data (for example, a version number) may be stored not only in the nonvolatile memory 20 but also in the ROM in the CPU 29 and a RAM.

Moreover, various kinds of processing are executed in order to treat each endoscope-related datum. Above all, writing or clearing is executed out as described in FIG. 5 and FIG. 6. Reading is executed as described in FIG. 11 and FIG. 12. Write enabling is executed as described in FIG. 16 and FIG. 17. Counting is executed as described in FIG. 19 and FIG. 20.

Figure 41:
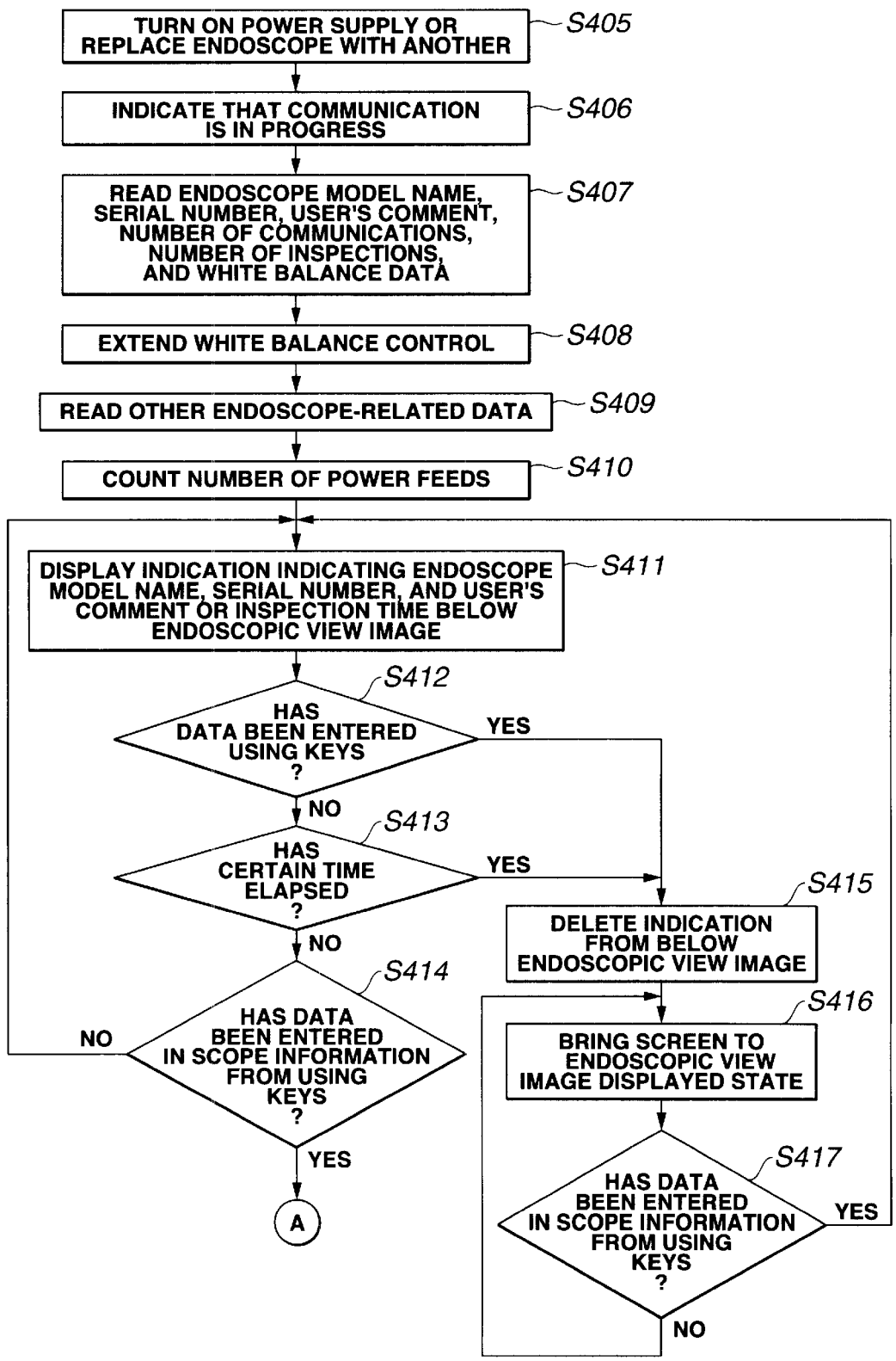
FIG. 41 is a flowchart describing the steps to be performed in practice when the endoscope and the image processing apparatus both of which have communication capability are connected to each other.
Figure 42:
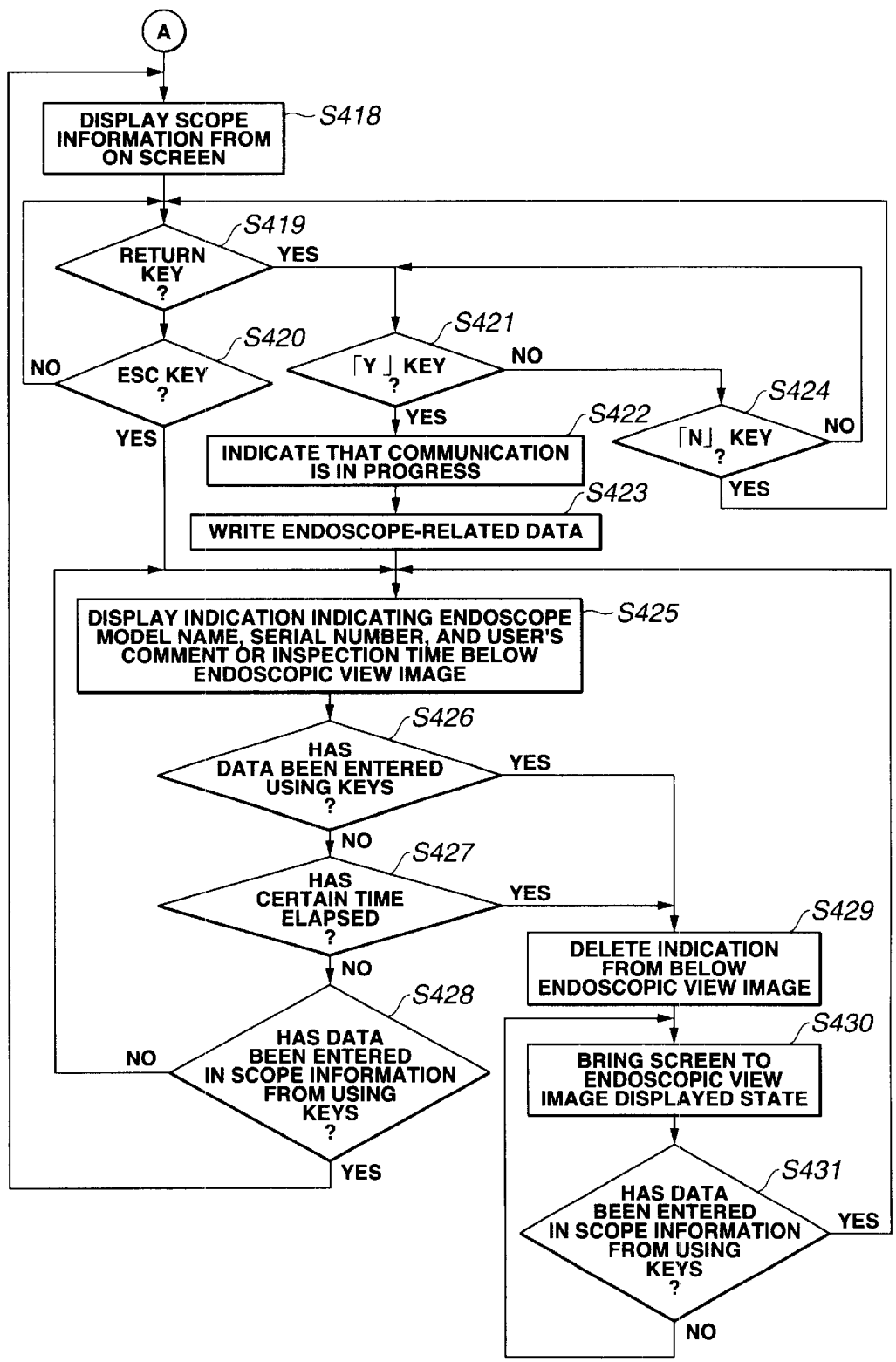
FIG. 42 is a flowchart describing the steps to be performed in practice when the endoscope and the image processing apparatus both of which have communication capability are connected to each other.

FIG. 41 and FIG. 42 are flowcharts describing a series of steps to be performed when the endoscope 2 and the image processing apparatus 3A are connected to each other.

After the image processing apparatus 3A is connected to the endoscope 2, the power supply is turned on or the endoscope 2 is replaced with another with the power supply of the image processing apparatus 3A turned on (S405). The image processing apparatus 3A uses a connection sensing means (not shown) incorporated therein to sense if it has been connected to the endoscope 2. An indication that communication with the endoscope 2 is in progress is displayed (S406). Through communication reading, writing, write enabling, or counting is executed.

Figure 43:
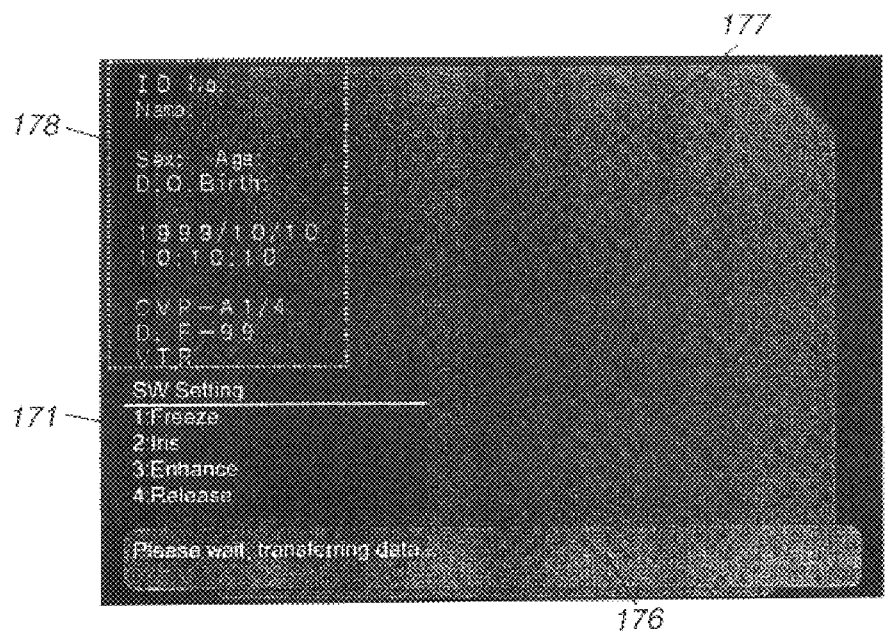
FIG. 43 shows an example of an indication that communication is in progress.

FIG. 43 shows an example of an indication that the communication is in progress. An endoscopic view image 177 is produced by the endoscope 2. Information 178 is related to the endoscopic view image 177, and includes an identification number, a patient's name, a patient's sex, a patient's age, a patient's date of birth, a current date of examination, connection information concerning a recording apparatus connected to the image processing apparatus 2, and the number of records. Information 171 specifies the -functions of switches on the endoscope 2. An indication 176 indicates that communication is in progress (for example, "Please wait, transferring data ¼" is displayed).

When communication is in progress, the indication 176 that communication is in progress and the information 171 of the switches 24 on the endoscope 2 are displayed. This is intended to prevent a user from turning off the power supply of the image processing apparatus 3A or replacing the endoscope 2 with another.

The indication that communication is in progress (S406) may be deleted with the completion of step S407 or steps S407 to S410 or in a certain time (for example, approximately 5 seconds). Moreover, the indication may be switched to an indication displayed at step S411 (to be described later). Otherwise, both the indications may be displayed.

With the indication displayed at step S406, part of the endoscope-related data stored in the nonvolatile memory 20 in the endoscope 2 may be read (S407). Part of the endoscope-related data includes, for example, an endoscope model name, a serial number, a user's comment, the number of power feeds, the number of inspections, and white balance data. The white balance data is then used to attain a white balance (S408).

Figure 45:
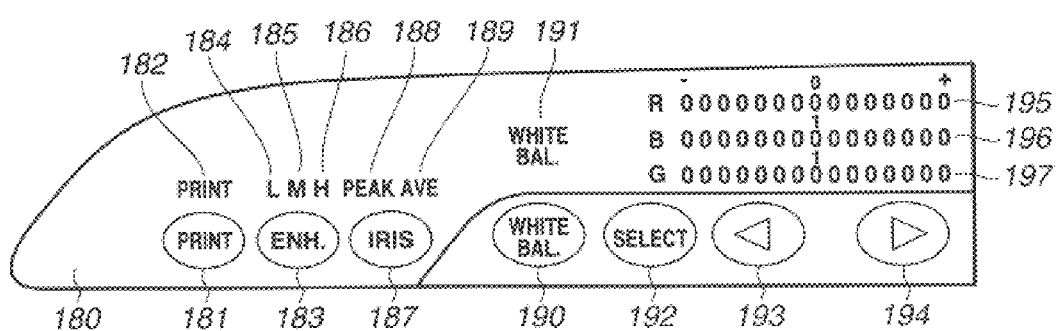
FIG. 45 shows the arrangement of switches on an operator panel.
Figure 44:
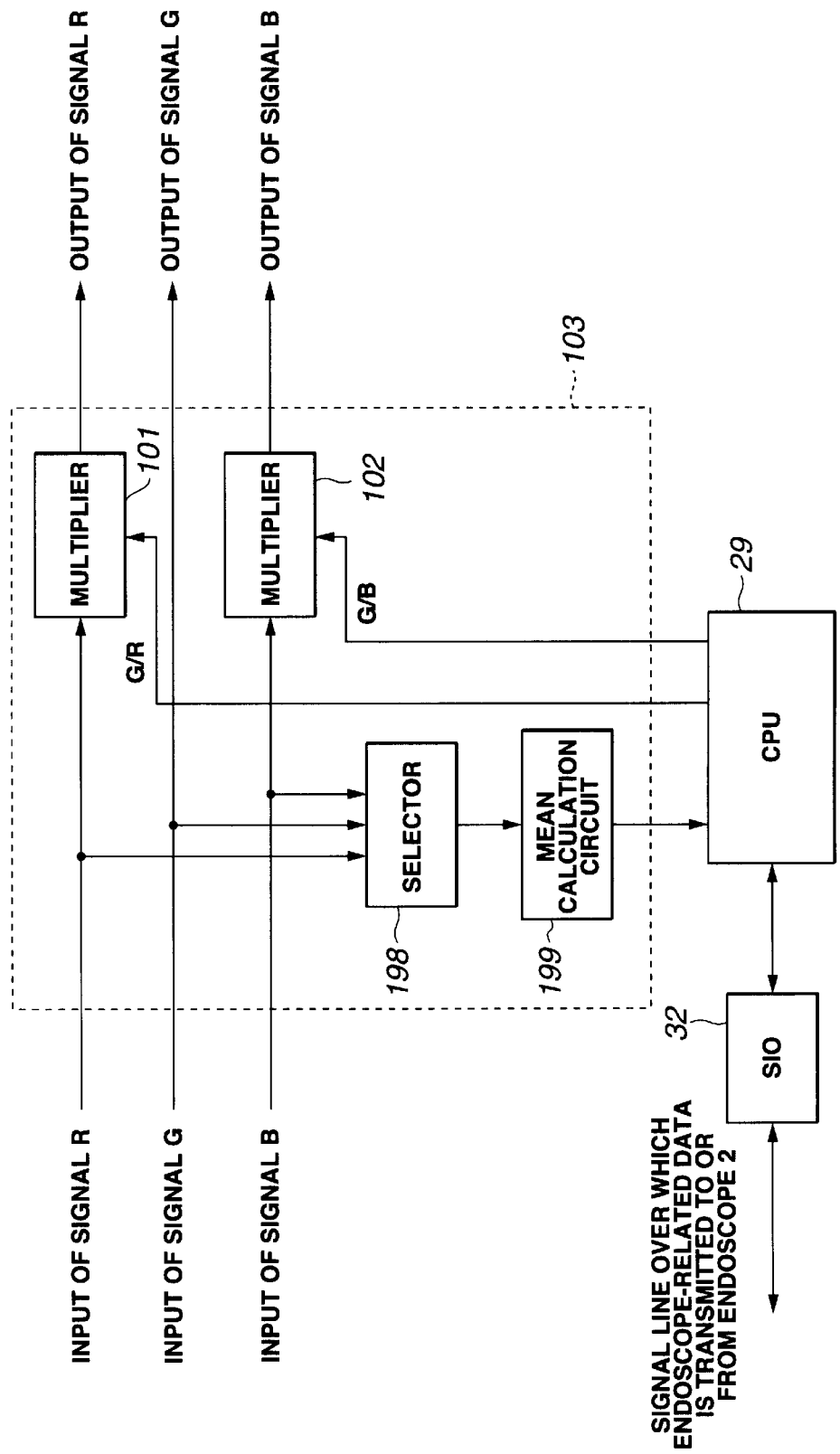
FIG. 44 is a block diagram showing a white balance control circuit and its surroundings.

FIG. 44 is a block diagram showing a white balance control circuit and its surroundings in the image processing apparatus 3A. FIG. 45 shows an example of switches on the operator panel 41 of the image processing apparatus 3A.

A red signal R, green signal G, and blue signal B are input to the white balance control circuit 103 in a video signal processing circuit 28, and then transferred to a selector 198. A mean calculation circuit 199 is connected to the output terminal of the selector 198. Means of values for the signals R, G, and B are calculated and output to the CPU 29.

The CPU 29 calculates a mean of values of a quotient G/R and a mean of values of a quotient G/B. The CPU 29 then inputs the means to multipliers 101 and 102 to which the signals R and B are input. The multipliers 101 and 102 multiply the signals R and B by the means.

The signals R and B controlled for attaining a white balance by means of the multipliers 101 and 102 are output together with the signal G to a succeeding stage. The white balance control circuit 103 is actuated with a white object imaged, whereby the signals R, G, and B controlled for attaining a white balance are produced.

The CPU 29 is connected on a signal line, over which the endoscope-related data is transmitted or received to or from the endoscope 2, via a serial controller 32. White balance data, that is, the mean of values of the quotient G/R and the mean of values of the quotient G/B that are referred to as a coefficient G/R and a coefficient G/B respectively may already be stored in the endoscope 2. In this case, the white balance data is read as described below so that a white balance will be attained automatically.

White balance data read from the endoscope 2 is input to the CPU 29 via the serial controller 32. The white balance data consists of the coefficients G/R and G/B. The CPU 29 inputs the coefficients G/R and G/B of the white balance data to the multipliers 101 and 102. The multipliers 101 and 102 multiply the signals R and B by the coefficients. A white balance is thus automatically attained.

Thereafter, a White Bal. key 190 shown in FIG. 45 is pressed to put off an internal LED, and a White Bal. indicator LED 191 is lit. A user is thus informed of the fact that white balance control has been extended.

Keys 181, 183, 187, 190, 192, 193, and 194 and LEDs 182, 184 to 186, 188 and 189, 191, and 195 to 197 which are arranged in a switch section 180 of the operator panel 41 as shown in FIG. 45 function as described in the table of FIG. 46. For example, the key 181 is a Print key, the LED 182 is a Print indicator LED, the key 183 is an Enhance key, and the LED 197 is a Tone Level indicator LED.

When the endoscope 2 is used to image a white balance chart (for example, a white balance cap), if the White Bal. key 190 is pressed, the selector 198 and the mean calculation circuit 199 are actuated to measure the mean signal levels of the signals R, G, and B. The CPU 29 calculates the coefficients (G/R and G/B) by which the signals R and B are multiplied. The multipliers 101 and 102 multiply the signals R and B by the coefficients. Thus, a white balance is attained. White balance data is written in the endoscope 2 via the serial controller 32. (In this case, the White Bal. key 190 has its internal LED held unlit, and the White Bal. indicator LED 191 remains lit.) If the white balance data read from the endoscope 2 assumes an initial value (for example, a value set at a factory before delivery), the CPU 29 lights the internal LED of the White Bal. key 190 shown in FIG. 45 and puts off the White Bal. indicator LED 191. Thus, a user is informed of the fact that a white balance has not been attained in the endoscope 2. At this time, the user may be prompted to press the White Bal. key 190 so as to extend white balance control.

Assume that the image processing apparatus 3A is connected to the endoscope 2' not having the communicating ability, and the power supply of the image processing apparatus 3A is turned on, or that the endoscope is replaced with the endoscope 2' with the power supply of the image processing apparatus 3A turned on. In this case, the endoscope 2' does not have white balance data. White balance control is therefore not extended automatically. The internal LED of the White Bal. key 190 is lit and the White Bal. indicator LED 191 is put off.

A user is thus informed of the fact that white balance control has not been extended, and prompted to press the White Bal. key 190. At this time, the buzzer 43 may be sounded in order to prompt the user to press the White Bal. key 190. Thereafter, when the endoscope 2' has imaged a white balance chart (for example, a white balance cap), the White Bal. key 190 is pressed. The selector 198 and mean calculation circuit 199 shown in FIG. 44 are then actuated to measure the mean levels of the signals R, G, and B. The CPU 29 calculates coefficients (G/R and G/B) by which the signals R and B are multiplied. The signals R and B are then multiplied by the coefficients. A white balance is thus attained. The internal LED of the White Bal. key 190 is put off and the White Bal. indicator LED 191 is lit, whereby it is indicated that a white balance has been attained in the endoscope 2'.

At steps S406 to S410, the pressing of the White Bal. key 190 to be made for attaining a white balance.may be inhibited so that white balance control may not be extended by mistake.

Whether the LEDs 190 and 191 shown in FIG. 45 are lit or put off is not limited to the foregoing example. For example, after a white balance is attained, the LEDs 190 and 191 may be put off. While white balance control is being extended, the LED 190 or 191 may be flickered.

After white balance control mentioned in FIG. 41is extended (S408), the image processing apparatus 3A reads remaining the endoscope-related data that has not been read (S409). Counting is executed in order to count the number of the power feeds read at step S407 (S410). Counting for counting the number of power feeds may be executed after step S409 or may be executed in a certain time (for example, 30 seconds) after step S405 irrespective of other processing. In this case, for example, if the power supply is turned on and off for a short period of time (within a certain time) in order to check an action, counting is not executed. The number of power feeds is therefore regarded as the number of times by which a user actually uses the endoscope.

Steps S408 to S410 may be performed after or during step S411. In this case, the steps S408 and S410 are performed only once after the power supply of the image processing apparatus 3A is turned on or one endoscope is replaced with another (S405).

In this case, after data is displayed at step S411, while other endoscope-related data is being read (S409), a Scope Information form may be displayed on the screen (S418 in FIG. 42). Although all of the endoscope-related data has not been read, the Screen Information form is displayed.

An indication ("Disable!") that reading is in progress is displayed in a display space 110 as shown in FIG. 47. Data whose reading is completed is displayed. After the reading of step S409 is completed, the state of the screen becomes as shown in FIG. 48 automatically.

Figure 49:
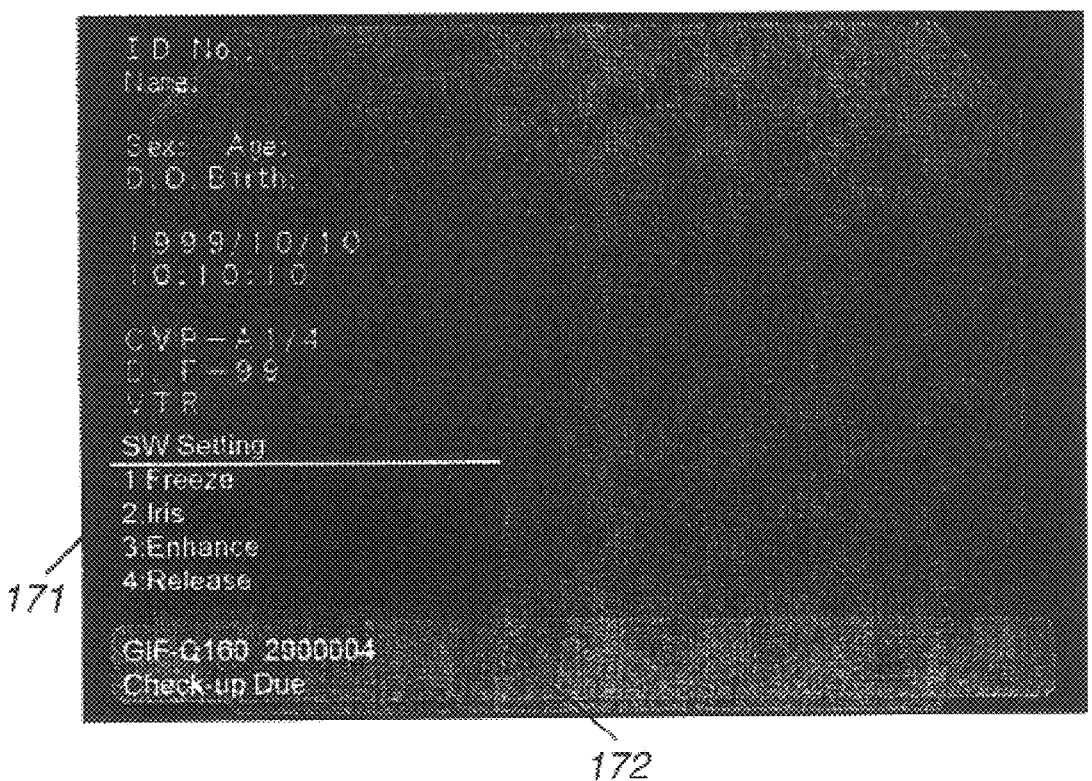
FIG. 49 shows an example of part of the endoscope-related data displayed below an endoscopic view image.
Figure 50:
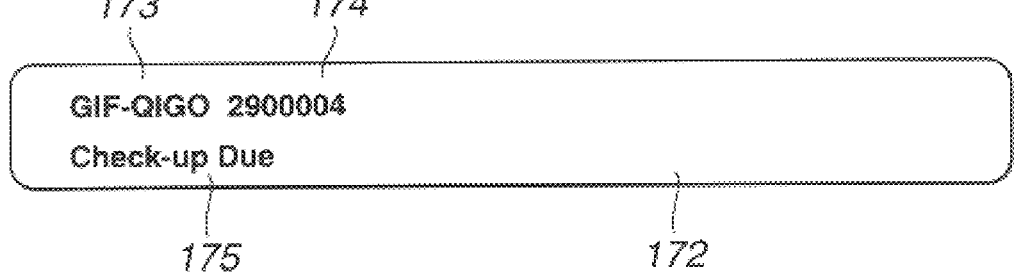
FIG. 50 is an enlarged view of an endoscope-related data display space shown in FIG. 49.
Figure 51:
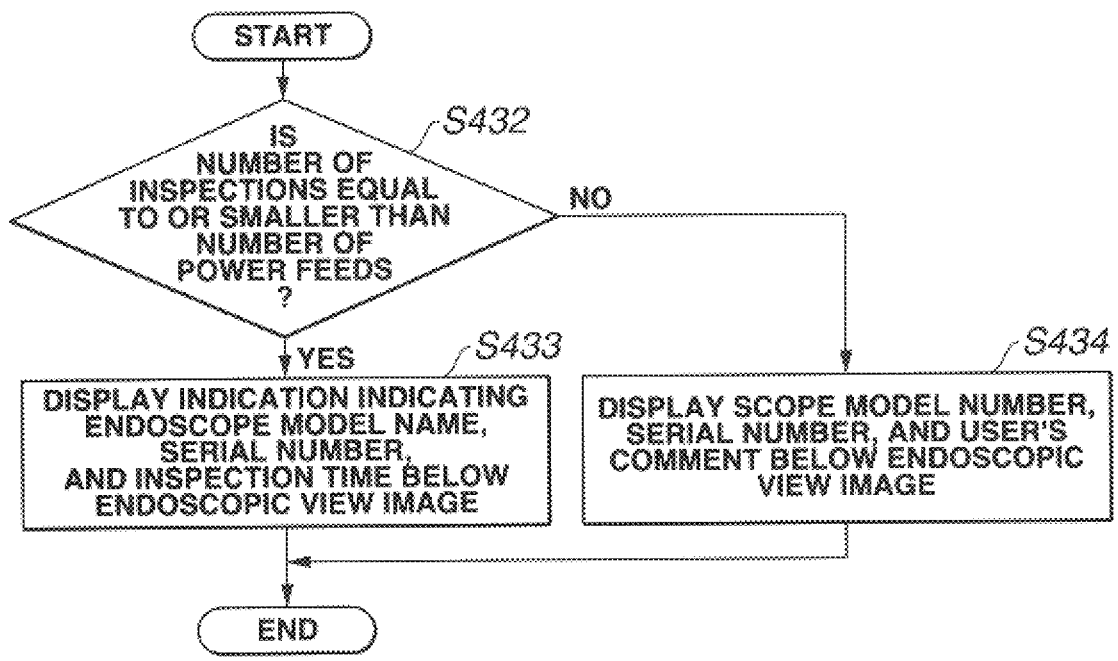
FIG. 51 is a flowchart describing the steps to be performed for indicating an inspection period.

Thereafter, an endoscope model name and a serial number contained in endoscope-related data is displayed below an endoscopic view image, and a user's comment or an inspection time is indicated (S411). FIG. 49 and FIG. 50 show examples of indications. FIG. 51 is a flowchart describing actions to be performed at step S411.

To begin with, the read number of power feeds is compared with the number of inspections (S432). If the number of power feeds is equal to or greater than the number of inspections, an endoscope model name is indicated at a position 173 within an endoscope-related data display space 172 shown in FIG. 49. A serial number is indicated at a position 174. An inspection time is indicated at a position 175 (for example, "Check-up Due" is displayed). FIG. 50 shows the contents of the endoscope-related data display space 172 shown in FIG. 49.

When the endoscope 2 has been used by the number of times equal to or greater than the number of inspections, a user is informed that it is time for inspection. The user can thus become aware of a right inspection time. If the number of power feeds falls below the number of inspections, an endoscope model name is indicated at the position 173 within the endoscope-related data display space 172, a serial number is indicated at the position 174, and a user's comment is indicated at the position 175.

The indication of an inspection time may be kept displayed until a user changes the number of inspections. Alternatively, the indication may be displayed once after the power supply of the image processing apparatus 3A is turned on or after one endoscope is replaced with another (S405).

Figure 52:
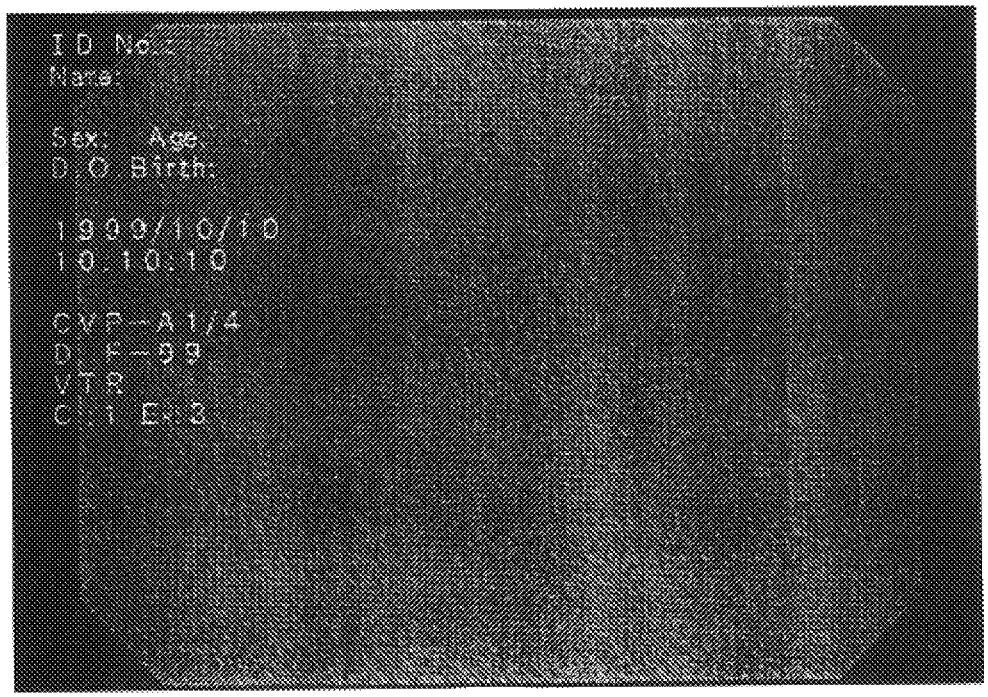
FIG. 52 shows an endoscopic view image alone.

Thereafter, assume that any key (except a Scope Info key) on the keyboard 44 is pressed (S412) or a certain time (for example, approximately 10 seconds) has elapsed (S413). In this case, the endoscope-related data display space 172 and a display space in which the information of the switches on the endoscope (see FIG. 49) are eliminated (S415). This brings the screen to an endoscopic view image displayed state (S416). FIG. 52 shows an example of the endoscopic view image displayed state.

If the Scope Info key on the keyboard 44 is pressed in the state attained at step S416, endoscope-related data is re-displayed below an endoscopic view image (S411).

If the Scope Info key is pressed with the endoscope-related data displayed below an endoscopic view image (S414), the Scope Information form shown in FIG. 42 appears (S418).

FIG. 48 and FIG. 53 show an example of information to be entered in the Scope Information form on the screen.

For example, an endoscope model name, a serial number, and an inspection time are indicated.

Among the displayed endoscope-related data, data displayed in display spaces 104 and 105 hatched in FIG. 48 can be rewritten. The other data cannot be rewritten.

For rewriting data, cursor movement keys on the keyboard 44 or operator panel 41 are pressed to move a cursor to a display spaced in which data must be entered. Character keys on the keyboard 44 are used to enter new data to be written. A selected display space in which data must be entered may be entirely highlighted like the display space 104 or the frame of the selected display space or entered characters alone may be highlighted.

Endoscope-related data to be displayed may be part of the endoscope-related data as shown in FIG. 48. Alternatively, all of the endoscope-related data may be displayed. Otherwise, a mode in which information that must be provided to a user is displayed and a mode in which information that must be reviewed by a service engineer is displayed may be programmed so that the modes can be switched using a key on the keyboard 44.

In FIG. 48, a display space 106 is a display space in which information concerning selected endoscope-related data, a way of moving the cursor, a way of writing data, or a way of displaying an endoscopic view image (FIG. 49) is described. The display space 106 is intended to help a user fill in the form shown in FIG. 48.

After the endoscope-related data listed in FIG. 53 is written or corrected in the Scope Information form shown in FIG. 48, it is determined whether, for example, a Return key on the keyboard 44 has been pressed (S419 in FIG. 42). If the Return key is pressed, "Are you sure? (Y/N)" (not shown) appears in the lower part of the Scope Information form on the screen (S421). If Y is designated, an indication that communication is in progress is displayed (S422). The endoscope-related data is then written (S423).

Data to be written may be data that has already been written or corrected. All the data in FIG. 48 that can be rewritten may be written irrespective of whether data has already been written or corrected.

For entering the number of inspections in the form shown in FIG. 48, the procedure described below is followed. Herein, assume that when the current number of power feeds has increased by 150, an inspection time is indicated at the position 175.

(1) The current number of power feeds (100) is checked.

(2) The sum of the current number of power feeds and 150 (100+150=250) is entered as the number of inspections.

When the expiration date of the guarantee is entered in the form shown in FIG. 48, the entered date is checked. If an incorrect date (for example, 13/47/2000) is entered, an alarm may be given (an error indication may be displayed on the screen or a buzzer may be sounded) in order to prevent the cursor from being moved to the display space for another endoscope-related data item. If a correct date has been entered or the display space for the expiration date of guarantee is left blank, the cursor can be moved to the display space for another data item.

Thereafter, endoscope-related data is displayed below an endoscopic view image (S425) (see FIG. 49). After the Return key is pressed (S419), if N is designated (S424), writing is not executed but the Scope Information form is re-displayed. If the Esc key is pressed (S420), endoscope-related data is displayed below an endoscopic view image (S425) (see FIG. 49).

After the endoscope-related data is displayed below an endoscopic view image (S425), if any key (except the Scope Info key) on the keyboard 44 is pressed (S426) or a certain time (for example, approximately 10 seconds) has elapsed (S427), the endoscope-related data display space 172 and the display space for the information of the switches on the endoscope (see FIG. 49) are eliminated (S429). This brings the screen to the endoscopic view image displayed state (S430) (see FIG. 52).

If the Scope Info key on the keyboard 44 is pressed in the state attained at step S430 (S431), the endoscope-related data is re-displayed below an endoscopic view image (S425).

When the Scope Info key is pressed with the endoscope-related data displayed below an endoscopic view image (S428), the Scope Information form displayed at step S418 is displayed.

Figure 54:
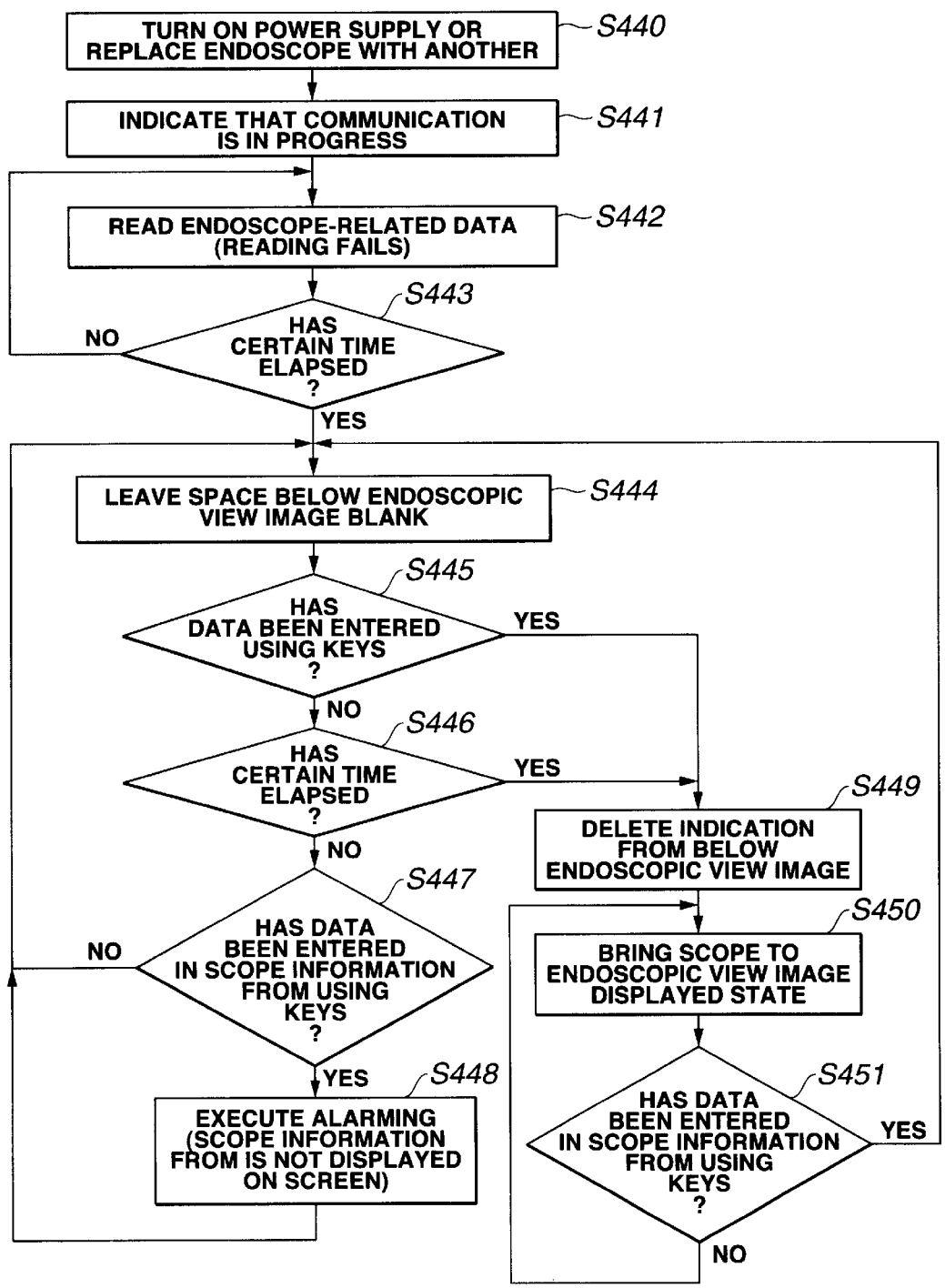
FIG. 54 is a flowchart describing the steps to be performed when an endoscope and an image processing apparatus both of which do not have communication capability are connected to each other.

FIG. 54 is a flowchart describing the processing when the image processing apparatus 3A and endoscope 2' are connected to each other. After the image processing apparatus 3A is connected to the endoscope 2', the power supply of the image processing apparatus 3A is turned on, or the endoscope 2' is replaced with another with the power supply of the image processing apparatus 3A turned on (S440). Thereafter, a connection sensing means (not shown) incorporated in the image processing apparatus 3A senses that the image processing apparatus 3A has been connected to the endoscope 2'. An indication that communication is in progress is then displayed (S441), and endoscope-related data is then read (S442).

The endoscope 2' does not have endoscope-related data stored therein. The image processing apparatus 3A may therefore fail to read the endoscope-related data despite its tries to execute reading for a certain period (S443). In this case, no endoscope-related data is displayed in the endoscope-related data display space 103 (S444) (see FIG. 55).

Thereafter, any key (except the Scope Info key) on the keyboard 44 may be pressed (S445) or a certain time (for example, approximately 10 seconds) may elapse (S446). At this time, the endoscope-related data display space 172 and the display space for the information of switches on the endoscope (see FIG. 49) are eliminated (S449). This brings the screen to the endoscopic view image displayed state (S450) (see FIG. 52).

If the Scope Info key on the keyboard 44 is pressed in the state attained at step S450 (S451), the display space below an endoscopic view image is left blank (S444).

It is determined with the display space below the endoscopic view image left blank whether the Scope Info key has been pressed (S447). If the Scope Info key has not been pressed, control is returned to step S444. Even if the Scope Info key has been pressed, since endoscope-related data is not read, alarming is executed (the buzzer 43 is sound or the LED 42 is lit or flickered). Control is then returned to step S444 with the Scope Information form not displayed on the screen (S448).

Figure 55:
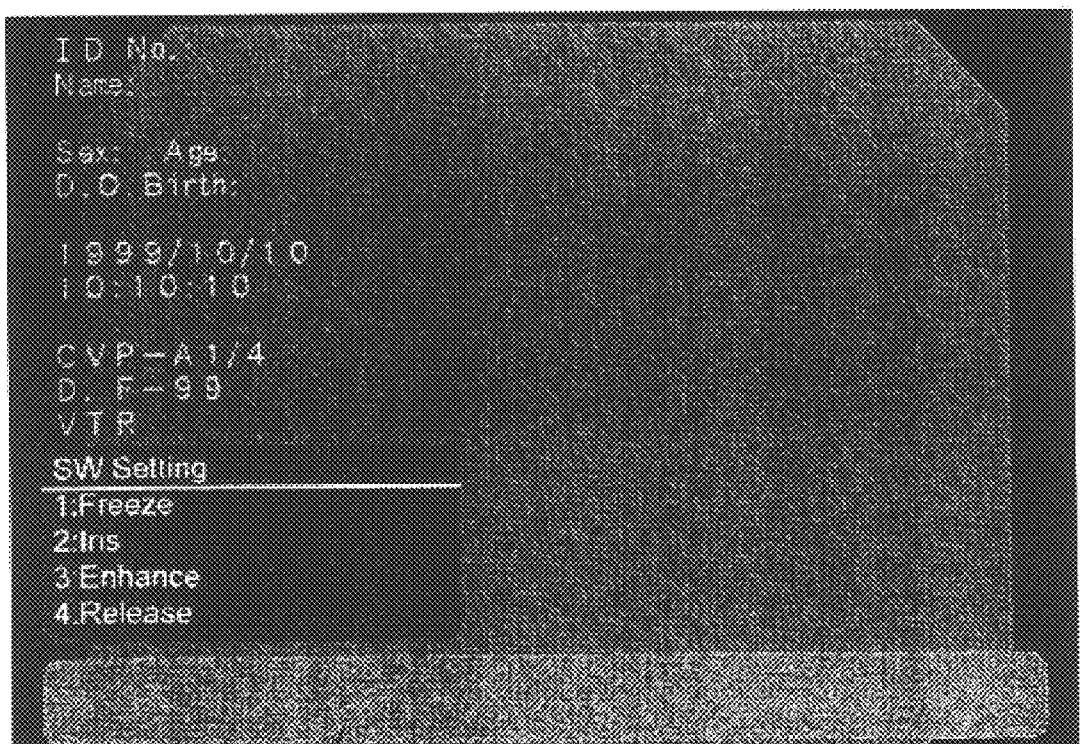
FIG. 55 shows an example of the state of a display space below an endoscopic view image attained when the reading of the endoscope-related data fails.
Figure 56:
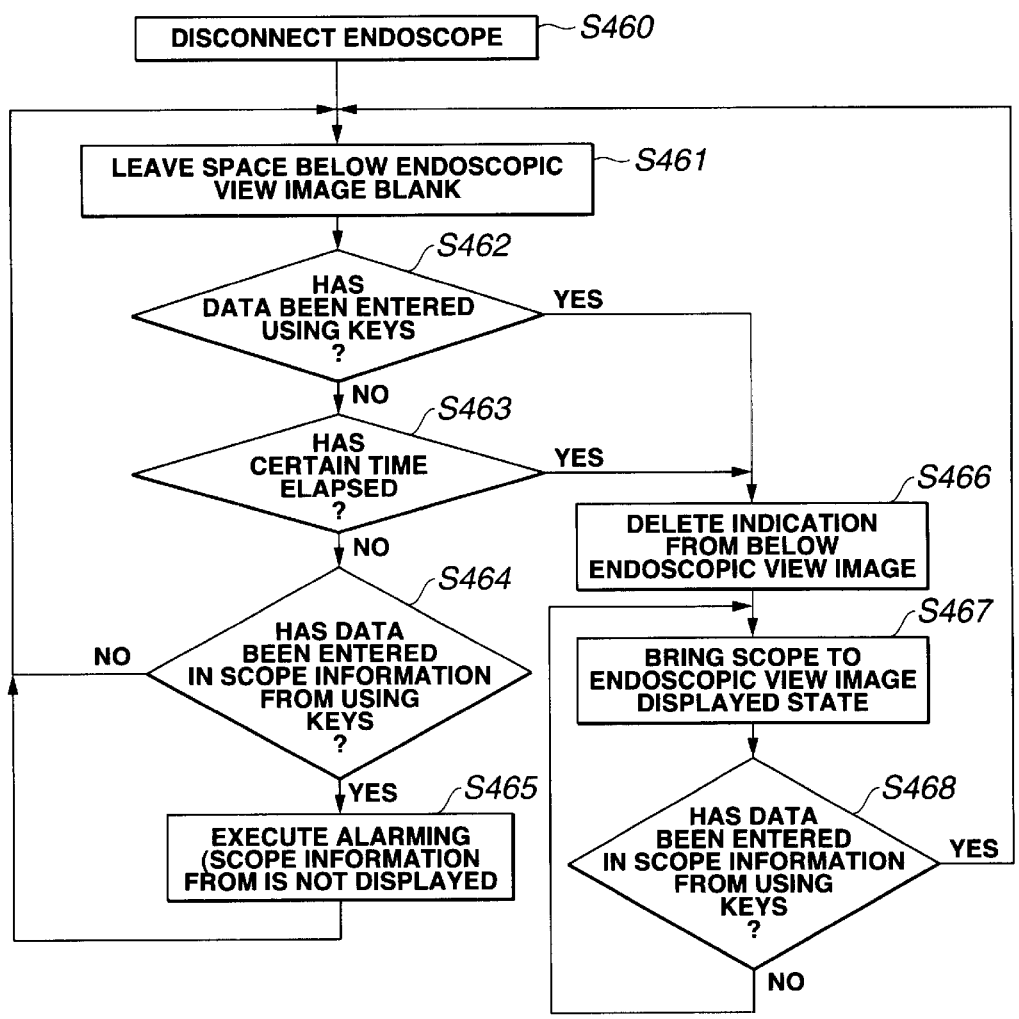
FIG. 56 is a flowchart describing the steps to be performed in an image processing apparatus from which an endoscope is disconnected.

FIG. 56 is a flowchart describing processing to be performed when the endoscopes 2 or 2' is disconnected from the image processing apparatus 3A. After the endoscope 2 or 2' is disconnected with the power supply of the image processing apparatus 3A turned on (S460), a connection sensing means incorporated in the image processing apparatus 3A senses that the image processing apparatus has been disconnected from the endoscope 2 or 2'. The endoscope-related data display space 103 is left blank (S461) (see FIG. 55).

Thereafter, if any key (except the Scope Info key) on the keyboard 44 is pressed (S462) or a certain time (for example, approximately 10 seconds) elapses (S463), the endoscope-related data display space and the display space for the information of switches on the endoscope which are shown in FIG. 55 are eliminated from below an endoscopic view image (S466). This brings the screen to the endoscopic view image displayed state (S467) (see FIG. 52). If the Scope Info key is pressed in the state attained at step S467 (S468), the display space below an endoscopic view image is still left blank (S461).

It is determined with the display space below an endoscopic view image left blank whether the Scope Info key has been pressed (S464). If the Scope Info key has not been pressed, control is returned to step S461. Even if the Scope Info key has been pressed, since the endoscope-related data is not read, alarming is executed (the buzzer 43 is sounded or the LED 42 is lit or flickered). Control is returned to step S461 with the Scope Information form not displayed on the screen (S465).

Characters representing the information 171 and 178 and the indication 176, which are shown in FIG. 43, and characters displayed as shown in FIG. 48 are written in English in the present embodiment. Alternatively, the characters may be written in any language of a nation in which the image processing apparatus 3A is used, such as, Japanese, German, or French. The languages may be switched using a key on the keyboard 44 or operator panel 41 or in a switching form (not shown) to be displayed on the screen by pressing any key.

Figure 57:
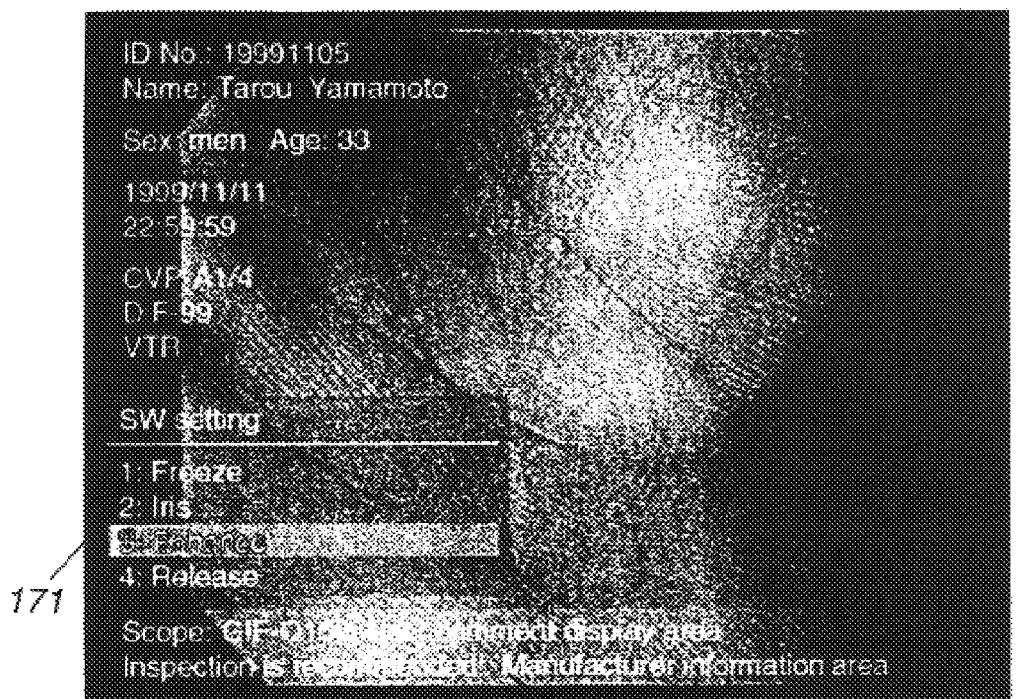
FIG. 57 shows another example of displaying a part of the endoscope-related data superimposed on an endoscopic view image.

FIG. 57 shows another example of displaying the endoscopic view image shown in FIG. 49. When the information 171 and the endoscope-related data in the display space 172 are superimposed on an endoscopic image produced by the endoscope 2, the endoscope image may be, as shown in FIG. 57, seen through the display space for the information 171 and the display space 172. In this case, the display space for the information 171 and the display space 172 are tinted in a transparent tone (for example, blue or green) different from the endoscopic image. Moreover, characters representing the information 171 and the endoscope-related data in the display space 172 are displayed in, for example, white.

Figure 58:
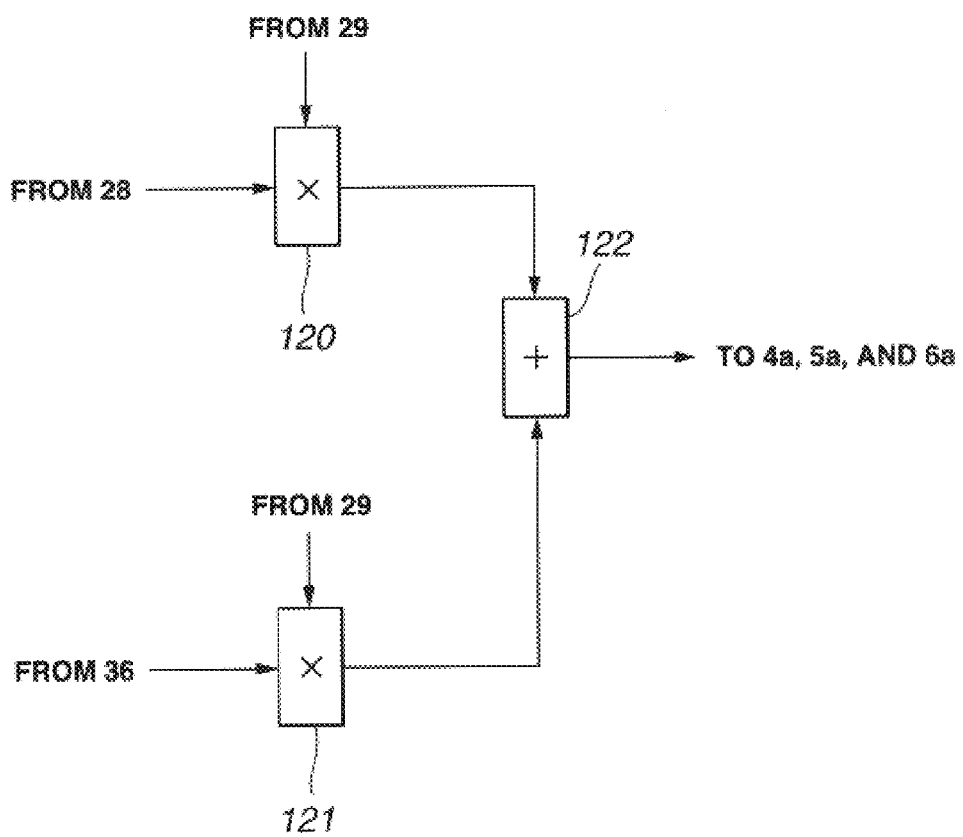
FIG. 58 is a block diagram showing a portion of a video signal switching circuit for synthesizing an endoscopic image and character information.

FIG. 58 is a block diagram showing part of the video signal switching circuit 29. Multipliers 120 and 121 multiply a signal representing an endoscopic image output from the video signal processing circuit 28 and a signal representing character information output from the display controller 36 (171 and 172) by a coefficient (for example, 0.5) set by the CPU 29. An adder 122 synthesizes the two signals. Consequently, the endoscopic image and character information are displayed in the manner shown in FIG. 57.

Multiplication performed by the multipliers 120 and 121 may be programmed in the CPU 29 or in the video signal switching circuit 37.

The present embodiment provides the advantages described below.

(1) The endoscope-related data (for example, an endoscope model name, a serial number, and a user's comment) is displayed below an endoscopic view image. A user can therefore readily obtain information unique to an endoscope employed. Moreover, since an inspection time for an endoscope is indicated, the endoscope can be maintained and managed easily. This is quite advantageous.

(2) White balance control is automatically extended. This is quite advantageous because no load is imposed on a user. Moreover, since each endoscope has white balance data stored therein, an image processing apparatus need not store white balance data. The image processing apparatus can therefore be designed compactly. An LED on an operator panel of the image processing apparatus indicates that white balance control extended based on white balance data has terminated. This contributes to improvement of working efficiency.

(3) A display form dedicated to endoscope-related data can be displayed on a screen. Information unique to each endoscope can be checked easily. Moreover, part of the information can be rewritten. A user can therefore customize the endoscope-related data. This contributes to improvement of working efficiency.

Although the present invention has been described in relation to particular embodiments thereof, many other variations and modifications and other uses will become apparent to those skilled in the art. It is preferred, therefore, that the present invention be limited not by,the specific disclosure herein, but only by the appended claims.

What is claimed is:

1. An endoscope system, comprising:
   an endoscope including,
      a storage medium for retrievably storing endoscope-related data;
      a first input/output terminal for inputting and outputting the endoscope-related data to and from said storage medium;
      a first transmission path linking said first input/output terminal and said storage medium for transmitting endoscope-related data to said storage medium from said input/output terminal; and
      a second transmission path linking said first input/output terminal and said storage medium for transmitting endoscope-related data from said storage medium to said first input/output terminal; and
   a peripheral apparatus including,
      a second input/output terminal for inputting and outputting endoscope-related data to or from said storage medium in said endoscope;
      an information reading unit for reading the endoscope-related data from said storage medium through said second input/output terminal;
      an information output unit for transmitting the endoscope-related data to said storage medium through said second input/output terminal;
      an information entry unit operatively connected to said information output unit for manual entry of information by a user to be transmitted and stored in said storage medium; and
      a signal transmission line linking said first input/output terminal of said endoscope and said second input/output terminal of said peripheral apparatus.

2. An endoscope system according to claim 1, wherein said storage medium is one of an EEPROM, a flash ROM, an FRAM, and an MRAM.

3. An endoscope system according to claim 1, wherein said endoscope has an imaging device for imaging an object.

4. An endoscope system according to claim 3, wherein a power supply for feeding power to said storage medium is used in common as a power supply for feeding power to said imaging device.

5. An endoscope system according to claim 3, wherein said peripheral apparatus further includes a video processing circuit, which produces a video signal from an output signal of said imaging device.

6. An endoscope system according to claim 5, wherein said display device displays an image of an object produced by said imaging device and endoscope-related data read from said storage medium.

7. An endoscope system according to claim 6, wherein said display device displays endoscope-related data read from said storage medium while superimposing it on part of an image of an object produced by said imaging device.

8. An endoscope system according to claim 3, wherein said endoscope is connected to said peripheral apparatus by a connector cable to which said imaging device is also connected.

9. An endoscope system according to claim 1, wherein said storage medium holds confirmation information for confirming that endoscope-related data has been written correctly, and further comprising a confirmation unit for using the confirmation information to confirm whether endoscope-related data written in said storage medium is correct.

10. An endoscope system according to claim 1, wherein before at least part of the endoscope-related data is written in said storage medium, write enabling must be executed.

11. An endoscope system according to claim 1, wherein the endoscope-related data to be written in said storage medium includes one of an initial examination day and an institution name, and wherein when the initial examination day or institution name is not stored in said storage medium, said peripheral equipment automatically writes one of the initial examination day and institution name in said storage medium.

12. An endoscope system according to claim 11, wherein said peripheral apparatus further includes an alarming unit for providing an alarm to indicate that it is time for an inspection after a predetermined time past an initial examination day.

13. An endoscope system according to claim 1, wherein said storage medium has an area in which a user's comment can be retrievably stored, wherein said peripheral apparatus further includes au operation unit for entering the user's comment.

14. An endoscope system according to claim 1, wherein the endoscope-related data includes information relevant to cleaning said endoscope.

15. An endoscope system according to claim 1, wherein said peripheral apparatus includes an operation unit for displaying the endoscope-related data on a display device.

16. An endoscope according to claim 1, wherein said endoscope further comprises a supply voltage detector which detects a fluctuation or drop in supply voltage regulated by a regulator and outputs a reset signal.

17. An endoscope system, comprising:
   an endoscope including,
      a storage medium for retrievably storing endoscope-related data;
      a first input/output terminal for inputting and outputting the endoscope-related data to and from said storage medium;
      a first transmission path linking said first input/output terminal and said storage medium for transmitting endoscope-related data to said storage medium from said input/output terminal; and
      a second transmission path linking said first input/output terminal and said storage medium for transmitting endoscope-related data from said storage medium to said first input/output terminal; and
         a peripheral apparatus including, a second input/output terminal for inputting and outputting endoscope-related data to or from said storage medium in said endoscope;
         an information reading unit for reading the endoscope-related data from said storage medium through said second input/output terminal; and
         an information output unit for transmitting the endoscope-related data to said storage medium through said second input/output terminal; and
         a signal transmission line linking said first input/output terminal of said endoscope and said second input/output terminal of said peripheral apparatus, wherein backup data of the endoscope-related data is stored in said storage medium.

18. An endoscope according to claim 17, wherein said endoscope further comprises a supply voltage detector which detects a fluctuation or drop in supply voltage regulated by a regulator and outputs a reset signal.

19. An endoscope system, comprising:
   an endoscope including,
      a storage medium for retrievably storing endoscope-related data;
      a first input/output terminal for inputting and outputting the endoscope-related data to and from said storage medium;
      a first transmission path linking said first input/output terminal and said storage medium for transmitting endoscope-related data to said storage medium from said input/output terminal; and
      a second transmission path linking said first input/output terminal and said storage medium for transmitting endoscope-related data from said storage medium to said first input/output terminal; and
         a peripheral apparatus including, a second input/output terminal for inputting and outputting endoscope-related data to or from said storage medium in said endoscope;
         an information reading unit for reading the endoscope-related data from said storage medium through said second input/output terminal; and
         an information output unit for transmitting the endoscope-related data to said storage medium through said second input/output terminal; and
         a signal transmission line linking said first input/output terminal of said endoscope and said second input/output terminal of said peripheral apparatus, wherein the endoscope-related data includes count data indicating a number of power feeds by which power is fed to said endoscope, wherein said endoscope further includes a counting device for counting the number of power feeds and an identifying device for identifying peripheral equipment, and the number of power feeds is counted based on the results of identification performed by said identifying device.

20. An endoscope system according to claim 19, wherein an alarm is sounded when the number of power feeds exceeds a predetermined value.

21. An endoscope system, comprising:
   an endoscope including,
      an imaging device used for imaging incorporated in a distal part of an insertion unit insertable into a subject;
      a storage medium for retrievably storing endoscope-related data relevant to an endoscope;
      a first input/output terminal for inputting and outputting endoscope-related data to and from said storage medium;
      a first transmission path linking said first input/output terminal and said storage medium for transmitting the endoscope-related data from said input/output terminal to said storage medium; and
      a second transmission path linking said first input/output terminal and said storage medium for transmitting the endoscope-related data from said storage medium to said first input/output terminal;
   an image processing apparatus, connected to said endoscope, for producing a video signal from an output signal of said imaging device;
   a display device for displaying an image of an object according to a video signal to be input; and
   a peripheral apparatus including,
      a second input/output terminal for inputting and outputting the endoscope-related data to and from said storage medium;
      an information reading unit for reading the endoscope-related data from said storage medium through said second input/output terminal;
      an information output unit for transmitting the endoscope-related data to be stored in said storage medium through said second input/output terminal; and
      an information entry unit operatively connected to said information output unit for manual entry of information by a user to be transmitted and stored in said storage medium.

22. An endoscope system according to claim 21, wherein said storage medium is one of an EEPROM, a flash ROM, an FRAM, and an MRAM.

23. An endoscope system according to claim 21, wherein the endoscope-related data contains a number of power feeds and a number of inspections, and wherein when the number of power feeds become equal to or greater than the number of inspections, said display device indicates that it is time for an inspection.

24. An endoscope system according to claim 23, wherein when the number of power feeds becomes equal to or greater than the number of inspections, it is indicated in a display space that it is time for an inspection.

25. An endoscope system according to claim 21, wherein the endoscope-related data includes an endoscope model name, a serial number, and a user's comment, and the endoscope model name, serial number, and user's comment are read prior to the other endoscope-related data and displayed on said display device.

26. An endoscope system according to claim 21, wherein the endoscope-related data contains white balance data used to attain a white balance.

27. An endoscope system according to claim 26, wherein said image processing apparatus extends white balance control using the white balance data, and said display device is-used to indicate that white balance control has terminated.

28. An endoscope system according to claim 21, wherein said display device displays endoscope-related data read from said storage medium while superimposing it on part of an image of an object produced by said imaging device.

29. An endoscope system according claim 28, wherein the endoscope-related data includes at least one of an endoscope model name, a serial number, a user's comment, and an inspection time.

30. An endoscope system according to claim 29, wherein when the number of power feeds becomes equal to or greater than the number of inspections, an inspection time is indicated instead of a user's comment.

31. An endoscope according to claim 21, wherein said endoscope further comprises a supply voltage detector which detects a fluctuation or drop in supply voltage regulated by a regulator and outputs a reset signal.

32. An endoscope, comprising:

an imaging device incorporated in the distal part of an insertion unit thereof to be inserted into a subject, and used for imaging;

a storage medium for retrievably storing endoscope-related data relevant to an endoscope;

a first input/output terminal for inputting and outputting endoscope-related data to and from said storage medium;

a first transmission path linking said first input/output terminal and said storage medium for transmitting the endoscope-related data to said storage medium; and a second transmission path linking said first input/output terminal and said storage medium for transmitting the endoscope-related data from said storage medium to said first input/output terminal; and an information entry unit in communication with said storage medium for manual entry of information by a user to be transmitted and stored in said storage medium.

33. An endoscope according to claim 32, wherein said storage medium is one of an EEPROM, a flash ROM, an FRAM, or an MRAM.

34. An endoscope according to claim 32, wherein said information entry unit is a keyboard.

35. An endoscope according to claim 32, wherein said endoscope further comprises a supply voltage detector which detects a fluctuation or drop in supply voltage regulated by a regulator and outputs a reset signal.

36. An endoscope system, comprising:

an endoscope having an imaging device incorporated in the distal part of an insertion unit thereof to be inserted into a subject to permit endoscopic examination, an image processing apparatus, connected to said endoscope, for producing a video signal from an output of said imaging device;

a display device for displaying an image of an object according to the video signal;

a programmable storage medium incorporated in said endoscope and used to store endoscope-related data relevant to said endoscope;

a communication unit to enable writing or reading of the endoscope-related data in or from said storage medium and allowing the data to be communicated to or from said image processing apparatus;

an information entry unit operatively connected to said communication unit for manual entry of information by a user to be transmitted and stored in said storage medium; and a control unit for displaying the endoscope-related data on said display device at any time.

37. An endoscope system according to claim 36, wherein said communication unit includes a serial interface enabling serial data transmission.

38. An endoscope system according to claim 37, wherein a sole signal line to be coupled to said serial interface is used in common for transmission and reception.

39. An endoscope system according to claim 36, wherein said storage medium is one of an EEPROM, a flash ROM, an FRAM, and an MRAM.

40. An endoscope system according to claim 36, wherein the endoscope-related data contains the number of power feeds and the number of inspections, and wherein when the number of power feeds becomes equal to or greater than the number of inspections, said display device indicates that it is an inspection time.

41. An endoscope system according to claim 40, wherein when the number of power feeds becomes equal to or greater than the number of inspections, an indication of inspection time is indicated in a display space where user's comment is indicated.

42. An endoscope system according to claim 40, wherein when the number of power feeds becomes equal to or greater than the number of inspections, an indication of inspection time is indicated instead of the user's comment.

43. An endoscope system according to claim 36, wherein the endoscope-related data contains an endoscope model name, a serial number, and a user's comment, and the endoscope model name, serial number, and user's comment are read prior to the other endoscope-related data and displayed on said display device.

44. An endoscope system according to claim 36, wherein the endoscope-related data contains white balance data used to attain a white balance.

45. An endoscope system according to claim 44, wherein said image processing apparatus extends white balance control using the white balance data, and said display device is used to indicate that white balance control has terminated.

46. An endoscope system according to claim 36, wherein said display device displays endoscope-related data read from said storage medium while superimposing it on part of an image of an object produced by said imaging device.

47. An endoscope system according to claim 46, wherein the endoscope-related data contains an endoscope model name, a serial number, a user's comment or an inspection time.

48. An endoscope system according to claim 36, wherein said information entry unit is a keyboard.

49. An endoscope system according to claim 48, wherein when said display device displays a data display form, which is filled in for displaying data, on its screen, data can be entered at said keyboard.

50. An endoscope system according to claim 49, wherein when said data display form is displayed on the screen, data items that can be entered and data items that cannot be entered can be distinguished from each other.

51. An endoscope system according to claim 36, wherein a plurality of different data display forms having data items that are different from each other is available.

52. An endoscope system according to claim 49, wherein when said data display form is displayed on the screen, the endoscope-related data entered at said keyboard is stored in said storage medium.

53. An endoscope according to claim 36, wherein said endoscope further comprises a supply voltage detector which detects a fluctuation or drop in supply voltage regulated by a regulator and outputs a reset signal.

* * * * *